US010617656B2

(12) United States Patent
Parello et al.

(10) Patent No.: US 10,617,656 B2
(45) Date of Patent: *Apr. 14, 2020

(54) METHODS OF INCREASING THE CYTOTOXICITY OF CHEMOTHERAPEUTIC AGENTS WITH MULTISUBSTRATE INHIBITORS OF HISTONE, PROTEIN-LYS, POLYAMINE ACETYLATION, AND POLYAMINE METABOLISM

(71) Applicant: Vanderbilt University, Nashville, TN (US)

(72) Inventors: Joseph Parello, Nashville, TN (US); Ruth Anne Gjierset, San Diego, CA (US); Paul R. Reid, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 53 days.

This patent is subject to a terminal disclaimer.

(21) Appl. No.: 14/829,453

(22) Filed: Aug. 18, 2015

(65) Prior Publication Data

US 2016/0243063 A1 Aug. 25, 2016

Related U.S. Application Data

(63) Continuation of application No. 13/078,836, filed on Apr. 1, 2011, now abandoned.

(60) Provisional application No. 61/320,117, filed on Apr. 1, 2010.

(51) Int. Cl.
| | | |
|---|---|---|
| A61K 31/16 | (2006.01) | |
| A61K 31/52 | (2006.01) | |
| A61K 31/198 | (2006.01) | |
| A61K 31/4745 | (2006.01) | |
| A61K 31/513 | (2006.01) | |
| A61K 31/704 | (2006.01) | |
| A61K 33/24 | (2019.01) | |
| A61K 31/675 | (2006.01) | |
| A61K 31/7048 | (2006.01) | |
| A61K 45/06 | (2006.01) | |
| A61K 31/555 | (2006.01) | |
| A61K 31/708 | (2006.01) | |
| A61K 31/475 | (2006.01) | |
| A61K 31/7068 | (2006.01) | |

(52) U.S. Cl.
CPC ............ *A61K 31/16* (2013.01); *A61K 31/198* (2013.01); *A61K 31/475* (2013.01); *A61K 31/4745* (2013.01); *A61K 31/513* (2013.01); *A61K 31/52* (2013.01); *A61K 31/555* (2013.01); *A61K 31/675* (2013.01); *A61K 31/704* (2013.01); *A61K 31/708* (2013.01); *A61K 31/7048* (2013.01); *A61K 31/7068* (2013.01); *A61K 33/24* (2013.01); *A61K 45/06* (2013.01)

(58) Field of Classification Search
None
See application file for complete search history.

(56) References Cited

U.S. PATENT DOCUMENTS 4,826,968 A * 5/1989 Pegg .................. C07H 19/207
530/331
5,030,564 A * 7/1991 Mitsuhashi ............ C07K 16/24
435/452

OTHER PUBLICATIONS

Bandyopadhyay et al., (Cell Cycle , 2009, v.8 pp. 2779-2788 ).*
Allfrey, V. G. and Mirsky, A. E. Structural Modifications of Histones and their Possible Role in the Regulation of RNA Synthesis. Science, 144: 559, 1964.
Allis, C. D., Berger, S. L., Cote, J., Dent, S., Jenuwien, T., Kouzarides, T., Pillus, L., Reinberg, D., Shi, Y., Shiekhattar, R., Shilatifard, A., Workman, J., and Zhang, Y. New nomenclature for chromatin-modifying enzymes. Cell, 131: 633-636, 2007.
Allis, C. D., Chicoine, L. G., Richman, R., and Schulman, I. G. Deposition-related histone acetylation in micronuclei of conjugating Tetrahymena. Proc Natl Acad Sci U S A, 82: 8048-8052, 1985.
Auvinen, M., Paasinen, A., Andersson, L. C., and Holtta, E. Ornithine decarboxylase activity is critical for cell transformation. Nature 1992; 360:355-8.
Avemann, K., Knippers, R., Koller, T., and Sogo, J. M. Camptothecin, a specific inhibitor of type I DNA topoisomerase, induces DNA breakage at replication forks. Mol Cell Biol, 8: 3026-3034, 1988.

(Continued)

*Primary Examiner* — Michail A Belyavskyi
(74) *Attorney, Agent, or Firm* — Stites & Harbison PLLC; Richard S. Myers, Jr.

(57) ABSTRACT

A method of treating cancer in a subject in need thereof, comprising administering to the subject a first amount of a compound of the HAT inhibitor of the following formula:

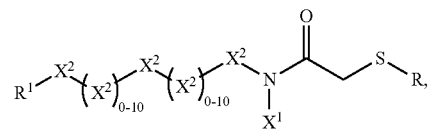

wherein R is chosen from coenzyme A, $(CH_2)_2NHCO(CH_2)_2NHCOR^2$; $(CH_2)_2NHCOR^3$; $(CH_2)_2NHCO(CH_2)_2NHCOR^4$; $R^1$ is H, $NH_2$, NH, N, and $R^1$ can optionally cyclize with at least one other $X^2$ to form a $C_{3-8}$ membered ring containing C, O, S, or N; $R^2$ is chosen from alkyl, cycloalkyl, aryl, heteroaryl; $R^3$ is chosen from an alkyl, cycloalkyl, aryl, heteroaryl; $R^4$ is chosen from $CH(OH)C(CH_3)_2CH_2)OCOR^2$; $X^1$ is chosen from H or can cyclize with one other $X^2$ or $R^1$ to form a $C_{3-8}$ membered ring containing C, O, S, or N; and $X^2$ is chosen from C, N, NH, and can optionally cyclize with at least one other $X^2$ or $R^1$ to form a $C_{3-8}$ membered ring containing C, O, S, or N; or a pharmaceutically acceptable salt or hydrate thereof, thereby treating the cancer.

5 Claims, 21 Drawing Sheets

(56) References Cited

OTHER PUBLICATIONS

Balasubramanyam, K., Altaf, M., Varier, R. A., Swaminathan, V., Ravindran, A., Sadhale, P. P., and Kundu, T. K. Polyisoprenylated benzophenone, garcinol, a natural histone acetyltransferase inhibitor, represses chromatin transcription and alters global gene expression. J Biol Chem, 279: 33716-33726, 2004.
Balasubramanyam, K., Swaminathan, V., Ranganathan, A., and Kundu, T. K. Small molecule modulators of histone acetyltransferase p300. J Biol Chem, 278: 19134-19140, 2003.
Balasubramanyam, K., Varier, R. A., Altaf, M., Swaminathan, V., Siddappa, N. B., Ranga, U., and Kundu, T. K. Curcumin, a novel p300/CREB-binding protein-specific inhibitor of acetyltransferase, represses the acetylation of histone/nonhistone proteins and histone acetyltransferase-dependent chromatin transcription. J Biol Chem, 279: 51163-51171, 2004.
Bandyopadhyay, K., Baneres, J. L., Martin, A., Blonski, C., Parello, J., and Gjerset, R. A. (2009) Spermidinyl-CoA-based HAT inhibitors block DNA repair and provide cancer-specific chemo- and radiosensitization. 2009, Cell Cycle 8, 2779-2788.
Bandyopadhyay, K., Lee, C., Haghighi, A., Baneres, J. L., Parello, J., and Gjerset, R. A. Serine phosphorylation-dependent coregulation of topoisomerase I by the p14ARF tumor suppressor. Biochemistry, 46: 14325-14334, 2007.
Baneres, J. L., Martin, A., and Parello, J. The N tails of histones H3 and H4 adopt a highly structured conformation in the nucleosome. J Mol Biol, 273: 503-508, 1997.
Bernacki, R. J., Oberman, E. J., Seweryniak, K. E., Atwood, A., Bergeron, R. J., and Porter, C. W. (1995) Preclinical antitumor efficacy of the polyamine analogue N1, N11-diethylnorspermine administered by multiple injection or continuous infusion. Clin Cancer Res 1, 847-857.
Bogdanov, K. V., Chukhlovin, A. B., Zaritskey, A. Y., Frolova, O. I., and Afanasiev, B. V. Ultraviolet irradiation induces multiple DNA double-strand breaks and apoptosis in normal granulocytes and chronic myeloid leukaemia blasts. Br J Haematol, 98: 869-872, 1997.
Canizares, F., Salinas, J., de las Heras, M., et al. Prognostic value of ornithine decarboxylase and polyamines in human breast cancer: correlation with clinicopathologic parameters. Clin Cancer Res 1999; 5:2035-41.
Casero, R. A., Jr. and Woster, P. M. Recent advances in the development of polyamine analogues as antitumor agents. J Med Chem 2009; 52:4551-73.
Cazzalini, O., Perucca, P., Savio, M., Necchi, D., Bianchi, L., Stivala, L. A., Ducommun, B., Scovassi, A. I., and Prosperi, E. Interaction of p21(CDKN1A) with PCNA regulates the histone acetyltransferase activity of p300 in nucleotide excision repair. Nucleic Acids Res, 36: 1713-1722, 2008.
Cullis, P. M., Wolfenden, R., Cousens, L. S., and Alberts, B. M. Inhibition of histone acetylation by N-[2-(S-coenzyme A)acetyl] spermidine amide, a multisubstrate analog. J Biol Chem, 257: 12165-12169, 1982.
Dumuis-Kervabon, A., Encontre, I., Etienne, G., Jauregui-Adell, J., Mery, J., Mesnier, D., and Parello, J. A chromatin core particle obtained by selective cleavage of histones by clostripain. Embo J, 5: 1735-1742, 1986.
Eliseeva, E. D., Valkov, V., Jung, M., and Jung, M. O. Characterization of novel inhibitors of histone acetyltransferases. Mol Cancer Ther, 6: 2391-2398, 2007.
Garcia-Carbonero, R. and Supko, J. G. Current perspectives on the clinical experience, pharmacology, and continued development of the camptothecins. Clin Cancer Res, 8: 641-661, 2002.
Gerner, E. W. and Meyskens, F. L., Jr. Polyamines and cancer: old molecules, new understanding. Nat Rev Cancer 2004; 4:781-92.
Hart, I. R., and Easty, D. (1991) Tumor cell progression and differentiation in metastasis. Semin Cancer Biol 2, 87-95.
Hasan, S., Hassa, P. O., Imhof, R., and Hottiger, M. O. Transcription coactivator p300 binds PCNA and may have a role in DNA repair synthesis. Nature, 410: 387-391, 2001.
Herceg, Z. and Wang, Z. Q. Rendez-vous at mitosis: TRRAPed in the chromatin. Cell Cycle, 4: 383-387, 2005.
Hu, R. H. and Pegg, A. E. Rapid induction of apoptosis by deregulated uptake of polyamine analogues. Biochem J 1997; 328 (Pt 1):307-16.
Jacobson, S. and Pillus, L. Modifying chromatin and concepts of cancer. Curr Opin Genet Dev, 9: 175-184, 1999.
Jun, J. Y., Griffith, J. W., Bruggeman, R., et al. Effects of polyamine depletion by alpha-difluoromethylornithine on in vitro and in vivo biological properties of 4T1 murine mammary cancer cells. Breast Cancer Res Treat 2008; 107:33-40.
Kornberg, R. D. and Lorch, Y. Twenty-five years of the nucleosome, fundamental particle of the eukaryote chromosome. Cell, 98: 285-294, 1999.
Kusch, T., Florens, L., Macdonald, W. H., Swanson, S. K., Glaser, R. L., Yates, J. R., 3rd, Abmayr, S. M., Washburn, M. P., and Workman, J. L. Acetylation by Tip60 is required for selective histone variant exchange at DNA lesions. Science, 306: 2084-2087, 2004.
Lau, O. D., Kundu, T. K., Soccio, R. E, Ait-Si-Ali, S., Khalil, E. M., Vassilev, A., Wolffe, A. P., Nakatani, Y., Roeder, R. G., and Cole, P. A. HATs off: selective synthetic inhibitors of the histone acetyltransferases p300 and PCAF. Mol Cell, 5: 589-595, 2000.
Lee, D. Y., Hayes, J. J., Pruss, D., and Wolffe, A. P. A positive role for histone acetylation in transcription factor access to nucleosomal DNA. Cell, 72: 73-84, 1993.
Manni, A., Mauger, D., Gimotty, P., and Badger, B. Prognostic influence on survival of increased ornithine decarboxylase activity in human breast cancer. Clin Cancer Res 1996; 2:1901-6.
Manni, A., Washington, S., Craig, L., et al. Effects of alpha-difluoromethylornithine on local recurrence and pulmonary metastasis from MDA-MB-435 breast cancer xenografts in nude mice. Clin Exp Metastasis 2003; 20:321-5.
Manni, A., Washington, S., Griffith, J. W., et al. Influence of polyamines on in vitro and in vivo features of aggressive and metastatic behavior by human breast cancer cells. Clin Exp Metastasis 2002; 19:95-105.
Manni, A., Washington, S., Hu, X., et al. Effects of polyamine synthesis inhibitors on primary tumor features and metastatic capacity of human breast cancer cells. Clin Exp Metastasis 2005; 22:255-63.
Morris, G. J., Naidu, S., Topham, A. K., Guiles, F., Xu, Y., McCue, P., Schwartz, G. F., Park, P. K., Rosenberg, A. L., Brill, K., and Mitchell, E. P. (2007) Differences in breast carcinoma characteristics in newly diagnosed African-American and Caucasian patients: a single-institution compilation compared with the National Cancer Institute's Surveillance, Epidemiology, and End Results database. Cancer 110, 876-884.
Pavon, M. A., Parreno, M., Leon, X., Sancho, F. J., Cespedes, M. V., Casanova, I., Lopez-Pousa, A., Mangues, M. A., Quer, M., Barnadas, A., and Mangues, R. Ku70 predicts response and primary tumor recurrence after therapy in locally advanced head and neck cancer. Int J Cancer, 123: 1068-1079, 2008.
Pegg, A. E. Polyamine metabolism and its importance in neoplastic growth and a target for chemotherapy. Cancer Res 1988; 48:759-74.
Pegg, A. E. Spermidine/spermine-N(1)-acetyltransferase: a key metabolic regulator. Am J Physiol Endocrinol Metab, 294: E995-1010, 2008.
Persson, L. and Rosengren, E. Increased formation of N1-acetylspermidine in human breast cancer. Cancer Lett 1989; 45:83-6.
Rogakou, E. P., Boon, C., Redon, C., and Bonner, W. M. Megabase chromatin domains involved in DNA double-strand breaks in vivo. J Cell Biol, 146: 905-916, 1999.
Saadatmandi, N., Tyler, T., Huang, Y., Haghighi, A., Frost, G., Borgstrom, P., and Gjerset, R. A. Growth suppression by a p14(ARF) exon 1beta adenovirus in human tumor cell lines of varying p53 and Rb status. Cancer Gene Ther, 9: 830-839., 2002.

(56) References Cited

OTHER PUBLICATIONS

Seiler, N., Delcros, J. G., and Moulinoux, J. P. Polyamine transport in mammalian cells. An update. Int J Biochem Cell Biol 1996; 28:843-61.

Sorlie, T., Tibshirani, R., Parker, J., Hastie, T., Marron, J. S., Nobel, A., Deng, S., Johnsen, H., Pesich, R., Geisler, S., Demeter, J., Perou, C. M., Lonning, P. E., Brown, P. O., Borresen-Dale, A. L., and Botstein, D. (2003) Repeated observation of breast tumor subtypes in independent gene expression data sets. Proc Natl Acad Sci U S A 100, 8418-8423.

Suter, B., Pogoutse, O., Guo, X., Krogan, N., Lewis, P., Greenblatt, J. F., Rine, J., and Emili, A. Association with the origin recognition complex suggests a novel role for histone acetyltransferase Hat1p/Hat2p. BMC Biol, 5: 38, 2007.

Tang, Y., Luo, J., Zhang, W., and Gu, W. Tip60-dependent acetylation of p53 modulates the decision between cell-cycle arrest and apoptosis. Mol Cell, 24: 827-839, 2006.

Thomas, T. and Thomas, T. J. Polyamines in cell growth and cell death: molecular mechanisms and therapeutic applications. Cell Mol Life Sci 2001; 58:244-58.

Tomlinson, G. E., Chen, T. T., Stastny, V. A., Virmani, A. K., Spillman, M. A., Tonk, V., Blum, J. L., Schneider, N. R., Wistuba, II, Shay, J. W., Minna, J. D., and Gazdar, A. F. (1998) Characterization of a breast cancer cell line derived from a germ-line BRCA1 mutation carrier. Cancer Res 58, 3237-3242.

Turner, N., Tutt, A., and Ashworth, A. (2004) Hallmarks of 'BRCA-ness' in sporadic cancers. Nat Rev Cancer 4, 814-819.

Wolf, M., Bauder-Wust, U., Pipkorn, R., Eskerski, H., and Eisenhut, M. (2006) Fluorophor-labeled spermidine derivatives as fluorescent markers in optical tumor imaging. Bioorg Med Chem Lett 16, 3193-3196.

Wolff, A. C., Armstrong, D. K., Fetting, J. H., et al. A Phase II study of the polyamine analog N1,N11-diethylnorspermine (DENSpm) daily for five days every 21 days in patients with previously treated metastatic breast cancer. Clin Cancer Res 2003; 9:5922-8.

Wurtele, H. and Verreault, A. Histone post-translational modifications and the response to DNA double-strand breaks. Curr Opin Cell Biol, 18: 137-144, 2006.

Yang, X. J. The diverse superfamily of lysine acetyltransferases and their roles in leukemia and other diseases. Nucleic Acids Res, 32: 959-976, 2004.

Zheng, Y., Balasubramanyam, K., Cebrat, M., Buck, D., Guidez, F., Zelent, A., Alani, R. M., and Cole, P. A. Synthesis and evaluation of a potent and selective cell-permeable p300 histone acetyltransferase inhibitor. J Am Chem Soc, 127: 17182-17183, 2005.

Roblot, et al., Regioselective synthesis of inhibitors of histone acetyl transferase covalently linking spermidine to the S-terminus of coenzyme A and fragments, Tetrahedron; vol. 49, No. 29, pp. 6381-6398, 1993.

\* cited by examiner

Figure 1 Mouse tumor models with spd-2a

Figure 2 Mouse tumor model with spd-2a

Figure 3  Mouse tumor model with spd-2a alone

METHODS OF INCREASING THE CYTOTOXICITY OF CHEMOTHERAPEUTIC AGENTS WITH MULTISUBSTRATE INHIBITORS OF HISTONE, PROTEIN-LYS, POLYAMINE ACETYLATION, AND POLYAMINE METABOLISM

PRIOR APPLICATIONS

This application is a continuation of U.S. patent application Ser. No. 13/078,837, filed Apr. 1, 2011, now U.S. Pat. No. 9,107,879, and claims benefit to U.S. patent application 61/320,117, filed Apr. 1, 2010, the contents of which are incorporated herein by reference.

GOVERNMENT SUPPORT

This invention was made with support from the National Institutes of Health Grant Numbers RO1CA111868 and RO1 CA135369. The United States government has rights to this invention.

FIELD OF THE INVENTION

The present invention generally relates to the field of inhibitors of histone acetylation and polyamine metabolism and the treatment of cancer.

Embodiments of the invention generally relate to the field of inhibitors of protein Lys and polyamine acetylation (through KAT or HAT, and SSAT enzymes), and inhibitors of polyamine metabolism, and the treatment of cancer.

BACKGROUND OF THE INVENTION

Post-translational acetylation of the ε-amino groups of specific lysine side-chains in the N-terminal domains (N tails) of the core histones H2A, H2B, H3 and H4 in the chromatin of eukaryotic cells is a central mechanism for regulating chromatin structure and function. The N tails, which protrude from the nucleosome, the fundamental unit of the eukaryotic chromosome, are conformationally variable. They alternate between helical and unstructured segments according to their ionic environment, specifically polyamines, as well as inorganic cations, (Baneres, J. L., Martin, A., and Parello, J. The N tails of histones H3 and H4 adopt a highly structured conformation in the nucleosome. J Mol Biol, 273: 503-508, 1997) and unpublished results, and are capable of forming regulatable contacts with DNA and proteins. By eliminating the positive charges of the lysine side chains, acetylation reduces the interaction of the N tails with DNA, increases DNA accessibility, and promotes the recruitment of transcription factors, DNA polymerases, and DNA repair proteins to chromatin.

The level of acetylation is the result of opposing activities of two families of enzymes, namely the histone acetyl transferases (HATs), which transfer an acetyl group from acetyl coenzyme A (CoA) to the lysine side-chain, and the histone deacetylases (HDACs), which catalyze amide hydrolysis with the release of the acetyl group. These enzymes are now known to interact directly with transcriptional regulators, adding support to the earlier studies linking acetylation to transcription. More recently, histone acetylation has been implicated in the processes of DNA repair, histone deposition after DNA synthesis, and replication fork initiation, and therefore has broad relevance to most chromatin-based activities.

Because the HAT enzymes regulate chromatin structure and function, they are important targets for the development of anti-cancer drugs, but progress in this area has been slow. The first HAT inhibitor to be reported was a multisubstrate adduct, spermidine-CO—$CH_2$—CoA (i.e., Spd-CoA), formed by covalently joining spermidine (Spd) to the S atom of coenzyme A through an acetic acid linkage (Cullis et al. 1982, J Biol Chem 257:12165-9). Spd-CoA was demonstrated to act as an inhibitor of histone and polyamine acetylation under in vitro conditions.

Two isomeric forms of Spd-CoA, i.e., Spd(N1)-CoA and Spd(N8)-CoA, considering the primary amino groups at the N1 or N8 atom of Spd attached to the CoA moiety (inhibitors of the series 1a and 1b, respectively), were subsequently synthesized through a totally regioselective approach and shown to act as HAT inhibitors under in vitro conditions (Parello et al. 1990, C.R.Acad.Sci.Paris, Serie II, 310:1441-1446; Roblot et al., 1993, Tetrahedron 49:6381-6398). This synthetic work opened the path to the synthesis of Spd-CoA analogs in which the coenzyme A was truncated (at the level of the beta-alanine unit, to give series 2a/2b; at the level of the cysteamine unit to give series 3a/3b; we will denote these as Spd-2a/2b and Spd-3a/3b both series in which the polyamine moiety is spermidine or Spd). Similar inhibitors based on a lysine-CoA linkage have been described. Several natural products have also been found to inhibit p300 or PCAF histone acetyltransferase activity, and synthetic analogs have been developed.

Furthermore, HATs are also participating in ε-NH2 (Lys) acetylation of a variety of protein substrates, including, among others, the tumor suppressor p53 (Tang Y, Luo J, Zhang W, Gu W. Mol Cell (2006) 24:827-839, and other non-histone proteins (reviewed in Yang, X. J. The diverse superfamily of lysine acetyltransferases and their roles in leukemia and other diseases, Nucleic Acids Res 2004; 32:959-76). It has been proposed to rename this growing family of ε-NH2 (Lys) acetylating enzymes as KATs thus including all HATs (Allis, C. D., et al, 2007 Cell 131:633-636).

Despite the strong inhibitory activity of the CoA-type inhibitors against histone acetytransferase activity in isolated nuclei or permeabilized cells, or against purified p300/CBP HAT, they exhibit little growth inhibitory activity when used against whole cells, suggesting poor cellular uptake. However, the present inventors have discovered that these inhibitors penetrate the cell and affect a broader range of HAT activities without significantly affecting cell viability. Specific embodiments of the present invention include the multisubstrate histone acetyltransferase inhibitors, Spd-CoA and Spm-CoA, including the spermidine series Spd-1a/1b, Spd-2a/2b, Spd-3a/3b, Spd-4a/4b (in which the primary amino groups at the N1 or N8 atom of Spd are attached to the full or truncated CoA moiety), as well as the spermine series Spm-1, Spm-2, Spm-3, Spm-4 (in which the one of the primary amino groups of Spm is linked to the full or truncated CoA moiety). The present invention shows that these inhibitors are efficiently internalized into whole cells without permeabilization.

Without being bound by theory or mechanism, although inhibitor treatment has little effect on cell viability by itself, it has multiple effects on acetylation-dependent chromatin-associated functions in whole cells and sensitizes tumor cells to a variety of DNA-targeted treatments, including several commonly used chemotherapeutic agents. The inhibitors can also suppress uptake of natural polyamines needed for cell replication and can suppress cancer cell growth by suppressing intracellular polyamine accumulation as well.

The present invention has considerable clinical potential, particularly as a sensitizer to standard chemotherapy and radiation therapy, and as an inhibitor of polyamine metabolism by directly acting on the SSAT enzymes or by synergizing with inhibitors of the polyamine biosynthesis such as DFMO.

SUMMARY OF THE INVENTION

An embodiment of the present invention is a multisubstrate inhibitor of histone acetyltransferase (HAT), denoted Spd-1a, and Spd-1b, comprising Coenzyme A linked to spermidine (Spd) through a thioglycolic acid linkage, similar to the multisubstrate inhibitor previously described by Cullis et al (1982) J Biol. Chem. 257:12165-12169.

Another embodiment of the present invention is further multisubstrate inhibitors of histone acetyltransferase (HAT), denoted Spd-2a, Spd-2b, Spd-3a, Spd-3b, Spd-4a, Spd-4b, Spm-1, Spm-2, Spm-3, Spm-4 according to the following Scheme:

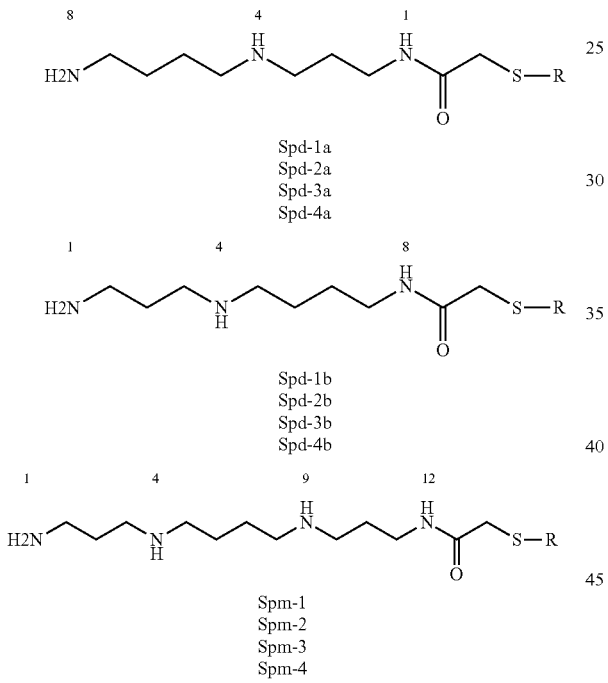

Spermidine (Spd) and spermine (Spm) adducts with coenzyme A (CoA) and CoA fragments as acetyltransferase inhibitors with:

R=CoA for series 1;
R=(CH2)2NH—CO—(CH2)2NH—CO—R2 for series 2 with R2=alkyl, cycloaklyl, aryl, heteroaryl;
R=(CH2)2NH—CO—R3 for series 3 with R3=aliphatic, polycyclic or aromatic group; and
R=(CH2)2NH—CO—(CH2)2NH—CO—R4 for series 4 in which R4=CH(OH)—C(CH3)2-CH2O—CO—R" (in certain embodiments, the configuration of the secondary alcohol corresponds to the natural D(+) series of pantothenic acid) and R"=alkyl, cycloaklyl, aryl, heteroaryl.

Another embodiment of the present invention is further multisubstrate inhibitors of histone acetyltransferase (HAT), in which the polyamine moiety of the inhibitor includes cyclic analogs of spermidine, in which the cyclic component can be a piperazine or homopiperazine (with different degrees of substitution), while the coenzyme moiety is R=(CH2)2NH—CO—(CH2)2NH—CO—R2 for series 2, with R2=alkyl, cycloaklyl, aryl, heteroaryl;
R=(CH2)2NH—CO—R3 for series 3 with R3=aliphatic, polycyclic or aromatic group;
R=(CH2)2NH—CO—(CH2)2NH—CO—R4 for series 4 in which R4=CH(OH)—C(CH3)2-CH2O—CO—R" (in certain embodiments, the configuration of the secondary alcohol corresponds to the natural D(+) series of pantothenic acid) and R"=alkyl, cycloaklyl, aryl, heteroaryl.

Exemplary compounds, grouped under the name of Spd-Homopip-CoA compounds, are listed below:

Another embodiment of the present invention is further multisubstrate inhibitors of histone acetyltransferase (HAT), in which the polyamine moiety of the inhibitor includes cyclic analogs of spermine, in which the cyclic component can be a piperazine or homopiperazine (with different degrees of substitution), wherein the coenzyme moiety is:

R=(CH2)2NH—CO—(CH2)2NH—CO—R2 for series 2, with R2=alkyl, cycloaklyl, aryl, heteroaryl;
R=(CH2)2NH—CO—R3 for series 3, with R3=alkyl, cycloaklyl, aryl, heteroaryl;
R=(CH2)2NH—CO—(CH2)2NH—CO—R4 for series 4, with R4=CH(OH)—C(CH3)2-CH2O—CO—R" (in certain embodiments, the configuration of the secondary alcohol corresponds to the natural D(+) series of pantothenic acid) and R"=alkyl, cycloaklyl, aryl, heteroaryl. Exemplary compounds, grouped under the name of Spm-Homopip-CoA compounds, are listed below:

Another embodiment of the present invention is further multisubstrate inhibitors of histone acetyltransferase (HAT), in which the polyamine moiety of the inhibitor includes cyclic analogs of spermidine, in which the cyclic component can be a piperazine or homopiperazine (with different degrees of substitution), while the coenzyme moiety is R=(CH2)2NH—CO—(CH2)2NH—CO—R2 for series 2, with R2=alkyl, cycloaklyl, aryl, heteroaryl;

R=(CH2)2NH—CO—R3 for series 3 with R3=alkyl, cycloaklyl, aryl, heteroaryl;

R=(CH2)2NH—CO—(CH2)2NH—CO—R4 for series 4 in which R4=CH(OH)—C(CH3)2-CH2O—CO—R" (in certain embodiments, the configuration of the secondary alcohol corresponds to the natural D(+) series of pantothenic acid) and R"=alkyl, cycloaklyl, aryl, heteroaryl.

Exemplary compounds are listed below:

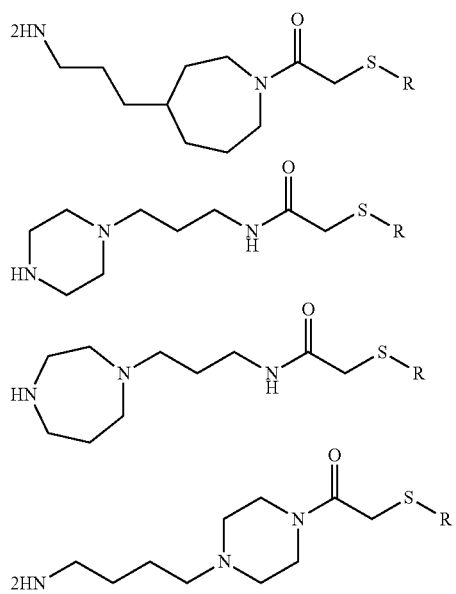

Yet another embodiment of the present invention is further multisubstrate inhibitors of histone acetyltransferase (HAT), in which the polyamine moiety of the inhibitor includes cyclic analogs of spermidine, in which the cyclic component is a 6-membered ring (cyclohexane, piperidine), wherein the coenzyme moiety is:

R=(CH2)2NH—CO—(CH2)2NH—CO—R2 for series 2, with R2=alkyl, cycloaklyl, aryl, heteroaryl;

R=(CH2)2NH—CO—R3 for series 3, with R3=alkyl, cycloaklyl, aryl, heteroaryl;

R=(CH2)2NH—CO—(CH2)2NH—CO—R4 for series 4, with R4=CH(OH)—C(CH3)2-CH2O—CO—R" (in certain embodiments, the configuration of the secondary alcohol corresponds to the natural D(+) series of pantothenic acid) and R"=alkyl, cycloaklyl, aryl, heteroaryl; note that the 1,3-disubstitution on the cyclohexane and piperidine ring is cis while the absolute configuration includes both series R and S.

Exemplary compounds are listed below:

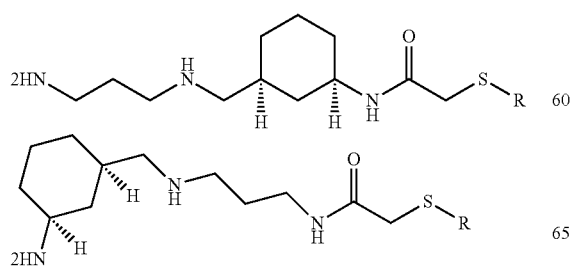

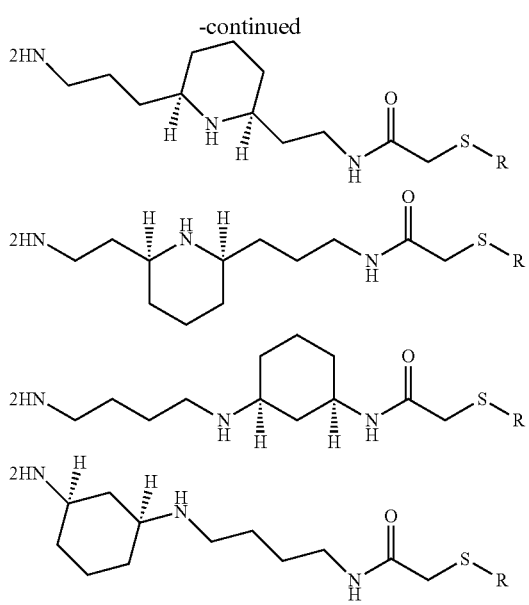

Another embodiment of the present invention is further multisubstrate inhibitors of histone acetyltransferase (HAT), in which the polyamine moiety of the inhibitor includes cyclic analogs of spermine, in which the cyclic component can be a piperazine or homopiperazine (with different degrees of substitution), wherein the coenzyme moiety is:

R=(CH2)2NH—CO—(CH2)2NH—CO—R2 for series 2, with R2=alkyl, cycloaklyl, aryl, heteroaryl;

R=(CH2)2NH—CO—R3 for series 3, with R3=alkyl, cycloaklyl, aryl, heteroaryl;

R=(CH2)2NH—CO—(CH2)2NH—CO—R4 for series 4, with R4=CH(OH)—C(CH3)2-CH2O—CO—R" (in certain embodiments, the configuration of the secondary alcohol corresponds to the natural D(+) series of pantothenic acid) and R"=alkyl, cycloaklyl, aryl, heteroaryl. Exemplary compounds are listed below:

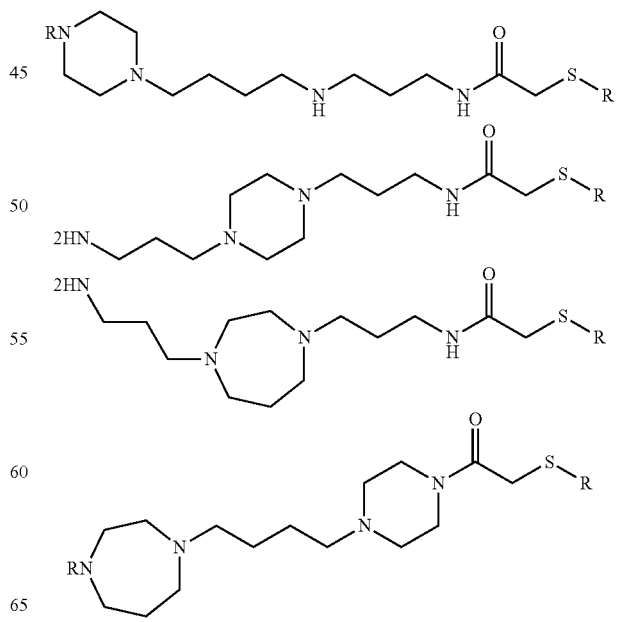

The present inventors found that the compounds 1a, 1b, and 2a had little effect on overall cell viability when added to cultured tumor cells. The failure of multisubstrate HAT inhibitors involving Coenzyme A to affect cell viability has been previously assumed, but not proven, to be due to poor cell penetration as a result of the charged coenzyme A moiety.

Unexpectedly, however, treatment of whole cells with Spd-CoA 1a causes a rapid although transient inhibition of histone acetylation that correlates with a transient arrest of DNA synthesis, a transient delay in S-phase progression, and an inhibition of nucleotide excision repair and DNA double strand break repair. Furthermore, Spd-CoA 1a synergizes strongly with, for example, the DNA-targeted chemotherapeutic drugs, cisplatin (Platinol™) and 5-fluorouracil, and with the DNA damaging drug, camptothecin, and with UVC irradiation. The results demonstrate that Spd-CoA is efficiently internalized into cells, and suggest that the resulting inhibition of acetylation-dependent DNA repair enhances cellular sensitivity to DNA damage. Accordingly, embodiments of the present invention constitute a novel class of potent therapy sensitizers for a broad range of conventional cancer treatments.

For example, the present inventors found that compound 1a inhibits histone acetylation and causes a rapid and reversible arrest of DNA synthesis when added to cells at concentrations comparable to those needed to inhibit purified p300, indicating that it is efficiently internalized. In addition, the present inventors have found that treatment of tumor cells with the 1a and 2a and 3a inhibitors results in a dramatic sensitization to chemotherapy.

Embodiments of the invention are therefore novel in demonstrating: (1) that multisubstrate inhibitors based on CoA are internalized and inhibit histone acetylation in whole cells, and (2) that inhibition of histone acetylation can be used to enhance the efficacy of chemotherapy in cancer cells in culture and in human tumor xenografts in nude mice.

An embodiment of the present invention thus relates to a method of treating cancer in a subject in need thereof, by administering to a subject in need thereof a first amount of a histone acetyl transferase (HAT) inhibitor or a pharmaceutically acceptable salt or hydrate thereof, in a first treatment procedure, and a second amount of an anti-cancer agent in a second treatment procedure. The first and second amounts together comprise a therapeutically effective amount. The effect of the HAT inhibitor and the anti-cancer agent may be additive or synergistic.

Another embodiment of the present invention is a method of treating cancer in a subject in need thereof, comprising administering to the subject a first amount of a HAT inhibitor of the present invention or a pharmaceutically acceptable salt or hydrate thereof, and a second amount of an anti-cancer agent, thereby treating the cancer.

Similarly, as indicated herein, the present inventors found that the analogs 2a and 3a with its coenzyme A truncated moiety parallels the effects of 1a although with increased potency.

Figure 5:
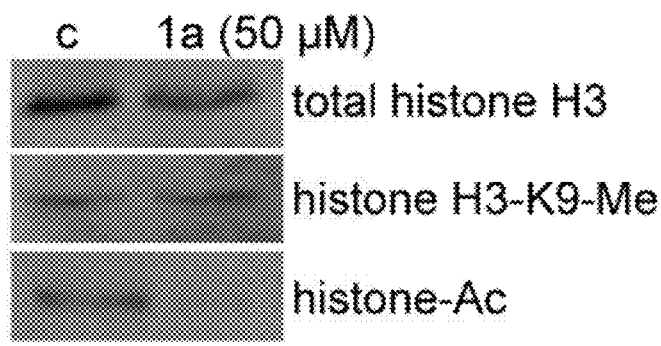

FIG. 5 shows a western analysis of histone H3 K9 acetylation in H358 cells before (left lane) and after (right lane) 18-hr treatment with 50 µM 1a. Each lane represents 175 µg cell lysate protein.

Figure 6:
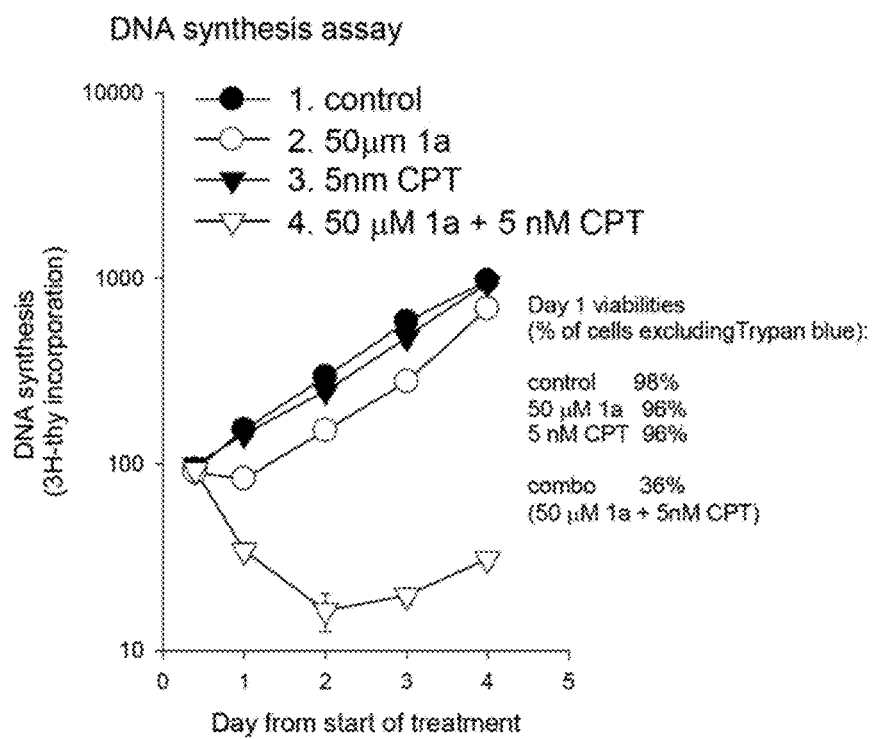

FIG. 6 shows a 96-well assay of [$^3$H]-thymidine incorporation into cells during a 6-hr pulse. Cells were either labeled immediately before treatment (starting DNA synthesis rate), or subjected to the indicated treatments and then pulsed on successive days until day 4. DNA synthesis is represented as the percent of starting DNA synthesis rate. Viability was determined for each treatment condition 24 hours post-start of treatment by the trypan blue exclusion assay, with percentages of viable cells indicated to the right of the graph.

Figure 7:
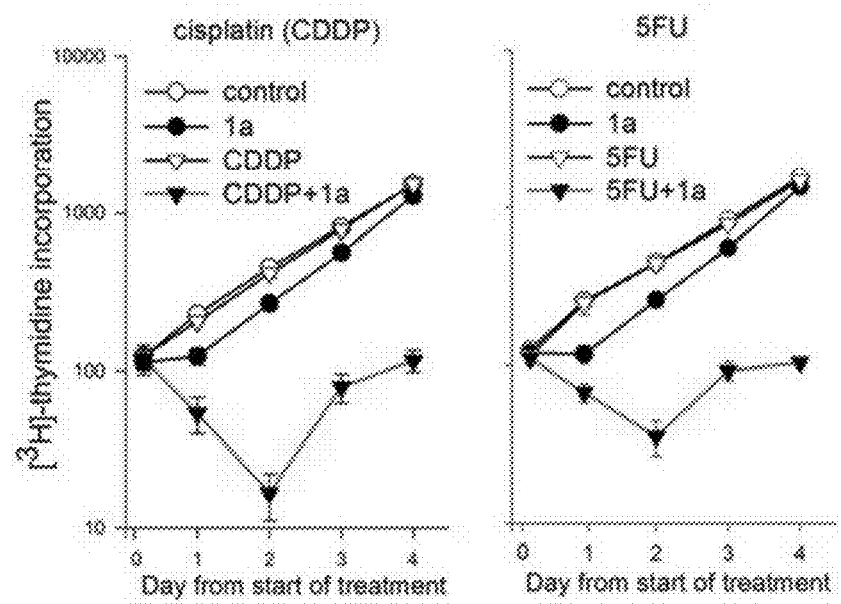

FIG. 7 shows [$^3$H]-thymidine incorporation into DNA of H358 cells carried out as in FIG. 6. Treatment consisted of 1a alone (50 µM), or cisplatin (2 µM, 1 hour, 15 minutes) alone or together with 1a (left panel); or 5-Fluorouracil (5FU, 2 µM, 18 hours) alone or together with 1a (right panel). Symbols are as follows: (-○-) untreated control; (-●-) 50 µM 1a, (-▽-) drug or UVC alone; (-▼-) combination 1a+drug or UVC.

Figure 8:
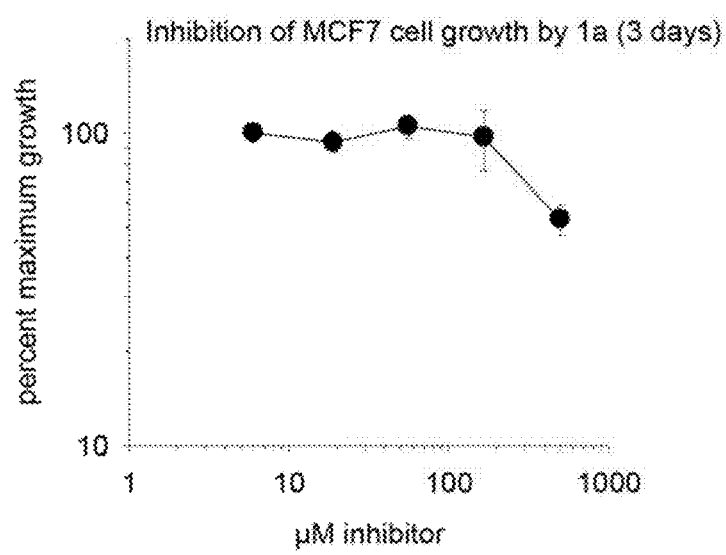

FIG. 8 shows the results of a 96-well viability assay showing the effects of continuous treatment of MCF7 cells with increasing doses of 1a inhibitor. Viability was measured 3 days after the start of treatment and is expressed as a percentage of control (untreated) cell viability.

Figure 9:
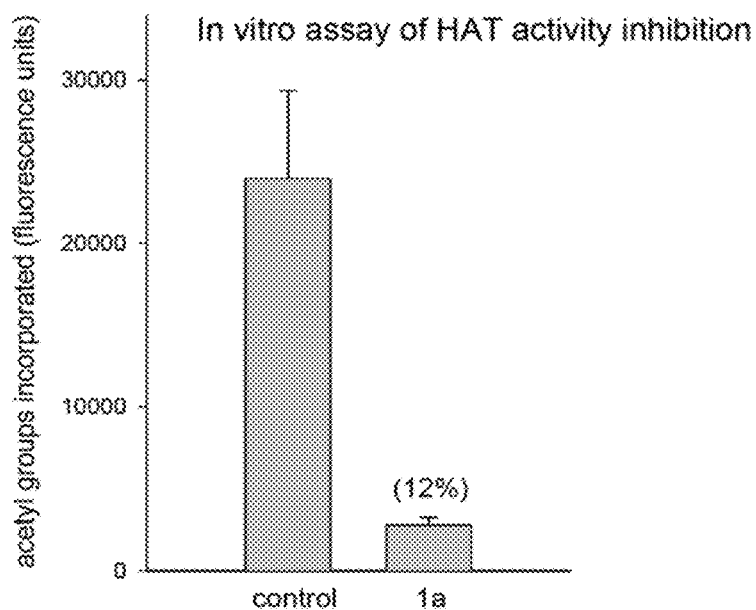

FIG. 9 shows the results of an in vitro assay of HAT activity using an assay kit (ActivMotif). Reactions were set up in duplicate following the protocol supplied by the kit. Bars represent control, no addionts (left), or 50 µM 1a (right). Activity is measured in fluorescence units.

Figure 10:
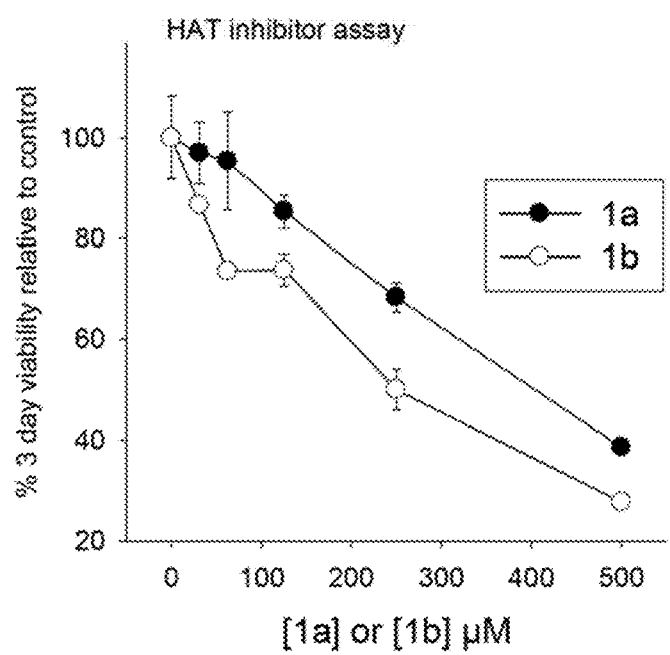

FIG. 10 shows the results of a 96-well cell viability assay showing the effects of repeated treatments of H358 lung cancer cells with increasing doses of 1a or 1b inhibitor. Viability was measured 3 days after the start of treatment and is expressed as a percentage of control (untreated) cell viability. Cells were given fresh inhibitor on the first, second, and third days of treatment and viability was measured on the 4th day (i.e. 3 days post start of treatment).

Figure 11:
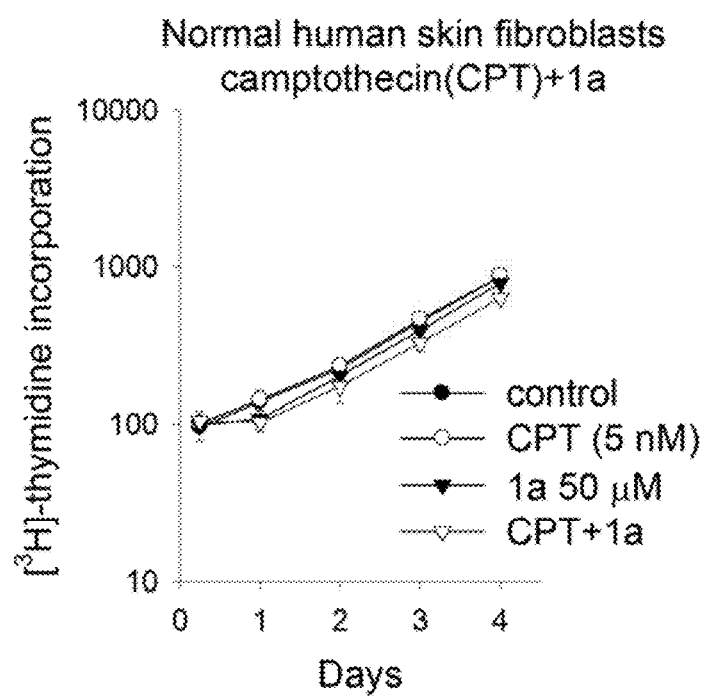

FIG. 11 shows the results of a 96-well assay of [$^3$H]-thymidine incorporation into cells during a 6-hr pulse. Cells were either labeled immediately before treatment (starting DNA synthesis rate), or subjected to the indicated treatments and then pulsed on successive days until day 4. DNA synthesis is represented as the percent of starting DNA synthesis rate.

Figure 12:
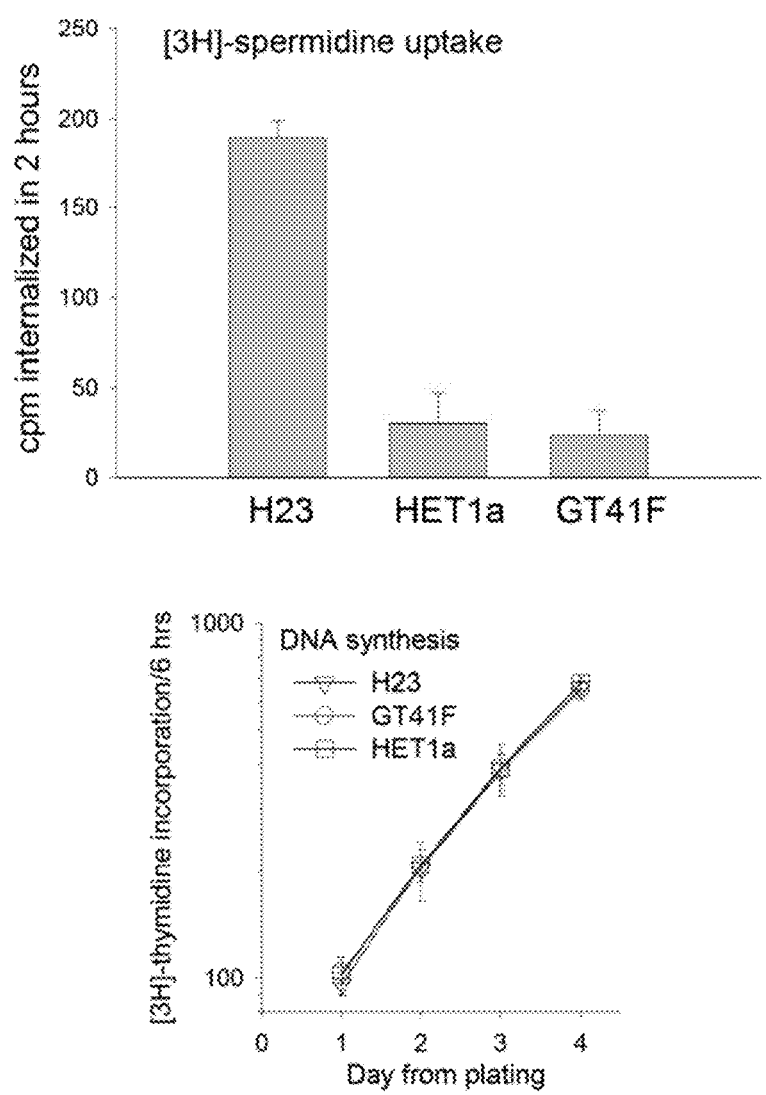

FIG. 12 shows the low spermidine uptake in normal skin fibroblasts compared to tumor cells. (A) Spermidine uptake into H23 lung cancer cells, HET1a immortalized human epithelial cells, and GT41F normal human skin fibroblast cells as assayed according to procedures described in Lopez-Contreras A J, et al (2008) J Biol Chem 283:20761-20769). Cells were plated at 5×105 cells per well in 24-well plates and treated with 2 µM [3H]-spermidine (16.6 Ci/mmol, Perkin Elmer, Boston, Mass.) for two hours. Cells were harvested by trypsinization and subjected to scintillation counting. (B) 96-well assay of incorporation (cpm) into H23, GT41F, and HET1a cells during a 6-hr pulse with 0.5 µCi [3H]-thymidine (NEN, Boston, Mass.) on the indicated days after plating (initial plating 2000 cells per well). Each point represents the result of duplicate wells, with standard deviations shown.

Figure 13:
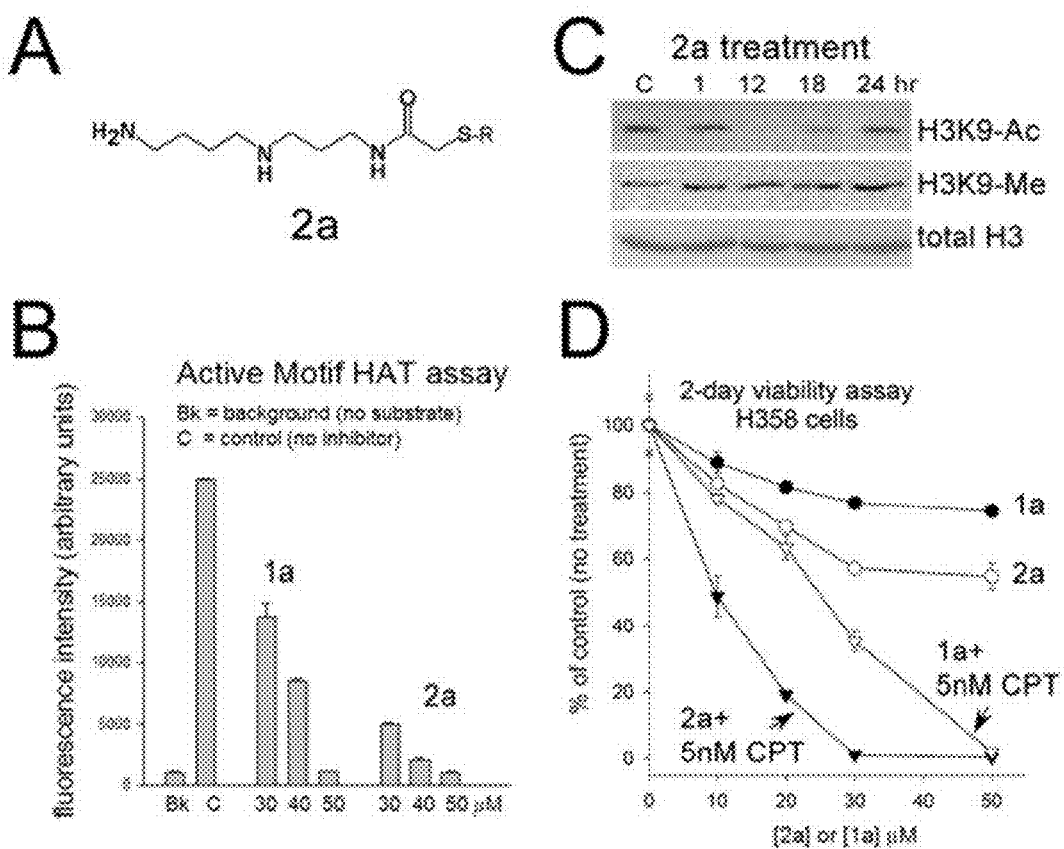

FIG. 13 shows the effects of compound 2a. (A) Structure of compound 2a. (B) In vitro assay of p300 HAT activity using a 96-well assay kit (Active Motif) carried out with 2a at 50 µM, in comparison to 1a. Averages of duplicate samples with standard deviations are shown. (C) Western analysis of histone H3K9 acetylation and methylation, and total histone H3, before ("C", control), or at the indicated times after addition of 50 µM 2a (60 µg lysate/lane). (D) 2-day 96-well viability assay of H358 cells incubated with increasing concentrations of 1a or 2a, +/−5 nM CPT (18 hrs). Fresh medium with 1a and 2a was replaced after removal of CPT.

Figure 14:
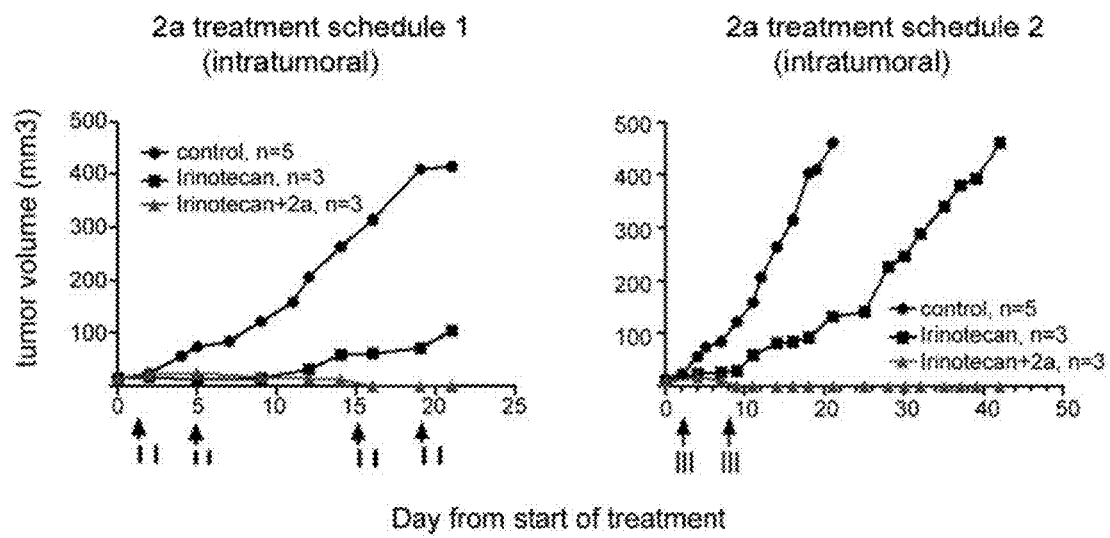

FIG. 14 shows tumor suppression by 2a (intratumoral) plus Irinotecan (intraperitoneal) in a nude mouse model for DU145 prostate cancer. (A) Treatment schedule 1: Tumors were initiated by injecting 10$^6$ DU145 cells (from ATCC) per mouse (4-5 weeks, Harlan Labs) subcutaneously in the flank. When the average tumor size reached about 15 mm$^3$ (5 days post-implantation) animals were administered treatment. Animals in Irinotecan (Camptosar) only group (■) received 40 mg/kg Irinotecan intraperitoneally on days 1, 5, 15, and 19 (indicated by ↑ along x-axis). Animals in Ironotecan+2a group (▲) received 40 mg/kg Irinotecan intraperitoneally on days 2, 6, 16, and 20, and 100 µl of 200 µM 2a administered intratumorally, equivalent to 0.4 mg/kg, on days 1, 2, 5, 6, 15, 16, and 19, 20 (indicated by|along x-axis). Control group (●) received no treatment. Tumors were measured bidirectionally at 2-3 day intervals and volumes were calculated (v=½ L×w$^2$). (B) Treatment schedule 2: Same control group. Animals in Irinotecan (Camptosar) only group received 40 mg/kg Irinotecan intraperitoneally on days 2, 8. Animals in Irinotecan+2a group received 40 mg/kg Irinotecan intraperitoneally on days 2, 8 (9 AM) and 100 µl of 100 µM 2a administered intratumorally, equivalent to 0.2 mg/kg, on days 1 and 7 (5 PM) and days 2 and 8 (9 AM and 5 PM). Tumors were measured bidirectionally and volumes calculated based on the formula volume=½Length×width2.

Figure 1:
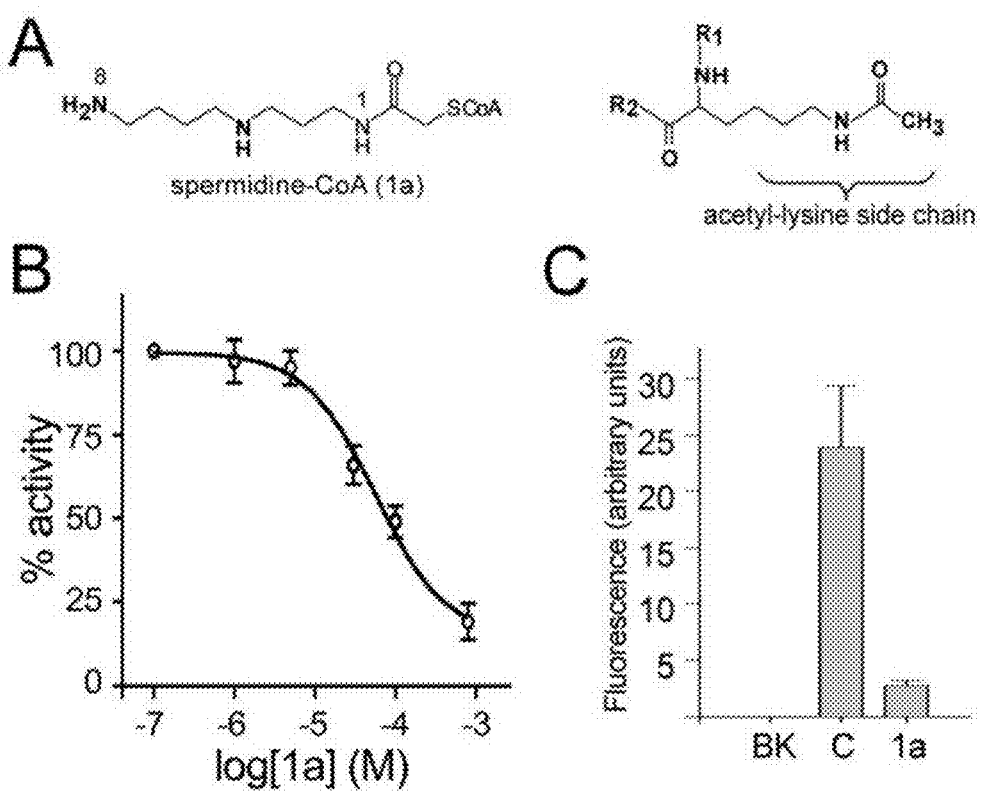
FIG. 1 shows the inhibition of p300/CBP in vitro by the spermidine CoA isomers Spd-1a and Spd-1b. (A) Structures of compound 1a (spermidine CoA), and the acetylated side chain of a lysine residue of a polypeptide chain. (B) Inhibition of p300 acetylating activity as a function of 1a concentration. The catalytic domain of recombinant p300 (1284-1660) was assayed under steady state conditions using an N-terminal acetylated histone H4 peptide substrate, Ac-H4(1-19)-NH2. Closed circles represent experimental data points; plain line represents theoretical profile based on data reduction software (Prism) using a one site inhibition model. (C) In vitro assay of p300 activity using a 96-well assay kit (ActivMotif) and an H3 peptide substrate (5-23), according to manufacturer's instructions. Bars represent average of duplicates. BK=background (no enzyme); C=control (no inhibitor); [1a]=50 μM.
Figure 15:
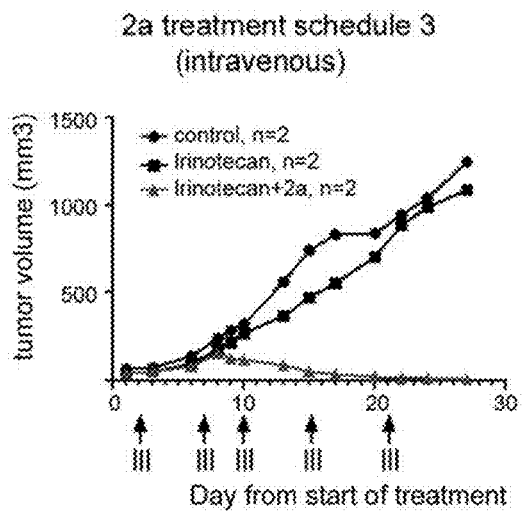

FIG. 15 shows tumor suppression by 2a (intravenous) plus Ironotecan (intraperitoneal) in a nude mouse model for DU145 prostate cancer. Tumors were initiated with 106 DU145 prostate cancer cells injected subcutaneously. When tumors reached an average size of about 50 mm3 (5 days post implantation) animals were administered treatment. Animals in Irinotecan (Camptosar) only group received 40 mg/kg Irinotecan intraperitoneally on days 2, 7, 10, 15, 21. Animals in the Irinotecan+2a group received Irinotecan intraperitoneally on days 2, 7, 10, 15, 21 (9 AM) and 100 µl of 5 mM 2a administered via vein injection, equivalent to 10 mg/kg on days 1, 6, 9, 14, 20 (5 PM) and days 2, 7, 10, 15, 21 (9 AM and 5 PM). Control animals received no treatment. Tumors were measured and volumes calculated as in FIG. 7-1. Symbols and indications are as in FIG. 14.

Figure 16:
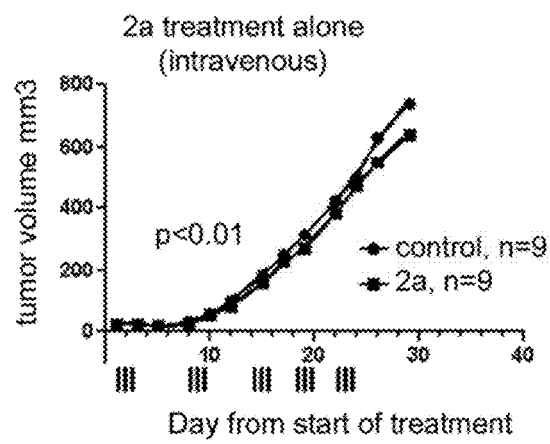

FIG. 16 shows tumor suppression by 2a (intravenous) alone in a nude mouse model for DLD-1 colon cancer. Tumors were initiated By subcutaneous implantation of 10⁶ DLD-1 colon cancer cells. When tumors reached an average size of about 22 mm3 (4 days post-implantation), animals were either left untreated (control, ●, 9 animals) or were treated with 2a alone (■, 9 animals) as follows: 100 µl 5 mM 2a intravenously (equivalent to 10 mg/kg) on days 1, 8, 14, 18, 22 (5 PM) and days 2, 9, 15, 19, 23 (9 AM, 5 PM) as indicated by "|" along the x-axis. Tumors were measured and volumes calculated as in FIG. 14.

Figure 17:
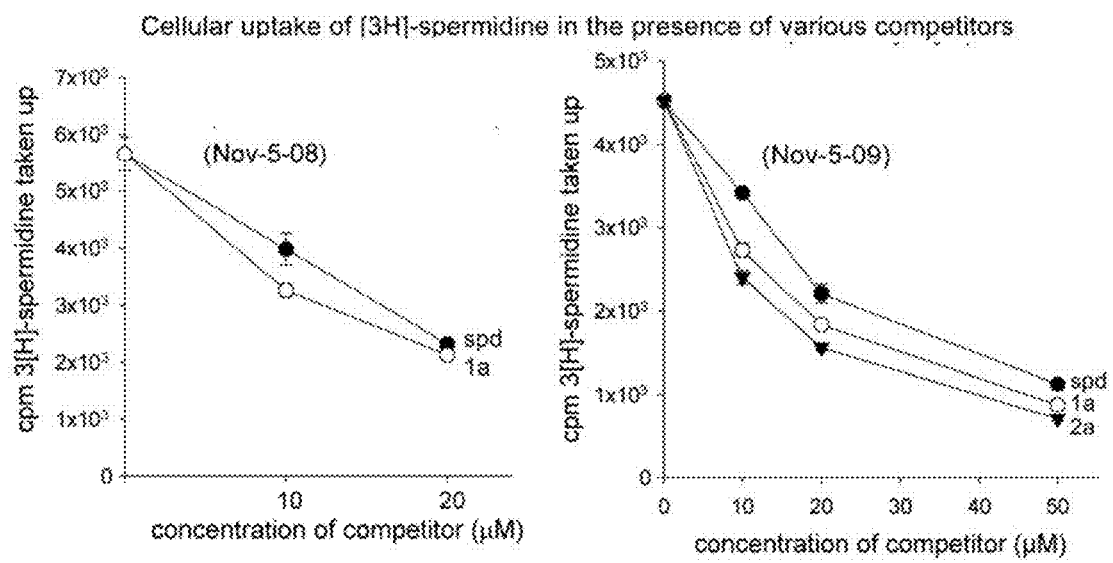

FIG. 17 shows the inhibition of spermidine uptake. Cellular uptake of [$^3$H]spermidine after a 2 hr incubation of H358 lung cancer in the presence of increasing amounts of cold spermidine (●), 1a (○), or 2a (▼). Each point is average of triplicates.

Figure 18:
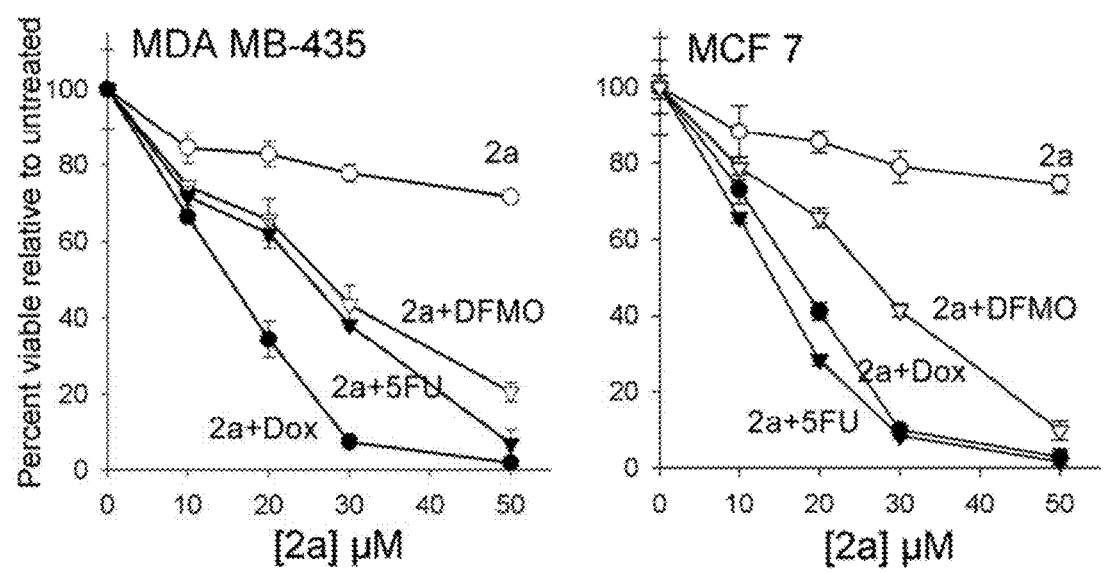

FIG. 18 shows therapy sensitization by 2a. 72 hr viability assays of MDA MB-435 and MCF7 breast cancer cells treated with increasing concentrations of 2a alone (○), or 2a+DFMO (100 µM, ▽), or 2a+5FU (2 µM, 18 hrs, ▼), or 2a+doxorubicin (Dox, adriamycin, 100 nM, 18 hr, ●). Each point is average of triplicates.

Figure 19:
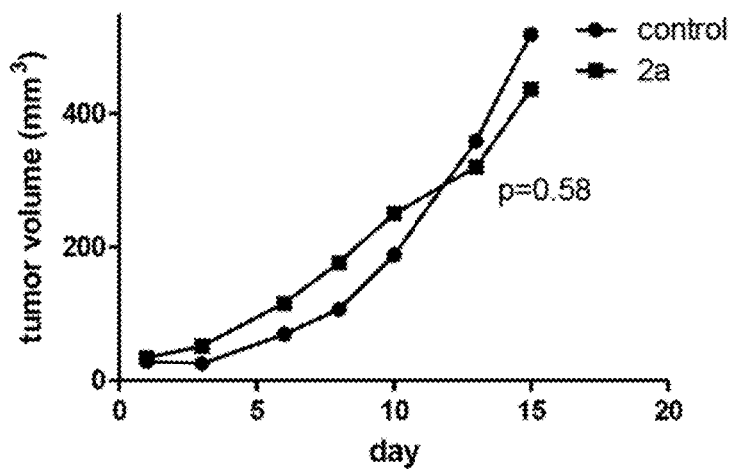
Figure 19:
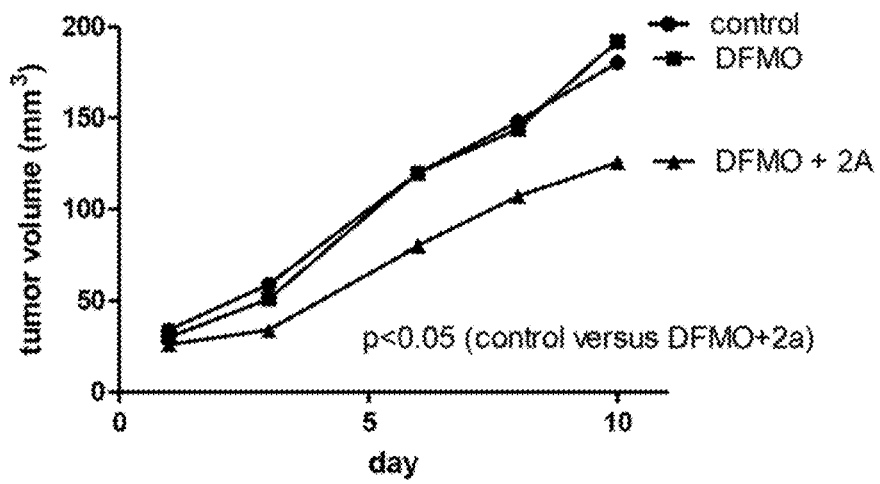

FIG. 19 shows tumor suppression by DFMO+2a. Tumors were initiated by injecting 10⁶ DLD-1 cells (from ATCC) per mouse (female nude mouse, 4-5 weeks, Harlan Labs) subcutaneously in the flank. (A) When the average tumor size reached 26 mm$^3$, animals were randomized into 2 groups (3 per group). One group was left untreated and served as the control (-●-). The other group (-■-) received intratumoral injections of 2a (100 µl of 100 µM, equal to 0.2 mg/kg) on days 1 and 7 (5 PM), and days 2 and 8 (9 AM and 5 PM). Tumors were measured bidirectionally at 2-3 day intervals and tumor volumes were calculated (v=½ Lxw$^2$). A paired t-test was used to evaluate the significance of the differences between the two groups of animals. No significant difference was observed (p=0.58). (B) Tumors were initiated as in part (A). When tumors reached an average size of about 30 mm$^3$, animals were randomized into three groups of 2 animals each. The control group (-●-) received no treatment. The DFMO group (-■-) received intratumoral injections of DFMO (2 mg/kg) on days 1, 7, 9 (5 PM), and 2, 8, 10 (9 AM, 5 PM). The DFMO+2a group (-▲-) received intratumoral injections of DFMO (2 mg/kg)+2a (0.2 mg/kg) on days 1, 7, 9 (5 PM) and 2, 8, 10 (9 AM, 5 PM). Tumors were measured and volumes calculated as in part (A). A paired t-test was used to evaluate the significance of the difference between the curves. The difference between the control and DFMO-only curves was not significant. The difference between the control curve and the DFMO+2a curve was significant (p<0.05).

Figure 20:
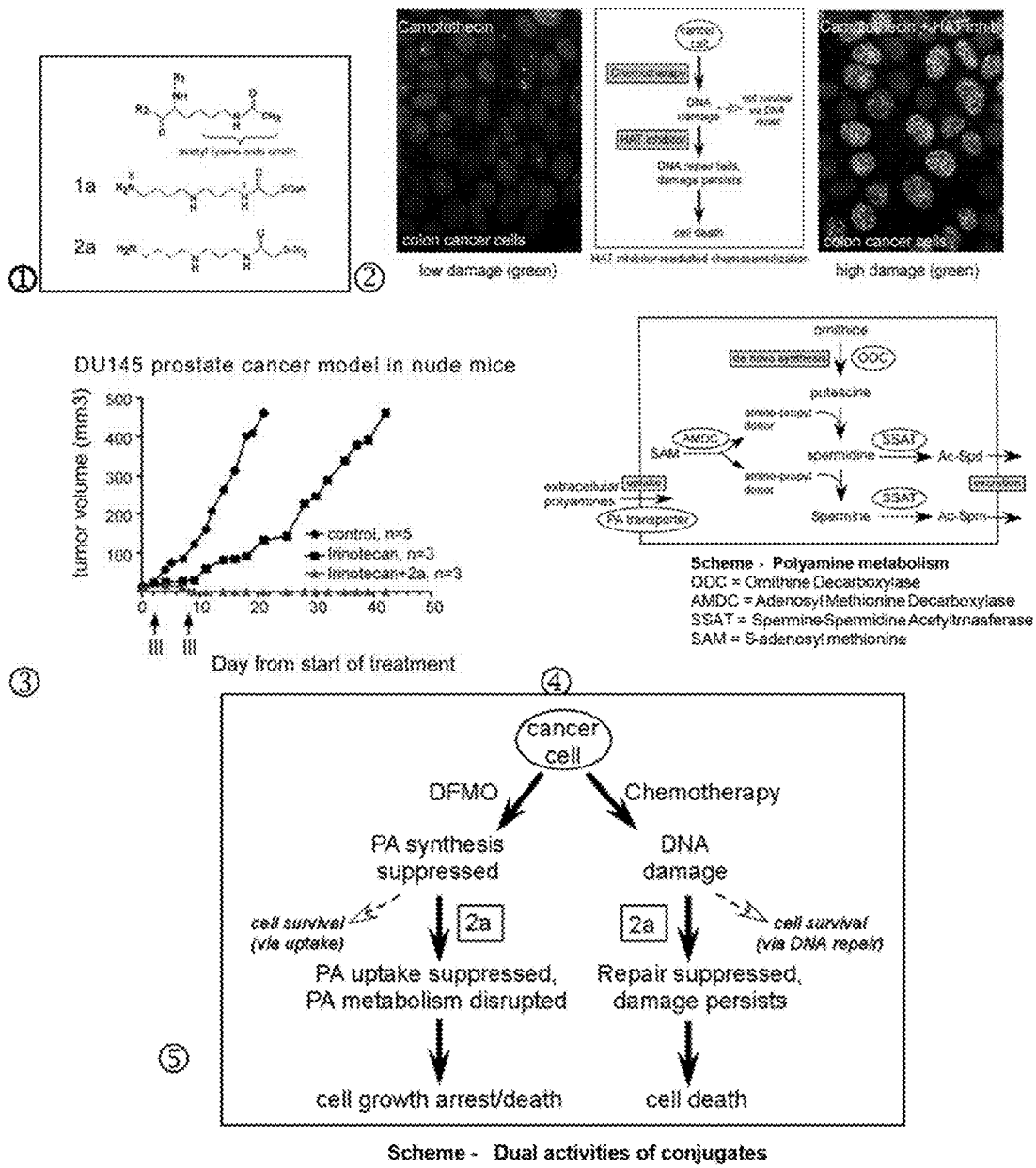

FIG. 20 shows the dual application of the compounds 1a and 2a, and related compounds as chemosensitizers or as co-repressors of polyamine metabolism when used together with DFMO (difluoromethyornithine) or another suppressor of polyamine biosynthesis.

Figure 21:
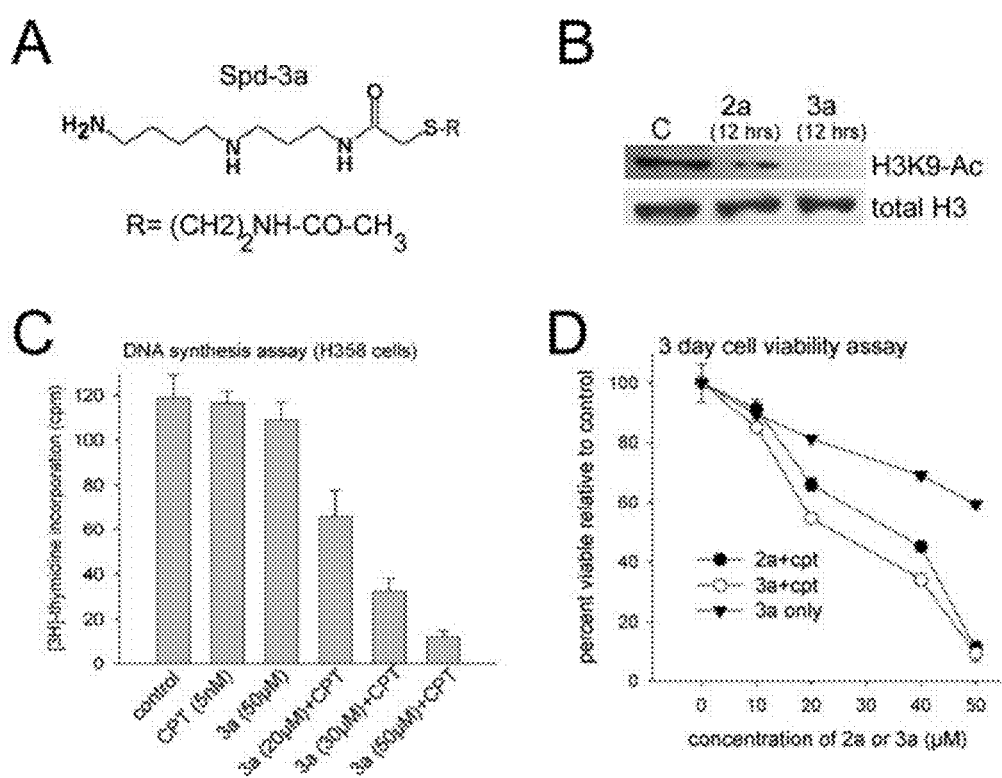

FIG. 21 shows the effects of compound Spd-3a. (A) Structure of Spd-3a. (B) Western analysis of histone H3K9-acetylation and total histone H3, measured in control, untreated H358 lung cancer cells "C" or in H358 cells incubated 12 hours in the presence of 50 µM Spd-2a or Spd-3a. Each lane represents 60 µg cellular protein. (C) [3H]-thymidine incorporation (counts per minute) into DNA of H358 cells during a 6 hour pulse beginning at 42 hours post-start of treatment. Treatments were as follows (bars 1-6 left to right): (1) control: no treatment; (2) CPT alone: 5 nM 18 hours; (3) 3a alone: 50 µM; (4-6) 3a+CPT: CPT (5 nm, 18 hours)+3a at indicated dose. After 18 hours, CPT was removed and medium was replaced with fresh medium containing Spd-3a at the indicated dose. Each bar represents the average of triplicates. (D) 3-day 96-well viability assay of H358 cells grown in the presence of increasing amounts of Spd-2a or Spd-3a, with or without CPT (5 nM 18 hours). Cell viability, measured by the MTS assay, is represented as a percentage of control, untreated cell viability (i.e., no CPT, no Spd-2a or Spd-3a). Each data point represents the average of three wells. The labeling Spd-2a or 2a, and Spd-3a or 3a, is used indifferently.

Figure 22:
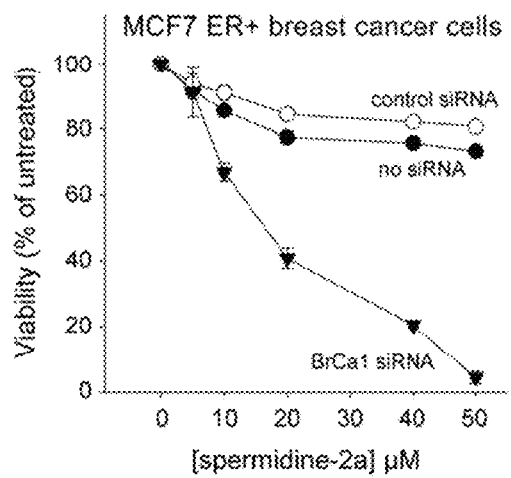
Figure 22:
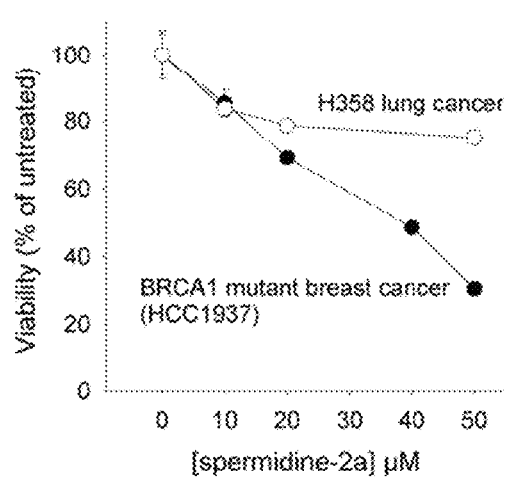
Figure 22:
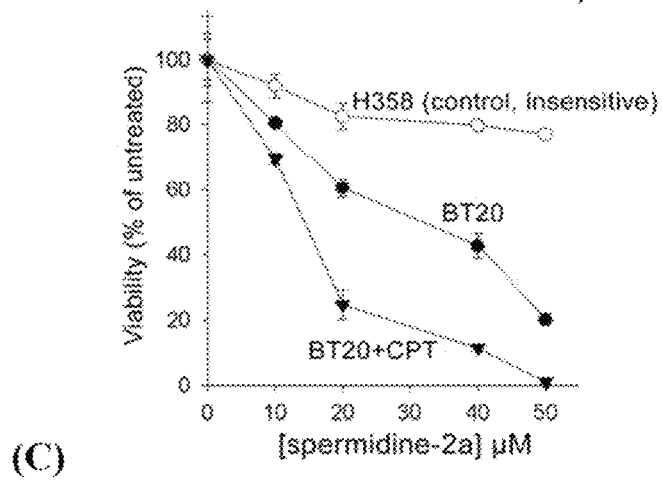

FIG. 22 shows the results for 3-day viability assays showing that BrCa1 suppression or mutation sensitizes to spd-2a treatment and that sporadic TNBC is also hypersensitive to spd-2a. (A) MCF7 ER+ breast cancer cells (BrCa1 wild-type) were left untreated (-○-), or were treated with control siRNA (-●-) or BrCa1 siRNA (-▼-), followed by treatment with increasing doses of spd-2a. Date of exp: Jul. 17, 2010; located p.21 in Hat notebook: KB-2 (2010-2011). (B) H358 lung cancer cells (-○-) and HCC1927 breast cancer cells (-●-, BrCa1 mutant) were treated with increasing doses of spd-2a. Date of exp: Sep. 23, 2010; located on p.25 in Hat notebook: KB-2 (2010-2011), (C) H358 lung cancer cells (control, resistant to spd-2a as a single agent, (-○-), BT20 TNBC cells (-●-), or BT20 cells treated 18 hours with sublethal dose (5 nM) of camptothecin "CPT" (-▼-) were treated with increasing doses of spd-2a. Viability was scored 3 days later. Data points are averages of triplicates.

Figure 23:
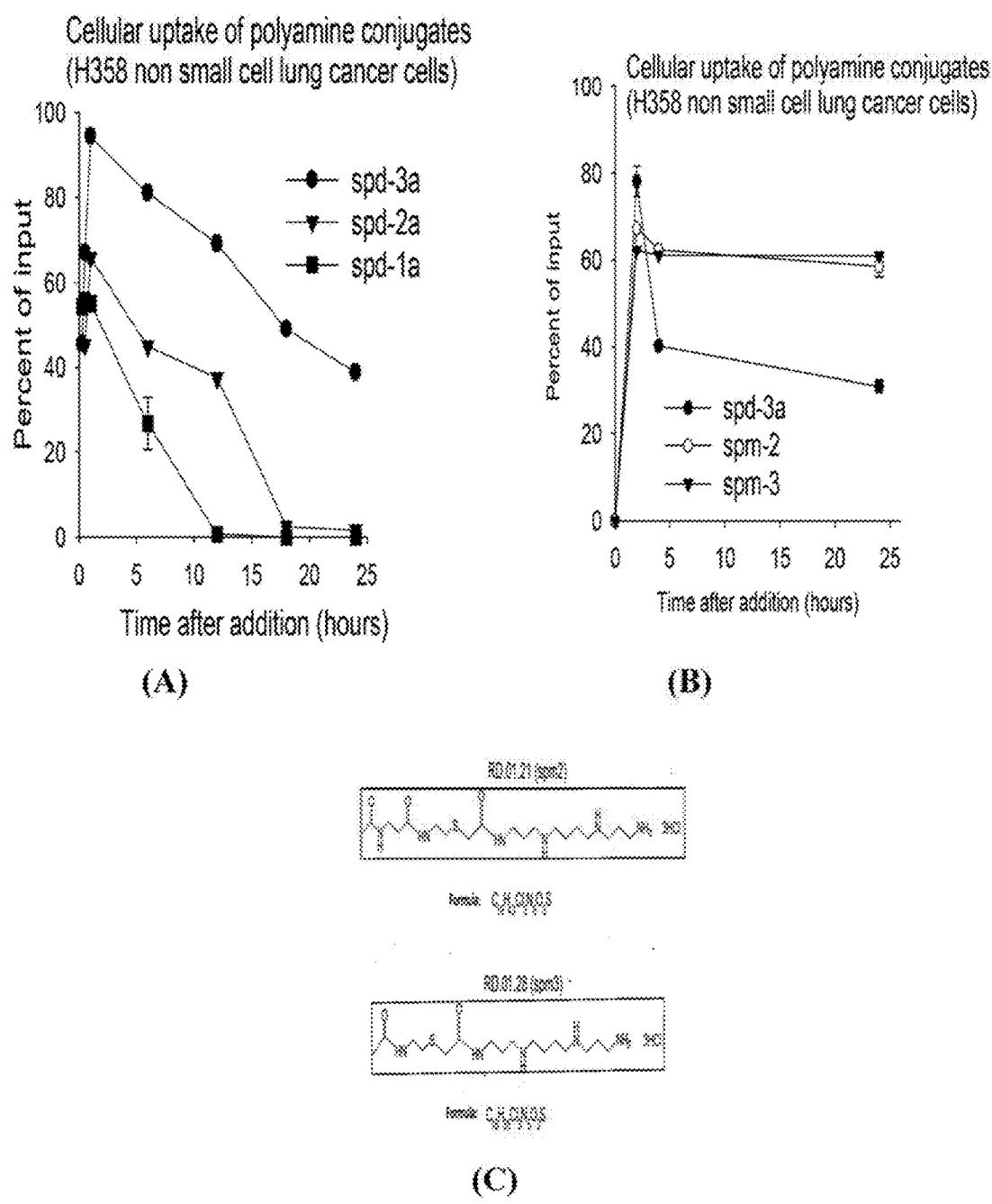

FIG. 23 shows the cellular uptake of spd-1a, spd-2a, spd-3a, spm-2 and spm-3 into H358 non small cell lung cancer cells. Methods: 8000 H358 cells were plated in 24 well plates to achieve 80% confluency. The next day, cells were treated with 50 µm of the indicated compounds at 37° C. in a 10% CO2 incubator for 2 hrs. After that the cells were washed twice with cold PBS and trypsinized and harvested. The cell pellets were washed twice in PBS and the cells were lysed by adding 250 µl water. The lysed cell pellets were made 10% in TCA and kept on ice for 30 minutes to allow the protein to precipitate. The supernatants were extracted 5 times with an equal volume of water saturated ethyl acetate to remove excess TCA. The remaining aqueous phase was concentrated to 2 µl using speed vac. The readings of samples were taken at 206 nm using nanodrop machine from GE Health care. To determine the reading for total input, we set up a control where the conjugate solutions were incubated in the wells of the 24 well plate without cells, followed by a similar extraction procedure method. (A) Uptake experiment of spd-1a, spd-2a, spd-3a. (C) Diagram showing structures of spm2 and spm3.

Figure 24:
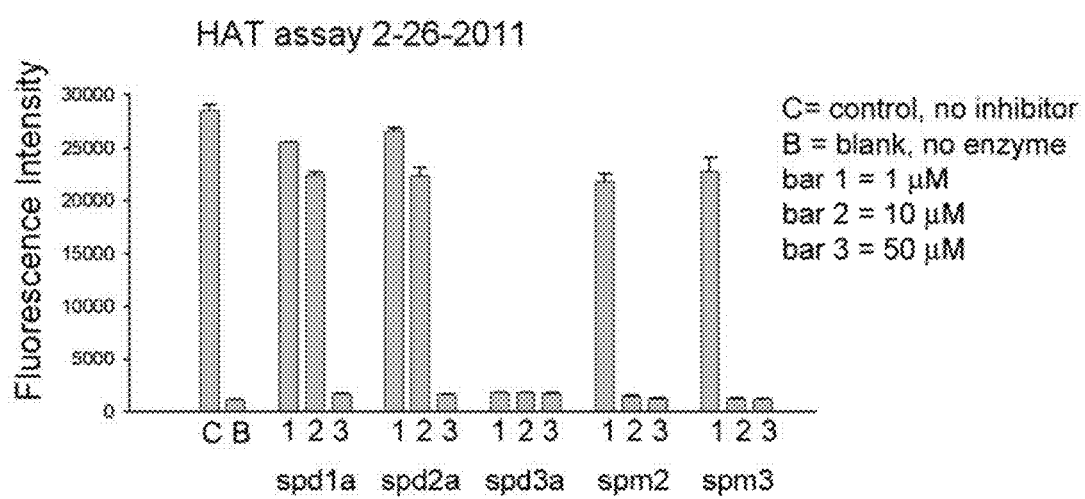

FIG. 24 shows the results of an in vitro assay of inhibition of p300 HAT activity. Assays were performed in duplicate using a HAT assays kit (Active Motif, Carlsbad, Calif.), which provides an H3 peptide substrate (Ac-H3(5-23)-NH2, as communicated by the vendor) and the catalytic domain of p300(965-1810). Cntr=p300 alone.

Figure 25:
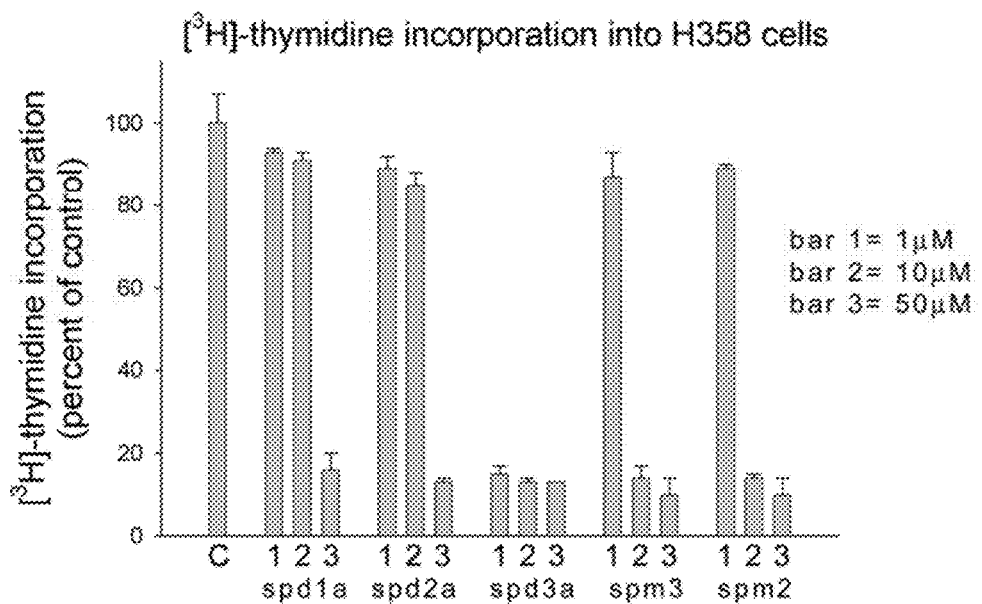

FIG. 25 shows the results of a [$^3$H]-thymidine incorporation (DNA synthesis) assay. H358 cells (2,000/well) in 96-well plates were treated with 1, 10 or 50 µM of spd-1a, spd-2a, spd-3a, spm3, or spm2 for 12 hours. Triplicate wells of cells were pulsed 6 hours with 0.5 µCi [$^3$H]-thymidine (NEN, Boston Mass.) post-start of drug treatment, and harvested onto filter paper using a Brandel Harvester and subjected to scintillation counting. Untreated cells were pulsed from 0-6 hrs to establish the initial rate of incorporation.

Figure 26:
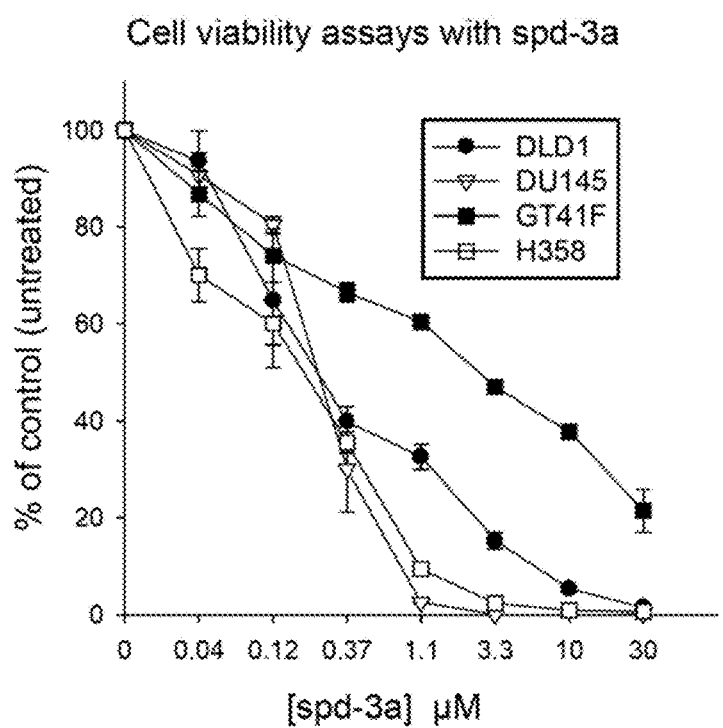

FIG. 26 shows the results of a 96-well viability assays of DLD-1 colon cancer cells, H23 non small cell lung cancer cells, DU145 colon cancer cells, GT41F skin fibroblasts, H358 non small cell lung cancer cells. Cells were plated in 96-well plates at 2000 cells per well and treated with the indicated doses of spd-3a. Cell viability was measured by the MTS assay 3 days later.

Figure 27:
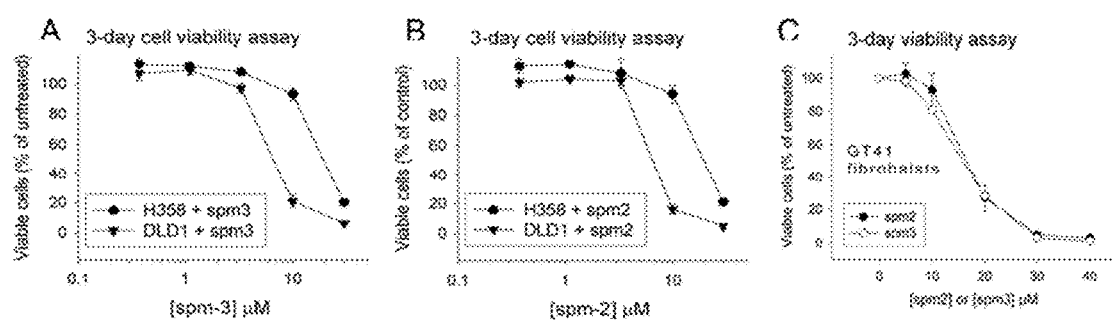

FIG. 27 shows the results of a 96-well viability assays of DLD-1 colon cancer cells, H358 non small cell lung cancer cells, and GT41 fibroblasts treated with spm-2 or spm-3. DLD-1 cells or H358 cells were plated in 96-well plates at 2000 cells per well and treated with the indicated doses of (A) spm-3 or (B) spm-2. (C) Cell viability was measured by the MTS assay 3 days later. Similar experiment using GT41 fibroblasts with spm2 or spm 3. Each assay point represents an average of duplicates.

Figure 28:
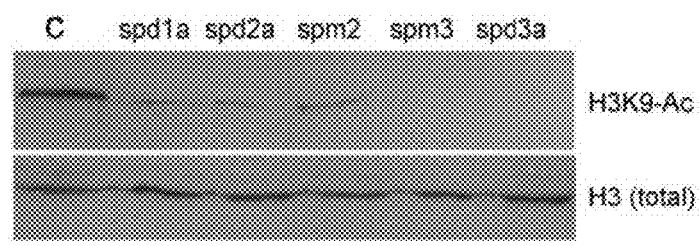

FIG. 28 shows a western blot of acetylated lysine K9 in H358 cells at 12 hours post-treatment with 50 µM spd-1a, spd-2a, spm-2, spm-3, or spd-3a. One 6 cm culture dish of H358 cells per treatment was used. Cells were treated with 50 µM spm-2, spm-3, or spd-3a for 12 hours. Histones were extracted from cells in 0.2M H2SO4 (as described in Furuta, T., et al (2003) J. Biol. Chem. 278: 20303-20312), followed by SDS-PAGE and Western blotting. Blots were probed with anti-acetyl histone H3-lysine 9 (Upstate Biotechnology, Inc.)

DESCRIPTION OF THE INVENTION

As stated above, the present invention generally relates to the field of inhibitors of histone acetylation and the treatment of cancer.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder, particularly cancer. The term "patient" includes human and veterinary subjects.

As used herein, the term "treatment" refers to the medical management of a patient with the intent to cure, ameliorate, stabilize, or prevent a disease, pathological condition, or disorder, particularly cancer. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic).

Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Figure 2:
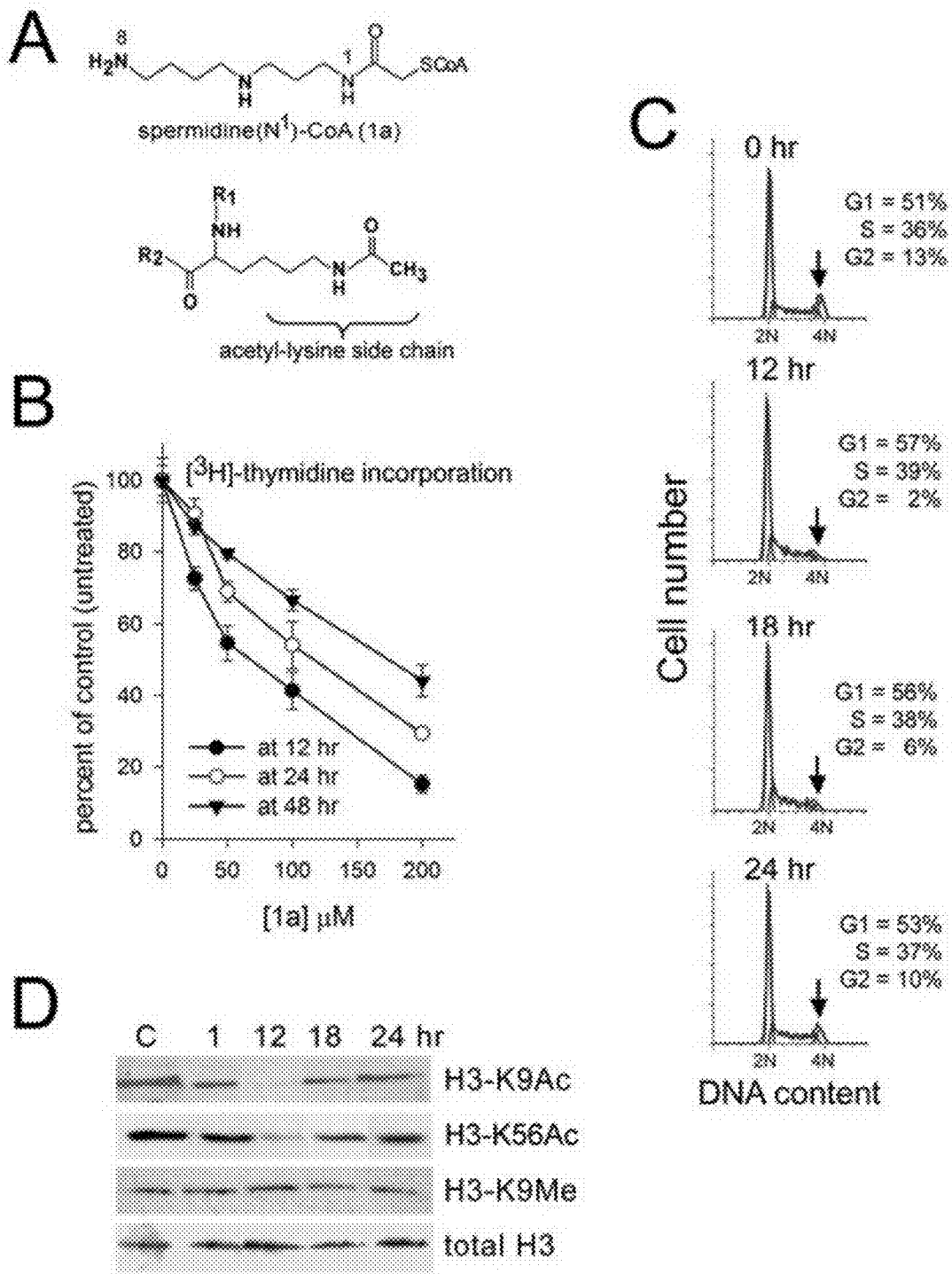
FIG. 2 shows inhibition of DNA synthesis, S-phase progression, and histone acetylation in vivo by 1a. (A) Structures of 1a, and the acetylated side chain of a lysine residue within the polypeptide chain of a protein targeted by the acetylating enzyme ($R_1$ and $R_2$ are the main chain elements on both sides of the lysyl residue). (B) [$^3$H]-thymidine incorporation into DNA of H358 cells pulsed for 6 hrs at three different time points after the addition of increasing concentrations of 1a, i.e., at 6-12 hrs (12 hr curve), at 18-24 hours (24 hr curve), or at 42-48 hrs (48 hr curve). Incorporation is represented as a percentage relative to control (untreated) cells. (C) Cell cycle analysis of propidium iodide-stained cells harvested at various times after addition of 50 μM 1a. % of cells in G1, S, and G2 represents the average of two independent profiles. (D) Western analysis of histone H3 lysine 9 acetylation, histone H3 lysine 56 acetylation, histone H3 lysine 9 methylation, and total histone H3, before "c" or at the indicated times after addition of 50 μM 1a. Each lane represents 60 μg cellular protein.

A "synergistic therapeutic cytotoxic effect," as used herein, means that the combination of at least 2 compounds suppresses cell viability or DNA synthesis to an extent greater than the sum of the suppressive effects of the two agents used individually, where cell viability or DNA synthesis is measured by a standard viability assays or DNA synthesis assays as described for FIG. 2. Alternatively, a "synergistic therapeutic cytotoxic effect," as used herein means that a given combination of at least 2 compounds exhibits synergy when tested in a cytotoxic assay (see Assays for Testing the Anticancer Synergistic Activity of a Combination of an Antineoplastic Thiol-binding Mitochondrial Oxidant and a Second Antineoplastic Agent, below). Synergy is assessed using the median-effect principle (Chou, et al., Adv Enzyme Regul 22:27-55 (1984)). This method is based on Michaelis-Menten kinetics and reduces combination effects to a numeric indicator, the combination index (C.I.). Where the combination index is less than 1, synergism is indicated. Where the combination index is equal to 1, summation (also commonly referred to as additivity) is indicated. Where the combination index is greater than 1, antagonism is indicated.

The terms "subject" or "patient" are art-recognized, and as used herein, refer to a mammal, including dog, cat, rat, mouse, monkey, cow, horse, goat, sheep, pig, camel, and, most preferably, a human. In preferred embodiments, a subject is a subject in need of treatment. In certain embodiments, the subject can be a normal subject, e.g., a subject having no known or diagnosed abnormal cells, e.g., a cancer-free subject. In other embodiments, the subject has a known, diagnosed, or suspected disorder, i.e., a cell proliferative disorder such as a benign or malignant tumor, including cancer, e.g., a solid or liquid tumor.

The treatment procedures can take place sequentially in any order, simultaneously or a combination thereof. For example, the first treatment procedure, administration of an HAT inhibitor, can take place prior to the second treatment procedure, i.e. the anti-cancer agent, after the second treatment with the anticancer agent, at the same time as the second treatment with the anticancer agent, or a combination thereof. For example, a total treatment period can be decided for the HAT inhibitor. The anti-cancer agent can be administered prior to onset of treatment with the HAT inhibitor or following treatment with the HAT inhibitor. In addition, treatment with the anti-cancer agent can be administered during the period of HAT inhibitor administration but does not need to occur over the entire HAT inhibitor treatment period. Similarly, treatment with the HAT inhibitor can be administered during the period of anti-cancer agent administration but does not need to occur over the entire anti-cancer agent treatment period. In another embodiment, the treatment regimen includes pre-treatment with one agent, either the HAT inhibitor or the anti-cancer agent, followed by the addition of the second agent for the duration of the treatment period.

Additionally, compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer) and the health of the patient should preferably be closely monitored during and for a reasonable period after treatment.

As one example, a general guide that can be used to determine initial dosing ranges for HAT inhibitors can be based on an anticipation of minimal toxicities of inhibitors in vivo, as circulating levels of spermidine in rodents can exceed 40 $\mu$M during lactation (see Lundgren, D. W. and Oka, T. Alterations in polyamine levels in rat blood during pregnancy and lactation. Am J Physiol 1978; 234:E451-6), and alkylated spermine analogues have displayed only mild host toxicity in rodents, with maximal tolerated doses as a single intraperitoneal injection to be greater than 400 mg/kg (see Bernacki, R. J., Oberman, E. J., Seweryniak, K. E., et al. Preclinical antitumor efficacy of the polyamine analogue N1,N11-diethylnorspermine administered by multiple injection or continuous infusion. Clin Cancer Res 1995; 1:847-57), equivalent to about 16 mM maximal blood concentration (MW in the range of 250 g/mol). In humans, blood spermidine concentrations ranging from 4-14 $\mu$M have been reported (see Soda, K., Kano, Y., Nakamura, T., et al. Spermine, a natural polyamine, suppresses LFA-1 expression on human lymphocyte. J Immunol 2005; 175:237-45).

Further, the following is a general calculation to estimate the starting point for determining a human dose of 2a:

molecular weight of 2a≅450 g/mole

50 $\mu$M 2a=(50 $\mu$moles/liter)×(450 $\mu$g/$\mu$mole)=22,500 $\mu$g/liter=22.5 mg/liter.

22.5 mg/liter×5.6 liters (average human blood volume)=126 mg/injection.

126 mgs/70 kg (average adult size)=1.8 mg/kg.

However, of course it is well understood that one of ordinary skill in the art would recognize that the preferred dose for administration for a compound of the present invention will vary greatly depending on the nature of the indication and the condition of a patient.

The term "effective amount" is art-recognized, and as used herein, refers to an amount effective to achieve a desired result, such as preventing, treating, ameliorating, or curing. When the term "effective amount" is used in reference to one or more components of a combination therapy, the amount is an amount effective when employed in combination with such other component or components.

Thus, embodiments of the present invention relates to a method of treating cancer in a subject in need thereof, by administering to a subject in need thereof a first amount of a HAT inhibitor or a pharmaceutically acceptable salt or hydrate thereof, in a first treatment procedure, and a second amount of an anti-cancer agent in a second treatment procedure, wherein the first and second amounts together comprise a therapeutically effective amount.

Treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

The term "coenzyme A" or "CoA" biosynthetic enzyme includes any enzyme utilized in the formation of a compound (e.g., intermediate or product) of the CoA biosynthetic pathway, in includes the following compound, and analogs thereof:

As discussed above, the methods of the present invention are useful in the treatment in a wide variety of cancers, including but not limited to solid tumors, hematological malignancies, carcinomas, neuroblastoma, or melanoma.

The method comprises administering to a patient in need thereof a first amount of an HAT inhibitor, e.g., compounds 1a, 2a, 3a or analogs thereof (see Scheme 1), in a first treatment procedure, and a second amount of an anti-cancer agent in a second treatment procedure. The first and second treatments together comprise a therapeutically effective amount.

The invention further relates to pharmaceutical combinations useful for the treatment of cancer. The pharmaceutical combination comprises a first amount of an HAT inhibitor, e.g., compound 1a, 2a, 3a or analogs thereof (see Scheme 1) and a second amount of an anti-cancer agent. The first and second amounts together comprise a therapeutically effective amount.

The invention further relates to the use of a first amount of an HAT inhibitor and a second amount of an anti-cancer agent for the manufacture of a medicament for treating cancer.

In particular embodiments of this invention, the combination of the HAT inhibitor and anti-cancer agent is additive, i.e. the combination treatment regimen produces a result that is the additive effect of each constituent when it is administered alone. In accordance with this embodiment, the amount of HAT inhibitor and the amount of the anti-cancer together constitute an effective amount to treat cancer.

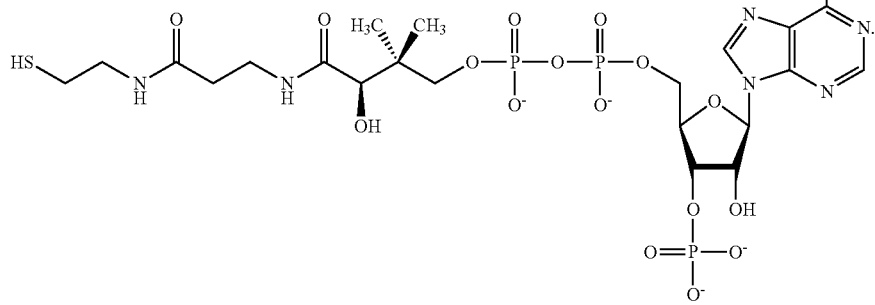

The term "spermidine", as used herein, refers to the polyamines, including those such as $H_2N—(CH_2)_3—NH(CH_2)_4—NH_2$, and analogs thereof. Such analogs include "spermine." The term includes compounds which are structurally related to spermidine, but which are substantially not metabolized in vivo, including, but not limited to, (1-methylspermidine) $H_2N—CH(CH_3)—(CH_2)_2—NH(CH_2)_4—NH_2$. Such metabolically stable analogues may include spermidine analogues which are not substantially susceptible to enzymes that metabolize polyamines.

Thus, metabolically stable analogues of spermidine include, for example, polyamine hydrocarbon compounds (i.e., hydrocarbon compounds which contain two or more substituted or unsubstituted amino groups). Preferably, the metabolically stable analogues of spermidine are alkylated analogues of spermidine (i.e., spermidine and structurally related compounds which are substituted with one or more alkyl groups).

If there are any, conflicting definitions herein, all expressed definitions apply.

In another particular embodiment of this invention, the combination of the HAT inhibitor and anti-cancer agent is considered therapeutically synergistic when the combination treatment regimen produces a significantly better anticancer result (e.g., cell growth arrest, apoptosis, induction of differentiation, cell death) than the additive effects of each constituent when it is administered alone at a therapeutic dose. Standard statistical analysis can be employed to determine when the results are significantly better. For example, a Mann-Whitney Test or some other generally accepted statistical analysis can be employed.

The treatment procedures can take place sequentially in any order, simultaneously or a combination thereof. For example, the first treatment procedure, administration of an HAT inhibitor, can take place prior to the second treatment procedure, i.e. the anti-cancer agent, after the second treatment with the anticancer agent, at the same time as the second treatment with the anticancer agent, or a combination thereof. For example, a total treatment period can be decided for the HAT inhibitor. The anti-cancer agent can be administered prior to onset of treatment with the HAT inhibitor or following treatment with the HAT inhibitor. In addition, treatment with the anti-cancer agent can be administered during the period of HAT inhibitor administration but does not need to occur over the entire HAT inhibitor treatment The inhibitor is designed to resemble a potential reaction product, shown below, in the HAT-mediated reaction that results in a transfer of an acetyl group from acetyl coenzyme A to the epsilon amino group of lysine:

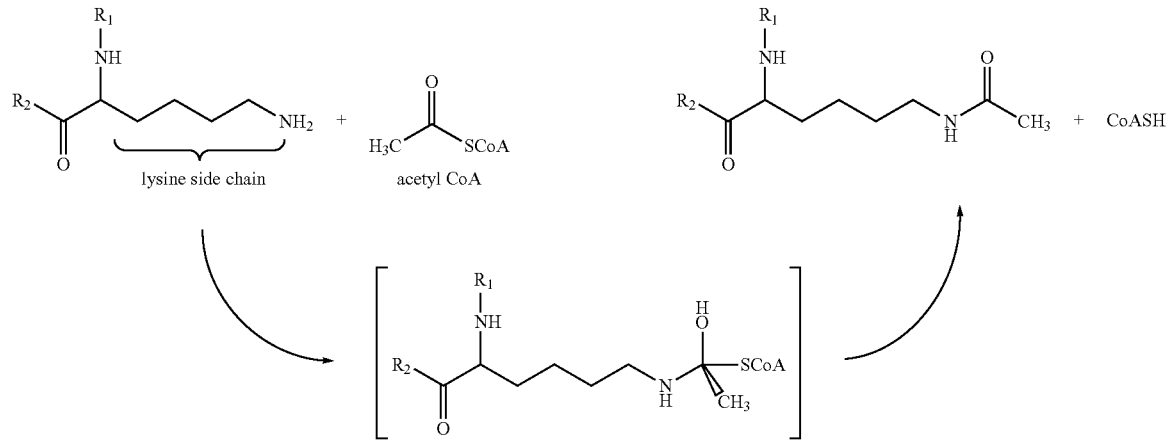

period. Similarly, treatment with the HAT inhibitor can be administered during the period of anti-cancer agent administration but does not need to occur over the entire anti-cancer agent treatment period. In another embodiment, the treatment regimen includes pre-treatment with one agent, either the HAT inhibitor or the anti-cancer agent, followed by the addition of the second agent for the duration of the treatment period.

In one particular embodiment of the present invention, the HAT inhibitor can be administered in combination with any one or more of an additional HAT inhibitor, an alkylating agent, an antibiotic agent, an antimetabolic agent, a hormonal agent, a plant-derived agent, an anti-angiogenic agent, a differentiation inducing agent, a cell growth arrest inducing agent, an apoptosis inducing agent, a cytotoxic agent, a biologic agent, a gene therapy agent, or any combination thereof.

In one particular embodiment of the present invention, the HAT inhibitor is Spermidine-CoA, which can be administered in combination with any one or more of another HAT inhibitor, an alkylating agent, an antibiotic agent, an antimetabolic agent, a hormonal agent, a plant-derived agent, an anti-angiogenic agent, a differentiation inducing agent, a cell growth arrest inducing agent, an apoptosis inducing agent, a cytotoxic agent, a biologic agent, a gene therapy agent, or any combination thereof.

HAT inhibitors suitable for use in the present invention, include the spermidine CoA inhibitors of the 1a series. They can be synthesized as shown by Parello J, et al (1990) Comptes Rendus de l' Académie des Sciences Série II 310(11):1441-1446; and Roblot G, et al (1993) Tetrahedron 49:6381-6398. Compound 1a of the present invention has the following structure, and includes analogs thereof:

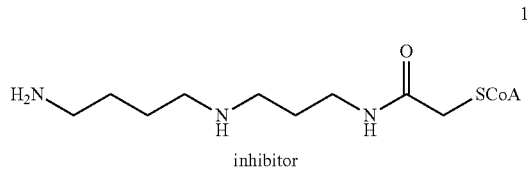

1a inhibitor

Examples of anticancer compounds of the present invention include compounds selected from carboplatin, gemcitabine, cisplatin, 5-fluorouracil, cyclophosphamide, etoposide, vincristine, doxorubicin and irinotecan.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Figure 4:
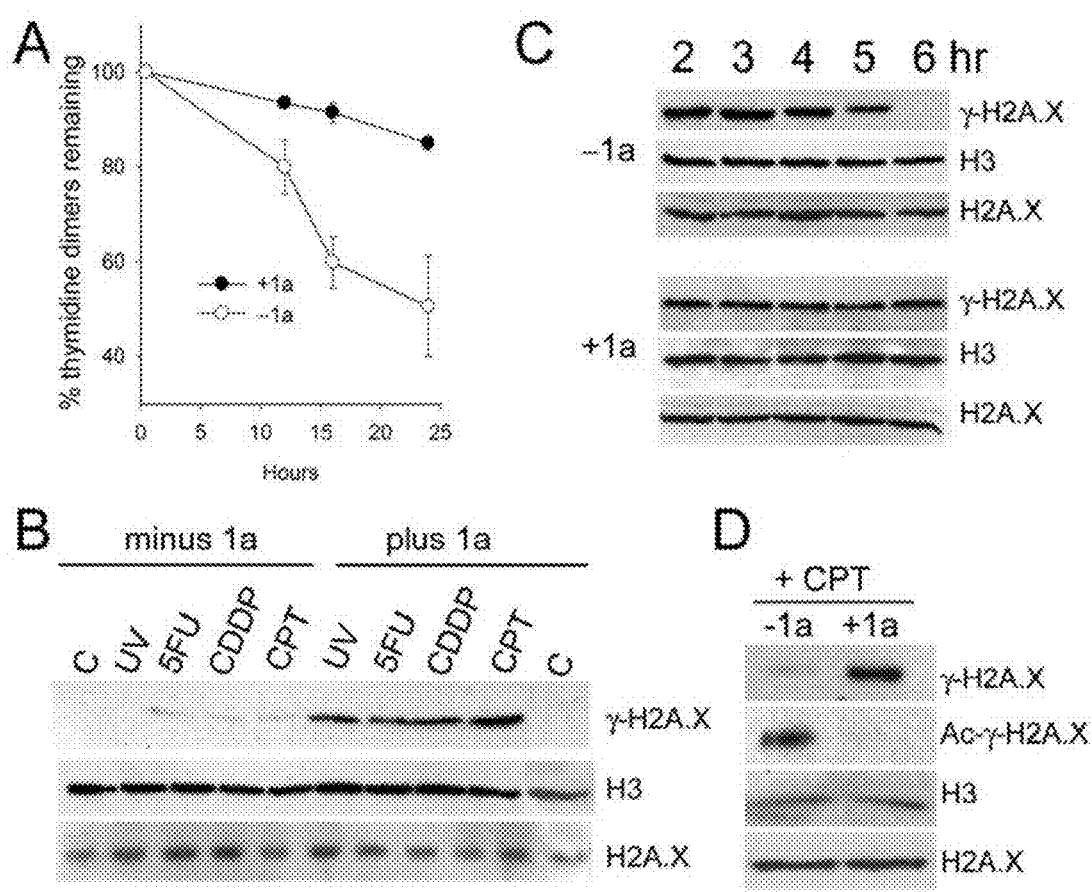
FIG. 4 demonstrates the effect of 1a on DNA repair. (A) Nucleotide excision/repair assay: Graph shows time course of removal of thymidine dimers from DNA of H358 cells following treatment with 40 J/m$^2$ UVC followed by incubation in the presence or absence of 50 μM 1a for the indicated times. (B) Induction of γ-H2A.X by the combination treatments used for DNA synthesis assays in FIG. 3: Western analysis shows γ-H2A.X or total H3 levels (control) in acid extracted histones from H358 cells (plus or minus 1a) 18 hours after treatment with UVC (40 J/m$^2$), 5-fluorouracil (5FU, 2 μM, 18 hours), cisplatin (CDDP, 2 μM, 1 hour 15 minutes), or camptothecin (CPT, 5 nM, 18 hours). Also shown are controls for no treatment ("c" minus 1a) or treatment with 1a only ("c" plus 1a). Each lane represents 60 µg protein. (C) Double strand break repair assay: Western blot shows γ-H2A.X and H3 levels at various times after the initiation of a 1-hour treatment of H358 cells with 10 µM camptothecin (1 hour), followed by incubation in the absence (upper 2 panels) or presence (lower 2 panels) of 50 µM 1a. Each lane represents 60 µg protein. (D) Inhibition of γ-H2A.X acetylation by 1a: Top row shows Western analysis of γ-H2A.X in acid extracted histones (60 µg protein per lane) from H358 cells treated with 5 nM camptothecin (18 hour) in the presence or absence of 50 µM 1a. Middle row shows results of an immunoprecipitation of 60 µg aliquots of the same extracts with anti-acetyl-lysine followed by Western analysis of γ-H2A.X in the immunoprecipitated material. Bottom row shows Western analysis of total histone H3 in 60 µg aliquots of the same extracts (control).

Embodiments of the present invention show that (N1) Spd-CoA, or 1a acts on whole cells to inhibit histone acetylation, suppress DNA synthesis, block DNA repair, and sensitize to UVC treatment and to the DNA targeted drugs, 5-fluorouracil, cisplatin (Platinol), and camptothecin. At least two mechanisms of DNA repair, namely nucleotide excision repair (NER) and double strand break (DBS) repair, are suppressed by 1a (see FIG. 4), and this is likely to contribute to the increased cellular sensitivity to DNA damage. From the in vitro experiments with an isolated recombinant fragment of p300, we observe that the inhibitor displays a modest affinity for the enzyme, with an estimated Ki in the range of 50-100 µM based on the formula IC50=Ki (1+Km/S)≅Ki under conditions of substrate excess. The fact that the effects of the inhibitor on histone acetylation occur within 1 hour after treatment of cells (FIG. 2D) and that the in vitro and in vivo effects occur at similar concentrations of inhibitor, indicates that the inhibitor is efficiently internalized and that an important cellular target is histone acetylation-dependent synthesis and repair of DNA. Although the inhibitor carries the negatively charged CoA moiety, internalization is likely to be favored by the positively charged spermidine moiety and may be mediated through the polyamine transporters. The transient nature of DNA synthesis and histone acetylation inhibition, which is most pronounced 12 hours after the addition of 1a, suggests that the inhibitor is unstable within the cell, thus accounting for the failure of the inhibitor to suppress 2-day cell viability. In support of this idea is our finding that daily replenishment of cell cultures with fresh inhibitor alone leads to reduced cell viability (unpublished observations).

Most conventional cancer treatments target DNA. However, enzyme-mediated DNA repair can promote chemo- and radio-resistance and is a promising target for the development of approaches to reverse therapy resistance. Nucleotide excision repair has been linked to cisplatin resistance, and both the nonhomologous endjoining (NHEJ) and homologous recombination (HR) mechanisms of double strand break repair have been linked to chemo and radiation resistance. Radiosensitization has been achieved with inhibitors of DNA Protein Kinase, an essential enzyme in NHEJ, and with inhibitors of poly(ADP-ribose) polymerase-1 (PARP-1), a component of the base excision repair (BER) complex, and a possible player in double strand break repair as well. Importantly, cancer stem cells, or cancer initiating cells, display a high degree of therapy resistance and appear to possess elevated DNA repair capacity compared to other cells within the tumor. An approach that targets DNA repair may therefore be particularly efficient in eliminating residual disease due to the stem cell population. The fact that treatment with 1a sensitizes to a variety of DNA damage types that are repaired through different mechanisms suggests that inhibition of histone acetylation by 1a may target most mechanisms of DNA repair involved in removing chemotherpay-induced DNA damage, and therefore have broad application. A further advantage is that sensitization occurs in both p53-null H358 cells and in MCF-7 breast cancer cells expressing wild-type p53, and is therefore independent of the p53-mediated apoptotis.

Although DNA repair appears to be an important target of spermidine-CoA-type HAT inhibitors, the inhibitory effects of spermidine-CoA-type inhibitors are likely to be mechanistically complex. At least 14 distinct lysine acetylation sites have been identified in the N terminal domains of the core histones H2A, H2B, H3, and H4, with two sites occurring in H2A, and four sites occurring in each of the three other core histones, so that within the octameric nucleosome core particle there are at least 28 potential sites of acetylation that can be acetylated in multiple combinations. In addition, there are acetylation sites in the internal globular domains of the histone, in particular, at lysine 56 in histone H3 and at lysine 91 in histone H4. These patterns are established by multiple families of histone acetylating enzymes. Although our in vitro assays have tested the inhibitory effects of 1a on recombinant p300/CBP only, using histone peptides as substrates (see FIG. 1), it is likely that the in vivo effects in cells are broader. In particular, our observations suggest that Tip60, which acetylates γ-H2A.X during DNA repair, is an additional likely target of 1a. Furthermore, the HAT enzymes act on non-histone substrates as well, and alterations in the activities and functions of these proteins may also contribute to the outcome of 1a treatment. Finally, 1a is a potent inhibitor of Spermine spermidine acetyltransferase (SSAT), an important regulator of intracellular polyamine content and subcellular distribution. Treatment with 1a could therefore interfere with polyamine-mediated regulation of histone acetylation, previously demonstrated in vitro with isolated polynucleosomes.

As stated above, one embodiment of the present invention is a spermidine CoA inhibitor. In connection with this embodiment, experiments were conducted to show inhibition of p300/CBP in vitro, inhibition of DNA synthesis, S-phase progression, and histone acetylation in whole cells. Also studied were synergistic effects of HAT inhibitors of the present invention and DNA damage, and inhibition of DNA repair.

Materials and Methods used for the experiments include the following:

Synthesis of Spermidine CoA Inhibitor.

A regioselective synthesis protocol that enabled the synthesis of spermidine[N1]-CoA and spermidine [N8]-CoA was described by Parello et al., "Regioselective synthesis of inhibitors of histone acetyl transferase covalently linking spermidine to the S-terminus of coenzyme A and fragments", Tetrahedron, 49: 6381-6398, 1993, incorporated herein by reference.

The synthesis leads to the possible transposition of the phosphate from 3' to 2' under acidic conditions—TFA deblocking, so that some Spd-isoCoA might be present in 1a.

In vitro Assay of Inhibition of p300HAT Activity.

Assays were performed using the fluorescent HAT assay kit (Active Motif, Carlsbad, Calif.), an H3 peptide as substrate (residues 5-23), the p300 catalytic domain as enzyme, and 50 µM inhibitor in duplicate, according to the manufacturer's instructions. Alternatively, a solution assay was performed using purified recombinant bacterially-produced p300 protein (residues 1284-1660) at 20 nM concentration in 50 mM Hepes pH 8, 250 µM acetyl CoA, and the 250 µM H4 (1-19-NH2) peptide. The reaction product, CoASH, was detected spectrophotometrically by reaction with 5,5'-dithiobis-2-nitrobenzoic acid (DTNB). Assays were carried out at 30° C. for 30 minutes, conditions which had previously been determined in kinetic assays to sufficient to achieve steady state.

Cell Lines and Growth Conditions.

H358 lung cancer cells and MCF7 breast cancer cells (American Type Culture Collection) were maintained at 37° C. in 10% $CO_2$ in Dulbecco's Modified Eagles Medium supplemented with nonessential amino acids, pyruvate, L-glutamine, gentamicin, and 10% fetal bovine serum.

2-day Cumulative Cell Growth and Viability Assays.

Cells were plated in 96-well plates (3000 cells per well) and incubated 18 hours with or without 5 nM camptothecin (Sigma, St Louis, Mo.). Triplicate wells were then treated with varying doses of 1a (from 0-50 µM). Control cells received neither 1a nor camptothecin. 2-day viability was determined by the MTS assay as previously (Saadatmandi et al., 2002, Cancer Gene Therapy, 9: 830-9) and expressed as a percentage of control cell viability.

DNA Synthesis Assays

Cells were plated in 96-well plates (2000 cells per well to insure conditions for exponential growth for untreated cells over the time course of the experiment) and exposed to the following treatments: 1a (50 µM); camptothecin (Sigma, St Louis, Mo. 5 nM, 18 hours); cisplatin (Platinol, obtained through local pharmacies, 2 µM, 1 hour 15 minutes), 5-fluorouracil (5FU, Adrucil™, obtained through local pharmacies, 2 μM, 1 hour 15 minutes), Taxotere (provided by the late Dr. Pierre Potier, 5 nM, 18 hours). UVC treatment (40 J/m$^2$) using a Stratalinker™, Stratagene, La Jolla, Calif.) was carried out using medium lacking phenol red. At 0-6 hr, 18-24 hr (day 1), 42-48 hr (day 3), 66-72 hr (day 3), and 90-96 hr (day 4) post-start of treatment, triplicate wells were incubated with 0.5 μCi [$^3$H]-thymidine (NEN, Boston Mass.), harvested onto filter paper, and subjected to scintillation counting. Trypan blue exclusion assays for cell membrane integrity were carried out as known in the art.

Cell Cycle Analysis

Cell cycle analysis was performed on propidium iodide-stained cells as known in the art using a FACScan Flow cytometer (Becton Dickenson, Franklin Lakes, N.J.). DNA histograms were analyzed with the FlowJo program using doublet discrimination. Each analysis was performed on two independent samples.

Western Immunoblot Analysis/Co-immunoprecipitation Analysis.

Cells were lysed by adding 1 mL of 0.2 M H$_2$SO$_4$. Histones were recovered as described in reference. SDS-PAGE/Western analysis was carried out as previously described using rabbit monoclonal antibody to total histone H3, rabbit polyclonal anti-trimethyl histone H3 (lysine 9), and anti-acetyl histone H3 (lysine 9). All antibodies were purchased from Upstate Biotechnology Inc. (Lake Placid, N.Y.).

DNA Repair Assays.

For NER, a slot blot immunoassay was used to detect the loss of thymidine dimers from the DNA of UVC treated cells as previously described. An antibody specific for cyclobutane pyrimidine dimers, the major photoproduct produced by UVC treatment, was purchased from Kamiya Biomedical Co (Seattle, Wash.; anti-thymidine dimer, clone KTM53) and used at 1:40 dilution.

To measure DSB repair, cells were incubated for 1 hour with 10 μM camptothecin to induce DSBs, followed by incubation in the presence or absence of 50 μM 1a. At fixed times, histones were prepared by extraction in 0.2M H$_2$SO$_4$ as described previously and 50 μg extract was analyzed by 12% SDS-PAGE followed Western analysis as described previously, using rabbit polyclonal anti-γ-H2A.X [phosphor ser 139] (Novus Biologicals, Littleton, Colo.) or anti-H3 (Upstate Biotechnology, Inc, Lake Placid, N.Y.). Band intensities were quantitated digitally. To study acetylation of γ-H2A.X, we carried out co-immunoprecipitation analysis using 50 μg extract protein in immunoprecipitation buffer (10 mM sodium phosphate pH 7, 0.15 M NaCl, 0.1% SDS, 1% NP40, 1% sodium deoxycholate, aprotinin, 1 mM PMSF, complete protease inhibitors (Roche) using immobilized anti-acetyl-lysine (Millipore, Temecula, Calif.) in the immunoprecipitation step. The immunoprecipitated material was then analyzed as for Western analysis using anti γ-H2A.X.

RESULTS

Inhibition of p300/CBP in vitro. N(1)Spd-CoA (embodiments of which are indicated as 1a throughout this work) a spermidine type histone acetyltransferase inhibitor based on the multisubstrate R-CoA design was synthesized as described above. The regioselective protocol allowed us to synthesize separately each of the two possible isomers, N(1)Spd-CoA and N(8)Spd-CoA, with the N1 or N8 terminal amino groups of spermidine linked to the CO group of the CO—CH2 spacer while the linker CH2 is directly bound to the S atom of CoA. Both isomers displayed comparable inhibitory activity against DNA synthesis in vivo (data not shown) and against endogenous HAT activity assayed in vitro with solubilized polynucleosomes (Bandyopadhyay et al, 2009, Cell Cycle 8(17): 2779-2788), and therefore only the N1-CoA isomer, 1a, was pursued in this study. The structure of 1a, and its resemblance to the reaction product of HAT-mediated acetyl transfer reaction to the lysine side chain is shown in FIG. 1A.

FIG. 1B shows an assay of recombinant enzyme p300HAT catalytic subunit activity under equilibrium conditions in the presence of increasing amounts of 1a, using as substrate a synthetic histone H4 N-terminal fragment that includes the four in vivo acetylation sites at lysine residues 5, 8, 12, and 16 (FIG. 1B). An IC$_{50}$ value of about 50-100 μM was inferred from the inhibitory plot (data reduction with the Prism software using a one site inhibition model, closed circles, experimental data points; plain line, theoretical profile). Using a 96-well-based assay of p300 HAT activity on a synthetic H3 peptide substrate that included the four in vivo acetylation sites at lysine residues 9, 14, 18, and 23, we found that 50 μM 1a inhibitor also suppressed p300HAT-mediated incorporation of acetyl groups into this substrate by 88% relative to control enzyme (FIG. 1C). Thus, the 1a inhibitor displayed broad inhibitory activity against histone acetylation, consistent with earlier work.

Inhibition of DNA synthesis, S-phase progression, and histone acetylation in whole cells. The present inventors used [$^3$H]-thymidine incorporation assays to examine DNA synthesis in H358 lung cancer cells in the presence of varying concentrations of 1a. Cells were pulsed for 6 hours with [$^3$H]-thymidine at three different time points after the addition of 1a (i.e., at 6-12 hours, at 18-24 hours, and at 42-48 hours). The incorporation of [$^3$H]-thymidine into DNA decreased with increasing concentrations of 1a at all three time points, with the maximal effect occurring with the 6-12 hour pulse (FIG. 2B). The IC$_{50}$ for inhibition of DNA synthesis during the 6-12 hour pulse occurred at about 50-100 μM Inhibition of DNA synthesis at a given 1a concentration was strongly dependent on the timing of the pulse, however, as the later [$^3$H]-thymidine pulse treatments showed reduced inhibition.

Treatment with 1a was associated with a slowing of S-phase progression as shown by the cell cycle analyses of propidium iodide-stained cells performed at various times after adding 50 μM 1a. As shown in FIG. 2C, H358 cells underwent a depletion of G2-phase cells that was maximal at the 12 hour time point post start of treatment, indicative of a transient inhibition of S-phase progression. By 24 hours, the cell cycle distribution had returned to normal.

In FIG. 2D, we carried out an immunoblot analysis of total histone H3, histone H3 acetylated on lysine 9 (H3-K9Ac), histone H3 acetylated on lysine 56 (H3-K56Ac) and histone H3 methylated on lysine 9 (H3-MeK9) in H358 cells, before treatment, and after 1, 12, 18, and 24 hours of treatment with 50 μM 1a. The treatment resulted in a reduction of histone H3 lysine 9 acetyl groups, with no effect on histone H3 lysine 9 methylation (FIG. 2D). Digital analysis of band intensities indicated that over 50% of histone H3 lysine 9 acetyl groups were lost within 1 hour and some 98% were lost within 12 hours under these conditions. Acetylation levels are restored by 24 hours. The finding that inhibition of both DNA synthesis and histone acetylation in vivo occur at an inhibitor concentration similar to what is needed to inhibit acetylating activity in vitro, indicates that the inhibitor is efficiently internalized, and that acetylation-dependent regulation of DNA synthesis is likely to be an important target.

Synergistic effects of 1a and DNA damage. We then used [$^3$H]-thymidine incorporation assays to examine DNA synthesis in H358 lung cancer cells in the presence of 1a alone, or together with an 18 hour exposure to the DNA damaging drug, camptothecin (CPT), a plant alkaloid from which an important class of topoisomerase I-targeted chemotherapeutic agents (Hycamtin [topotecan] and Camptosar [irinotecan]) has been derived (Garcia-Carbonero, et al, 2002, Clin Cancer Res 8: 641-61). Triplicate wells of cells were labeled for 6 hours with [$^3$H]-thymidine at 18-24 hr (Day 1), 42-48 hr (Day 2), 66-72 hr (Day 3), and 90-96 hr (Day 4) post start of drug treatment. For the first time point, untreated wells at the start of the experiment were labelled for 6 hours with [$^3$H]-thymidine. Incorporation per well at the end of the 6 hour pulse was determined by scintillation counting and is plotted in FIG. 3A. As shown in FIG. 3A (panel 1), treatment with 50 µM 1a alone caused a delay relative to untreated cells in the rate of increase in [$^3$H]-thymidine incorporation until after the 24 hour time point, indicative of a transient inhibition of DNA synthesis, and consistent with the results of FIG. 2A.

The present inventors examined the combined effect of 1a with camptothecin on DNA synthesis, using a camptothecin dose, 5 nM (18 hours), that had minimal effects on H358 cell growth by itself, based on previous viability assays (Bandyopadhyay et al., 2007, Biochemistry 46:14325-14334). This treatment had no detectable effect on [$^3$H]-thymidine incorporation in these cells (FIG. 3A, left panel). Cell viability, measured 18 hours after the start of each treatment by the trypan blue exclusion assay, a measure of cellular membrane integrity, confirmed that single agent treatment with either 1a or camptothecin had essentially no effect on cell viability (≥96% viability for untreated cells or single agent-treated cells). In contrast, treatment of cells with a combination of 1a and camptothecin resulted in a dramatic decrease in [$^3$H]-thymidine incorporation to less that 20% of control incorporation by 48 hours post-initiation of treatment (FIG. 3A), and to a loss of cell viability at 18 hours post initiation of treatment to about 36% of control. Similar results with 1a alone or in combination with camptothecin were also observed in the breast cancer cell line, MCF7 (FIG. 3A, right panel), indicating that the observations were not unique to H358 cells.

Consistent with the transient effect of inhibitor treatment on DNA synthesis inhibition (FIGS. 2B, 3A), we saw that treatment of H358 or MCF7 cells with increasing concentrations of 1a alone had little effect on 2-day cumulative cell viability relative to untreated cells (FIG. 3B, closed circles). Similarly, treatment of either cell line with 5 nM camptothecin alone (18 hour treatment), had no effect on 2-day cell viability relative to untreated cells (closed triangles, 0 µM 1a point). However, treatment of both cells lines with 5 nM camptothecin in combination with increasing concentrations of 1a led to a progressive loss of 2-day cell viability to less than 10% of untreated cell viability (FIG. 3B, closed triangles).

Figure 3:
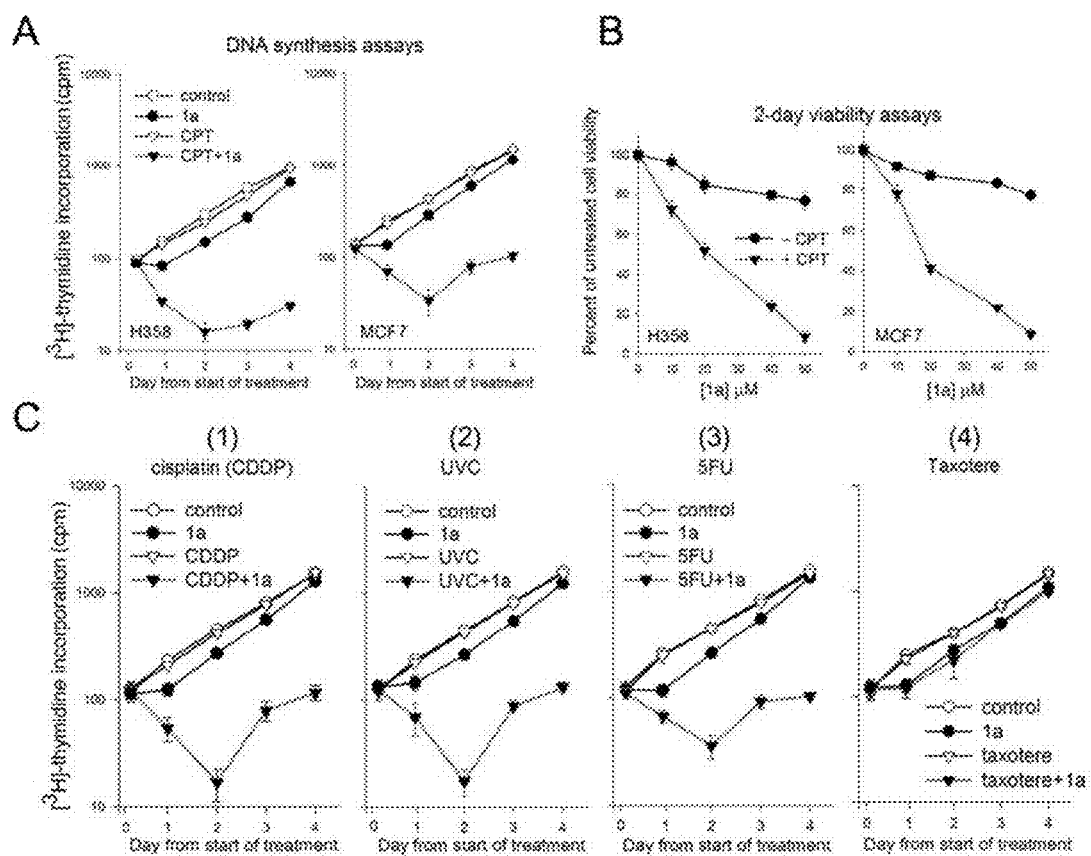
FIG. 3 shows the effect of 1a and 1a-combination treatments on DNA synthesis. (A) [$^3$H]-thymidine incorporation into DNA of H358 cells (left panel) or MCF-7 cells (right panel) during a 6 hour pulse ending at the indicated time points after initiation of treatment. Treatments were 50 μM 1a alone, 5 nM camptothecin alone (CPT, 18 hours), 50 μM 1a+5 nm CPT (18 hours). Control cells were left untreated. (B) 2-day 96-well viability assays of H358 cells (left panel) or MCF-7 cells (right panel) grown in presence of increasing concentrations of 1a (continuous), with or without an 18-hour treatment with 5 nM camptothecin (CPT). Cell viability, represented as a percent of untreated cell viability (i.e., no 1a, no CPT), was determined 2 days post-start of treatment by the MTS bioconversion assay (MTS=(3-(4,5'-dimethylthiazol-2-yl)-5-(3-carboxymethoxylphenyl-2-(4-sulfophenyl)-2H-tetrazolium salt). Each data point represents the average of triplicate wells. Assays were carried out under conditions such that untreated cells remained in exponential growth. (C) [$^3$H]-thymidine incorporation into DNA of H358 cells carried out as in part "A". Treatment consisted of 1a alone (50 μM), or cisplatin (2 μM, 1 hour, 15 minutes) alone or together with 1a (Panel 1); or UVC (40 J/m$^2$), alone or together with 1a (Panel 2); or 5-fluorouracil (5FU, 2 μM, 18 hours) alone or together with 1a (Panel 3), or taxotere™ (5 nM, 18 hours), alone or together with 1a (Panel 4). Control cells were left untreated. Symbols are as follows: (-○-) untreated control; (-●-) 50 μM 1a, (-▽-) drug or UVC alone; (-▼-) combination 1a+drug or UVC.

The present inventors then examined the combined effects of 1a with the DNA-targeted chemotherapeutic drugs, 5-Fluorouracil (5FU, Adrucil) and cisplatin (cis-diamminedichloro-platinium, CDDP, Platinol), and with UVC radiation. They also examined the combined effect of 1a with the chemotherapeutic agent, Taxotere, which targets microtubules and does not damage DNA. As with camptothecin, the conditions for each drug treatment or for UVC irradiation were chosen based on the ability of the treatment to suppress cell viability on its own by about 10% in 3-day viability assays carried out over a range of doses (data not shown). As shown in FIG. 3C, treatment with 1a sensitized H358 cells to cisplatin (CDDP), UVC irradiation, and 5-FU (panels 1-3), but not to Taxotere (panel 4). Taken together, the results in FIG. 3 (A-C) suggest that a common mechanism, relevant to DNA damage, underlies the ability of histone acetylation inhibition to synergize with drugs and radiation.

Inhibition of DNA repair. DNA repair can promote cell survival following DNA damage. Nucleotide excision repair (NER), which requires histone acetylation (Cazzalini et al., 2008, 36: 1713-22) removes bulky DNA adducts such as the intrastrand guanine-adenine crosslinks caused by cisplatin or the intrastrand thymidine dimers produced by UVC radiation. We assayed NER in the presence or absence of 50 µM 1a using an immunoblot analysis of thymidine dimers in cellular DNA prepared from cells at fixed times after exposure to 40 J/m$^2$ UVC radiation. As shown in FIG. 4A, 50% of thymidine dimers are removed from the DNA of untreated cells within 24 hours post-treatment, but dimers persist in 1a treated cells, decreasing by only 40% over the same time frame. The results support a model in which acetylation of the core histones, accompanied by localized relaxation of chromatin structure, may be necessary to initiate DNA repair, possibly by allowing access of DNA to multiprotein repair complex involved in nucleotide excision repair, or by promoting recruitment of those factors. The inhibitor 1a would interfere with such a process.

Double strand breaks (DSBs) can be formed by a variety of DNA damaging agents, including camptothecin, cisplatin, 5FU, and UVC radiation (Avemann K, et al., 1988, Mol Cell Biol, 8: 3026-34; Bogdanov K V, et al. 1997, Br J Haematol, 98:869-72; Pavon M A, et al., Int J Cancer, 2008, 123:1068-79) implying that DSB repair may play a role in reducing their cellular toxicity. To examine how 1a treatment affects DSB repair in H358 cells we made use of the fact that the histone variant, H2A.X becomes phosphorylated at sites of double strand breaks (denoted γ-H2A.X), and can be detected by immunoblot analysis of acid extracted cells (Rogaku E P, et al., 1999, J Cell Biol, 146:905-16). Cells treated with UVC, 5-FU, cisplatin, or camptothecin at the low doses used for the growth assays in FIG. 3, either as single agents, or in combination with 50 µM 1a, were analyzed 18 hours post-start of treatment. γ-H2A.X is undetectable in untreated cells or in cells treated with 1a or UVC alone and is weakly detectable in cells treated with 5FU, cisplatin, or camptothecin alone (FIG. 4B). γ-H2A.X levels increase dramatically when these treatments are combined with 1a, indicating increased levels of DSBs. Total H3 levels and H2A.X levels (control) are unaffected by these treatments (FIG. 4B). To follow DSB repair, H358 cells were treated with 10 µM camptothecin for 1 hour to induce a high level of double-stranded DNA breaks, followed by incubation in the presence or absence of 50 µM 1a for various lengths of time. Acid extracts of cells were prepared at regular intervals following camptothecin treatment and subjected to immunoblot analysis for γ-H2A.X. As shown in FIG. 4C, γ-H2A.X levels decrease over time in the absence of 1a, and are undetectable after 6 hours post-start of treatment, indicating that double strand breaks have been repaired. In contrast, γ-H2A.X levels persist in cells treated with 1a, indicating persistence of double strand breaks. Levels of total histone H3 and H2A.X (control) remain unchanged in both cases over the same time period (FIG. 4C).

Acetylation of γ-H2A.X is required for its removal and replacement with non phosphorylated H2A.X during DNA repair, and failure of histone acetylation adjacent to double strand breaks has been reported to impair the efficiency of DNA repair. This raises the possibility that treatment with 1a may block double strand break repair by interfering with acetylation of histone γ-H2A.X. To test this hypothesis we treated H358 cells for 18 hours with 5 nM camptothecin in the presence or absence of 50 μM 1a (as in FIG. 4B). We then prepared acid extracted nuclei from treated cells and carried out an immunoprecipitation with an immobilized anti-histone acetyl antibody, followed by an immunoblot analysis of histone γ-H2A.X. As shown in FIG. 4D, cells treated with 1a, fail to acetylate γ-H2A.X, suggesting that this defect could contribute to the failure of cells to complete double strand break repair.

The following examples demonstrate aspects of the present invention. They are to be viewed as exemplary in nature and not to be viewed as limiting of the present invention.

Example 1

The present inventors found that treatment of H358 lung cancer cells with 50 μM 1a results in specific loss of histone acetyl groups. One 10-cm plate of H358 lung cancer cells (about $2\times10^6$ cells), grown in DMEM+10% Fetal bovine serum as described in reference, were treated for 24 hours with 50 μM 1a inhibitor. Cells lysates were prepared as we have previously described (Lee C, et al., 2005, Cancer Res 65:9834-9842). Treated cells and untreated (control) cells were harvested by lysing in buffer containing 10 mM Hepes pH 7.5, 100 mM NaCl, 300 mM sucrose, 3 mM MgCl2, 1 mM EDTA, 1 mM DTT, 0.5% Triton X-100, 1 mM PMSF, protease inhibitor pellet (Roche) and analyzed on 10% SDS-PAGE gels, followed by Western immunoblot analysis of total histone H3, methylated histone H3 (methylated on lysine 9), and acetylated histone H3 (acetylated on lysine 9). As shown in FIG. 5, treatment with 1a inhibitor resulted in specific depletion of histone acetyl groups. Histone H3 methylation was not affected. Digital analysis of band intensities indicated that over 80% of histone H3 K9 acetyl groups were lost under these conditions. These results are the first to provide evidence for cellular internalization and in vivo effect of this inhibitor.

The present inventors used 96-well viability assays as described in Saadatmandi et al (Cancer Gene Therapy (2002) 9:930-9) to examine the effect of 1a on DNA synthesis in H358 cells, as well as the combined effects of 1a and chemotherapeutic agents. H358 cells were plated in 96-well plates at 3000 cells per well. Following overnight attachment, triplicate wells were either labeled immediately with 1 μCi [$^3$H]-thymidine per well for 6 hours (control, starting DNA synthesis rate), or treated as follows: (a) 50 μM 1a for 24, 48, 72, or 96 hours followed by labeling with [$^3$H]-thymidine; (b) 5 nM of the chemotherapeutic agent camptothecin (non-inhibitory dose) for 24 hours followed by immediate labeling with [$^3$H]-thymidine, or by replacement of medium (no camptothecin) and labeling 48, 72, 96 hours post start of camptothecin treatment; (c) combined treatment with 5 nM camptothecin (24 hours) plus 50 μM 1a (continuous), followed by labeling 24, 48, 72, and 96 hours post start of treatment. Triplicate wells were used for each treatment condition. Following the 6-hour labeling, cells were harvested and incorporation of [$^3$H]-thymidine was determined by scintillation counting. As shown in FIG. 6, treatment with 50 μM 1a alone resulted in a transient arrest of DNA synthesis that was evident at 24 hours. However, by 48 hours, DNA synthesis rates had been restored to levels equivalent to untreated cells. Treatment with 5 nM camptothecin had no effect on DNA synthesis rates. We measured cell viability 24 hours after the start of each treatment by the trypan blue exclusions assay, a measure of cellular membrane breakdown. We found that single agent treatment with either 1a or camptothecin had no effect on cell viability (≥96% viability).

In contrast, treatment of cells with a combination of 1a and camptothecin resulted in a dramatic decrease in the DNA synthesis rate to some 10% of control rate by 48 hours post treatment (FIG. 6), and to a loss of cell viability at 24 hours post treatment to about 36%.

These are the first results that show that inhibition of histone acetylation blocks DNA synthesis and synergizes with chemotherapy to inhibit tumor cell growth and viability. Accordingly, embodiments of the present invention include the use of acetytransferase inhibitors of the spermidine CoA type, as well as modified CoA-conjugates (see exemplary Scheme), as therapy sensitizers for cancer.

Example 2

The present inventors have also observed synergistic effects of 1a+cisplatin and 5-fluorouracil. [$^3$H]-thymidine incorporation assays as in the previous example are used. As with CPT, the drug treatment conditions were chosen so as to suppress 3-day cell viability by about 10% (data not shown). As shown in FIG. 7, treatment with 1a sensitized H358 cells to cisplatin (CDDP), UVC irradiation, and 5FU (panels 1-3), but not to Taxotere™ (panel 4), indicating that a common mechanism, relevant to DNA damage, underlies the ability of histone acetylation inhibition to synergize with drugs and radiation.

Example 3

The present inventors carried out 96-well viability assays as we have previously described (Saadatmandi et al, Cancer Gene Therapy (2002) 9:830-9), in which MCF7 breast cancer cells were plated at 3000 cells per well. After overnight attachment, triplicate wells were treated with increasing doses of inhibitor 1a. Control wells were left untreated. After 3 days, cell viability was measured by the MTS assay, which measures the bioconversion of an uncolored substrate to a colored formazan derivative, and is proportional to cell number. The results, plotted in FIG. 8 as a percent of maximum cell viability of control wells, show that a single exposure of cells to the 1a inhibitor alone has minimal effects on cell viability over the range of concentrations studied, consistent with a transient effect on DNA synthesis.

The present inventors examined the direct effect of 1a on HAT activity using the Active Motif 96-well assay which measures acetylation of a histone H4 fragment by the p300 subunit of histone acetyltransferase. As shown in FIG. 9, 50 μM 1a inhibits the incorporation of acetyl groups into the H4 peptide substrate by 88% relative to untreated wells. These in vitro results are consistent with those of Cullis et al (1982) J Biol Chem 257:12165-12169. Furthermore, the fact that the concentrations needed for HAT inhibition in vitro were similar to those needed to arrest DNA synthesis and to block histone acetylation in whole cells, suggests that a major cellular target of the inhibitor is histone acetylation-mediated effects on DNA synthesis.

The present inventors also carried out 96-well viability assays following procedures described in Saadatmandi et al, Cancer Gene Therapy (2002) 9:830-9), in which H358 lung cancer cells were plated at 3000 cells per well. After overnight attachment, triplicate wells were treated with increasing concentrations of inhibitor 1a or 1b. Control wells were left untreated. One day later, and again 2 days later, the medium in the wells was removed and replaced with fresh medium containing 1a or 1b. After 3 days, cell viability was measured by the MTS assay and expressed as a percentage of control (untreated) cell viability. The results, plotted in FIG. 10 as a percent of maximum cell viability of control wells, show that repeated exposures of cells to the 1a or 1b inhibitor alone could suppress 3 day cell viability by some 60-70%.

Example 4

This example demonstrates that the inhibitors of the present invention are cancer cell-specific therapy sensitizers.

The present inventors used a 96-well viability assays as described in Saadatmandi et al (Cancer Gene Therapy (2002) 9:930-9) to examine the effect of the spermidine-CoA inhibitor disclosed previously on DNA synthesis in normal GT41F human skin fibroblast cells, as well as its combined effect with camptothecin. GT41F cells were plated in 96-well plates at 3000 cells per well. Following overnight attachment, triplicate wells were either labeled immediately with 1 μCi [$^3$H]-thymidine per well for 6 hours (control, starting DNA synthesis rate), or treated as follows: (a) 50 μM inhibitor for 24, 48, 72, or 96 hours followed by labeling with [$^3$H]-thymidine; (b) 5 nM of the chemotherapeutic agent camptothecin (non-inhibitory dose) for 18 hours followed by immediate labeling with [$^3$H]-thymidine, or by replacement of medium (no camptothecin) and labeling 48, 72, 96 hours post start of camptothecin treatment; (c) combined treatment with 5 nM camptothecin (18 hours) plus 50 μM 1a, followed by labeling 24, 48, 72, and 96 hours post start of treatment. The points on the curves represent averages of triplicate wells with standard deviations shown. Following the 6-hour labeling, cells were harvested and incorporation of [$^3$H]-thymidine was determined by scintillation counting. As shown in FIG. 11, treatment with 50 μM 1a alone, camptothecin alone, and 1a+camptothecin had virtually no effect on incorporation of [$^3$H]-thymidine, in contrast to what the present inventors observed in H358 lung cancer cells with embodiments of the present invention.

Example 5

This example demonstrates cancer-specific targeting of Spermidine-CoA inhibitors of histone acetylation. Without being bound by theory or mechanism, the cancer cell specificity derives from the differential expression of the polyamine transporter on the surface of cancer cells compared to normal cells (human skin fibroblasts and immortalized human epithelial cells) under conditions where rates of cellular proliferation are the same for the three types of cells. We propose that the spermidinyl moiety of Spd-CoA (even though it provides only two positively charged ammonium groups instead of spermidine itself with three positive charges) provides cancer-specific targeting and spares proliferating normal cells, thereby reducing therapy toxicity. It has been suggested that in *E. coli* the spermidine transporter (for which a high-resolution X-ray structure is available) might also bind putrescine with two positive charges (Sugiyama et al., Protein Science 1996, 5, 1984-1990). Spd-CoA with two positive charges displays a strong structural similarity with putrescine. The eukaryotic analog of the bacterial spermidine transporter is not presently known.

Although polyamines are known to be actively transported into cancer cells, it was generally thought that this transport correlated with the increased level of cellular proliferation, rather than with cellular transformation per se. Here we find that increased cellular uptake of spermidine occurs in proliferating cancer cells (H23 lung cancer cells) but not in proliferating normal human skin fibroblasts (GT41F, not immortalized) nor in immortalized human epithelial cells (HET 1a). The observation that differential uptake of spermidine is a feature of tumorigenic transformation is therefore novel and unexpected.

FIG. 12 shows low spermidine uptake in normal skin fibroblasts compared to tumor cells. (A) Spermidine uptake into H23 lung cancer cells, HET1a immortalized human epithelial cells and GT41F normal human skin fibroblast cells as assayed according to procedures described in Lopez-Contreras A J, et al (2008) *J Biol Chem* 283:20761-20769). Cells were plated at 5×10$^5$ cells per well in 24-well plates and treated with 2 μM $^3$[H]-spermidine (16.6 Ci/mmol, Perkin Elmer, Boston, Mass.) for two hours. Cells were harvested by trypsinization and subjected to scintillation counting. (B) 96-well assay of incorporation (cpm) into H23, GT41F, and HET1a cells during a 6-hr pulse with 0.5 μCi [$^3$H]-thymidine (NEN, Boston, Mass.) on the indicated days after plating (initial plating 2000 cells per well). Each point represents the result of duplicate wells, with standard deviations shown.

Example 6

This example shows the cellular effects of a modified inhibitor, designated 2a. The 2a compound is based on the spermidine-CoA structure of the 1a compound, but the CoA moiety has been truncated so that only the cysteamine-beta-alanine portion of the CoA moiety (=S—R in part A of FIG. 13) is retained. The data show that 2a is also inhibitory of p300/CBP HAT activity in vitro using a commercially available 96-well p300/CBP HAT assay (Part B of FIG. 13), and suppresses histone acetylation in vivo in H358 cells in a time frame similar to that of 1a (Part C in FIG. 13), with greatest inhibition occurring at 12 hours post start of treatment. Furthermore, 2a is also active against whole cells and synergizes efficiently with camptothecin (CPT) to kill H358 lung cancer cells (Part D in FIG. 13).

Example 7

This example relates to the in vivo properties of Spermidine-2a (also designated spd-2a, or 2a), and shows that compound 2a in combination with the chemotherapeutic agent, Irinotecan (Camptosar) eradicates tumors in a nude mouse subcutaneous model for DU145 prostate cancer. In addition, this example shows an anti-tumor effect with the 2a compound alone.

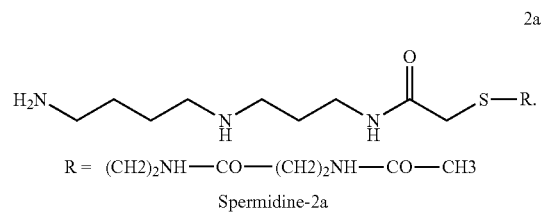

2a

R = (CH2)2NH—CO—(CH2)2NH—CO—CH3

Spermidine-2a

This Example shows that intraperitoneal administration of Irinotecan (at the time points indicated by arrows (↑) along the x-axis), together with intratumoral administration of 2a (at the time points indicated by bars (I) along the x-axis), caused complete regression of tumors (FIG. 14).

Another embodiment of the present invention, intravenous administration of 2a was also shown to be effective, in combination with Irinotecan, in causing complete tumor regression (FIG. 15).

A further embodiment of the present invention, treatment with 2a alone, is shown below, administered intravenously as described for FIG. 16, caused a significant decrease in tumor growth. A paired t-test was used to evaluate the differences between the controls versus 2a-treatment groups. A significant difference (p<0.01) was observed. The results suggest that 2a could have an anti-tumor effect as a single agent if used at higher concentrations.

Example 8

This example relates to the use of Spermidine-CoA (designated 1a) and the truncated derivative, 2a as inhibitors of polyamine metabolism. This example also provides additional evidence for the use of 2a as a chemo sensitizer for breast cancer. When used in combination with difluoromethyornithine (DFMO), an inhibitor of de novo polyamine biosynthesis that has been evaluated in clinical trials for breast cancer, we can achieve virtually complete suppression of breast cancer cell growth in culture, at doses where the 2 agents are ineffective when used singly.

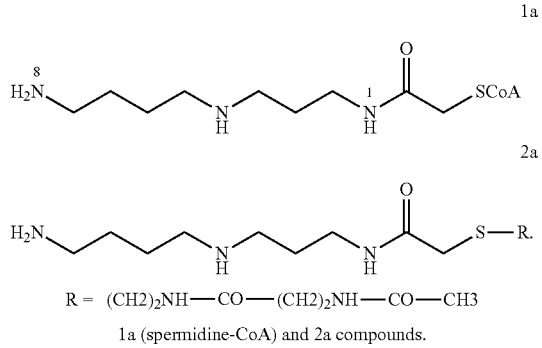

1a (spermidine-CoA) and 2a compounds.

Polyamines (PA) are amino acid-derived organic cations essential for the growth and viability of all cells from bacteria to mammals. The three polyamines putrescine, spermidine, and spermine are found in mammalian cells and are involved in a wide variety of cellular functions, including cellular proliferation, growth, differentiation, migration, and apoptosis. Although polyamine levels in normal cells are tightly controlled through a balance of de novo biosynthesis, uptake, and excretion, this balance is disrupted in cancer and leads to increased de novo biosynthesis, increased uptake, increased intracellular accumulation, and increased excretion. Cancer cells cannot grow when depleted of polyamines, as revealed through the use of targeted compounds directed at specific points in polyamine metabolism. Polyamine metabolism therefore has considerable potential as a cancer-specific therapeutic and diagnostic target for cancer.

De novo biosynthesis of polyamines begins with Ornithine Decarboxylase (ODC)-mediated decarboxylation of ornithine to produce putrescine, followed by the successive addition of aminopropyl groups to form spermidine and spermine. The importance of ODC in cancer has been demonstrated in studies showing that its forced overexpression is sufficient for malignant transformation of mouse fibroblasts. Furthermore, ODC activity is increased in cancer tissue compared to adjacent normal tissue and for breast cancer, is an independent indicator of poor prognosis. In addition to increased de novo polyamine biosynthesis, cancer cells display an increased ability to take up polyamines from the outside through an energy-dependent process mediated by a saturable membrane-associated transporter. The polyamine transporter is able to accommodate polyamine-related compounds as well, making it an important tool for targeting polyamine-based therapeutics specifically to the cancer cell, thereby achieving suppression of cancer cells without toxicity to normal tissue.

ODC, the first and rate-limiting enzyme in the polyamine synthetic pathway, has been associated with proliferation and progression of breast cancer, and is a key potential target for therapy. ODC can be irreversibly and specifically inactivated by α-difluoromethylornithine (DFMO), and treatment of breast cancer cell lines with DFMO blocks the conversion of ornithine to putrescine and inhibits their proliferation in vitro and in mouse tumor models. DFMO also inhibits in vitro invasiveness of breast cancer cells and in some but not all murine models for breast cancer, DFMO can prevent metastatic spread. DFMO has been evaluated in Phase I and II clinical trials for breast cancer and other cancers, but has failed to show sufficient anti-tumor efficacy to justify further clinical development as anti-tumor agent. One explanation for its poor clinical efficacy is its failure to suppress the final product of polyamine metabolism, spermine, due to a compensatory increase in Adenosylmethionine decarboxylase (AMDC) activity that occurs when ODC is inhibited. There is evidence that a combined approach that suppresses both AMDC and ODC in breast cancer cells in culture induces a greater anti-proliferative and anti-invasive effect. A variety of polyamine analogues have been developed as inhibitors of polyamine biosynthesis by virtue of their structural similarity to natural polyamines. One promising compound, a bis-ethyl-substituted spermine that inhibits both ODC and AMDC, has been advanced to clinical trials for breast and lung cancer, where it has shown minimal toxicity. Nevertheless, a combined treatment to suppress both ODC and AMDC in mice bearing orthotopic MDA-MB-435 tumors did not display anti-tumor effects, and the clinical efficacy of bis-ethyl-substituted spermine has been poor, possibly because pharmacological inhibition of polyamine biosynthesis is known to lead to a compensatory increase in polyamine uptake (Pegg A E, 1988, Cancer Res 48: 759-74; Seiler N, et al., 1996. J Biochem Cell Biol 28:843-61). Thus, despite its advantage as a cancer-targeted, non-toxic therapy, the poor clinical response achieved with this and other agents that only block polyamine biosynthesis highlights the need for agents with broader and more multitargeted inhibitory activity.

As indicated above, embodiments of the present invention include Spermidine-CoA as a cancer-cell-specific therapy sensitizer.

This Example shows both 1a and 2a competing with spermidine for uptake into cancer cells in culture. At high enough concentration, they can block most cellular uptake of spermidine (FIG. 17). This is important because 2a treatment of tumor cells may therefore block the compensatory increase in uptake that occurs in the presence of DFMO. The ability to inhibit uptake of spermidine is likely to extend to spd-3a as well.

This Example further shows that when breast cancer cells are treated with doses of 2a and DFMO where each is ineffective as a single agent, we can suppress MCF 7 breast cancer cell growth by some 90% (over the 3 days of the assay) and MDA-MB-435 breast cancer cell growth by about 80% (FIG. 18).

Embodiments of the present invention show that 1a is a chemosensitizer to the chemotherapeutic agent, 5-fluorouracil (5FU). This example extends that observation to the 2a compound and to breast cancer cells (FIG. 18). We also show that 2a is a sensitizer to an additional breast cancer therapeutic, doxorubicin (dox, Adriamycin), indicating that 1a, 2a, and other compounds of the present invention have a general sensitizing effect for most chemotherapeutic agents. For the assay in FIG. 18 we have used doses of 5FU and doxorubicin (Dox) that have minimal effects when used as single agents. 2a itself also had minimal effects on the two cell lines over the 2 days of the assay (FIG. 18). The results are consistent with our results in Example 6. Both 5FU and doxorubicin can cause DNA damage. 2a and related compounds, including Spd-3a (see Example 11) can therefore be used to increase the efficacy and reduce the toxicity of conventional therapeutics for all or most cancers, including breast cancer.

Example 9

This example relates to the use of the Spermidine-CoA conjugate designated 2a as an inhibitor of polyamine metabolism. When used in combination with difluoromethylornithine (DFMO), an inhibitor of de novo polyamine biosynthesis that has been evaluated in clinical trials for breast cancer, 2a can also suppress tumor growth in vivo using a subcutaneous DLD-1 colon cancer model. Above is shown that embodiments of the present invention can achieve virtually complete suppression of breast cancer cell growth in culture, at doses where the 2 agents are ineffective when used singly

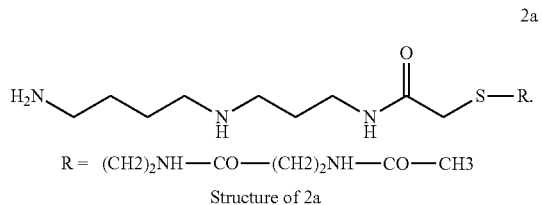

Structure of 2a

Example 10

The panels on FIG. 20 (1-5) relate to the dual application of the compounds 1a and 2a, and related compounds (see panel, ①) as chemosensitizers or as co-repressors of polyamine metabolism when used together with DFMO (difluoromethyornithine) or another suppressor of polyamine biosynthesis.

Panel ① shows the structures of compounds 1a and 2a described previously, and their resemblance to the acetylated side chain of lysine. R3=(CH2)2NH—CO—(CH2)2NH—CO—CH3.

Panel ② (middle) describes schematically how the HAT inhibitor 2a functions in synergy with a DNA-damaging chemotherapeutic drug to enhance cell killing. By preventing DNA repair, the HAT inhibitor prevents this cancer cell survival mechanism that can reduce the efficacy of treatment. In the presence of chemotherapy plus HAT inhibitor, DNA damage persists and accumulates, causing cell death.

The immunofluorescence images on the left and right sides of the middle scheme illustrate this visually. On the left, DU 145 prostate cancer cells in culture were treated for 8 hours with 5 nM camptothecin, a dose that has minimal effects on cell viability. Cells were fixed and stained with a rabbit antibody to the histone variant, γ-H2A.X, a marker for DNA double stranded breaks, followed by staining with a fluorescein (FITC)-tagged goat anti rabbit secondary antibody. Nuclei were stained with Hoescht 33345. As shown in the image, treatment with 5 nM camptothecin alone caused minimal damage (green spots within nuclei).

On the right panel, DU145 prostate cancer cells were treated for 8 hours with 5 nM camptothecin plus 10 μM 2a. The dose of 2a has minimal effects on cell viability. Following staining for gamma H2A.X, we see extensive amounts of DNA damage. The combination treatment achieves some 50% reduction in cell viability by 48 hours (see results for H358 cells in Example 7; similar results are obtained with DU145 cells).

Panel ③ shows the results of a subcutaneous DU145 tumor model in nude mice, showing how the combination of Irinotecan, a chemotherapeutic drug derived from camptothecin, synergizes in vivo with 2a treatment. This Example shows that intraperitoneal administration of Irinotecan (at the time points indicated by arrows (↑) along the x-axis), together with intratumoral administration of 2a (at the time points indicated by bars (|) along the x-axis), caused complete regression of tumors (see also FIG. 7-1 above). Animals in Irinotecan (Camptosar) only group received 40 mg/kg Irinotecan intraperitoneally on days 2, 8. Animals in Irinotecan+2a group received Irinotecan intraperitoneally on days 2, 8 (9 AM) and 100 μl of 100 μM 2a administered intratumorally, equivalent to 0.2 mg/kg, on days 1 and 7 (5 PM) and days 2 and 8 (9 AM and 5 PM). Tumors were measured and volumes calculated as in part A.

Panel ④ shows an overview of pathways involved in polyamine metabolism. Polyamines are required for cell growth. Suppression of polyamine biosynthesis may be insufficient to suppress cell growth because of compensatory polyamine uptake.

Panel ⑤ shows a scheme depicting the dual therapeutic activities of compounds 1a, 2a, 3a and related compounds. They can be used in combination with DFMO or other inhibitors of polyamine biosynthesis to further suppress polyamine metabolism, or in combination with conventional chemotherapy to exacerbate DNA damage and induce cell killing.

Example 11

This example shows the cellular effects of a modified inhibitor, designated Spd-3a (or 3a). The 3a compound is based on the spermidine-CoA structure of the 1a and 2a compounds, but the CoA moiety has been further truncated as shown in part A of FIG. 21 (see chemical synthesis of Spd-3a, below). The data show that 3a suppresses histone acetylation in vivo in H358 cells in a time frame similar to that of 1a and 2a (Part B of FIG. 21), with nearly complete ablation of histone H3K9 acetylation at 12 hours post start of treatment. Furthermore, 3a is effective in combination with camptothecin at suppressing DNA synthesis in H358 cells (part C of FIG. 21) and at suppressing 3-day H358 cell viability (part D of FIG. 21). Without being bound by theory or mechanism, the results observed with Spd-3a (in comparison to Spd-2a) suggest that Spd-3a (which has a lower inhibitory effect than Spd-2a on the endogenous HATs associated with solubilized chromatin: Parello et al. 1990, C.R.Acad.Sci.Paris, Serie II, 310:1441-1446) is transported more readily than Spd-2a (and Spd-1a) through the plasma membrane so that the intracellular concentration of Spd-3a becomes higher at a given time post drug administration than the Spd-2a (or Spd-1a) concentration. This would thus lead to an enhanced inhibitory effect on chromatin acetylation likely due to higher saturation conditions of the enzyme targets.

Synthesis of Spd-3a. The final compound was obtained through the pathway illustrated above. The compound was characterized by 400 MHz 1D 1H NMR at 298 K in $D_2O$ (reference: HDO at 4.700 ppm): 1.687 ppm 4H for $^7CH2$ and $^8CH2$, quintuplet with J=3 Hz due to virtual coupling to $^6CH2$ and $^9CH2$; 1.842 ppm 2H for $^{12}CH2$ quintuplet J=8 Hz; 1.917 ppm 3H for $^5CH3$ singulet; 2.655 ppm 2H for $^{1'}CH2$ triplet J=6 Hz; 2.95-3.03 ppm 6H including $^4CH2$,

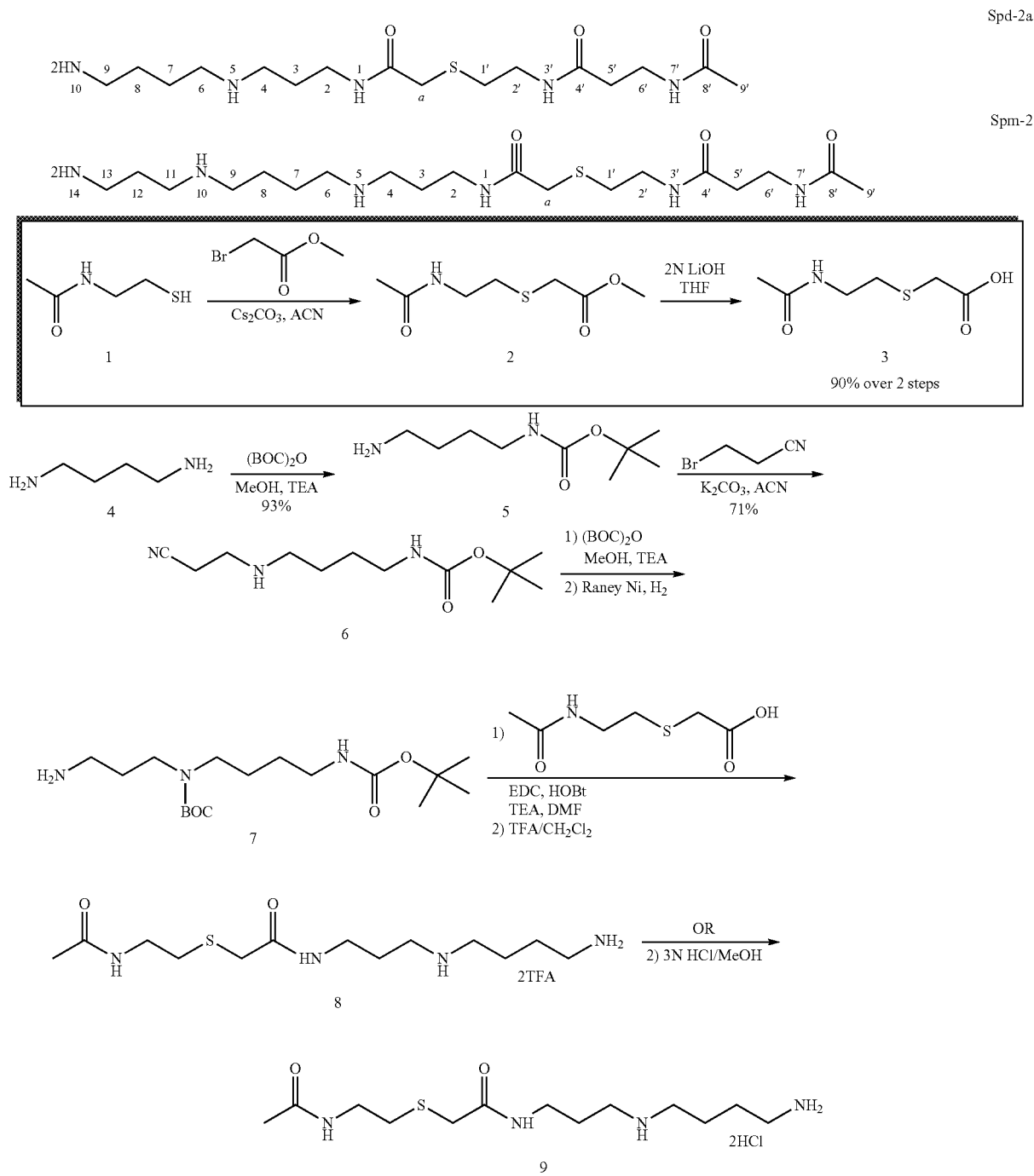

Above is shown the synthesis of Spd-3a (corresponding to compounds 8 and 9 above) following Roblot et al., 1993 (Tetrahedron 96:6381-6398) after adaptation.

$^6CH2$, $^9CH2$; 3.239 ppm 2H for $^aCH2$ singulet; 3.251 ppm 2H for $^2CH2$ triplet J=8 Hz; 3.311 ppm 2H for $^{2'}CH2$ triplet J=6 Hz.

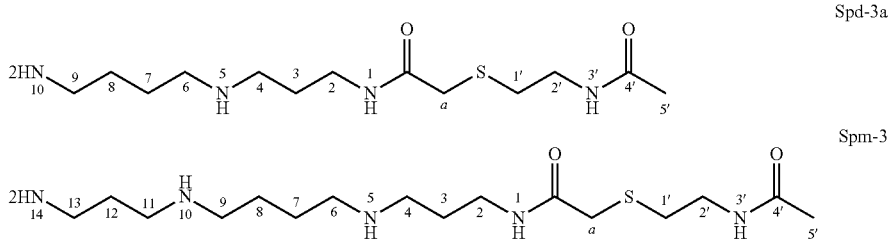

Synthesis of Spm-3. Using 3 and Boc-triprotected spermine (with its N1 amino group unprotected the synthesis of Spm-3 was achieved (according to synthesis illustrated above). The compound was characterized by ESI-MS with [M+H]$^+$=362 for 362.23 (calc.) and by 400 MHz 1D 1H NMR at 298 K in D$_2$O (reference: HDO at 4.700 ppm): 1.70 ppm 4H for $^7$CH2 and $^8$CH2, quintuplet with J=3 Hz due to virtual coupling to $^6$CH2 and $^9$CH2; 1.84 ppm 2H for $^{12}$CH2 quintuplet J=8 Hz; 1.92 ppm 3H for $^{5'}$CH3 singulet; 2.02 ppm 2H for $^3$CH2 complex quintuplet J=6 Hz; 2.66 ppm 2H for $^{1'}$CH2 triplet J=6 Hz; 2.97-3.10 ppm 10H including $^4$CH2, $^6$CH2, $^9$CH2, $^{11}$CH2, $^{13}$CH2; 3.24 ppm 2H for $^a$CH2 singulet; 3.25 ppm 2H for $^2$CH2 triplet J=8 Hz; 3.31 ppm 2H for $^{2'}$CH2 triplet J=6 Hz.

Synthesis of 4a

Compound 3.

A mixture of cysteamine 2 (424 mg or 5.6 mmoles) and bromoacetyldiBocspermidine 1 (2.56 g or 5.49 mmoles) dissolved in 10 mL of methanol containing 1.4 mL of NaOH 5N is left at room temperature overnight. Upon evaporation to dryness, the residue is resuspended in CHCl3, washed with water, dried on MgSO4 and evaporated to yield 2.4 g (5.19 mmoles) of compound 3 with molar mass 462 g/mol (C21H42N4O5S). MS: m/z=463 (M+H)+.

Compound 2.

Compound 3 (2.4 g or 5.19 mmoles) is dissolved with the calcium salt of natural D(+)pantothenic acid 4 (1.36 g or 2.85 mmoles) in 100 mL DMF including 2.52 g BOP (1 equivalent) and 1.27 g of N-methylmorpholine (using a water bath to accelerate the complete dissolution). The mixture is kept overnight at room temperature and evaporated under vacuum. The residue is dissolved in ethylacetate. The organic layer is washed 3 times with water thus affording 2.04 g of a product with two spots by TLC. The purification is achieved by preparative TLC (200×200×2 mm) using CHCl3 with 25% CH3OH. The fast migrating

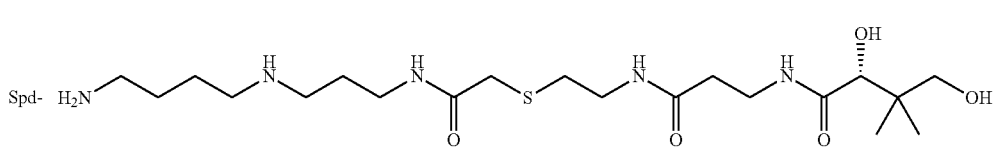

band is recovered affording 1.2 (1.81 mmole) of 5 (663 g/mol for C30H57N5O9S). MS: m/z=664 (M+H)+. Total yield: 35%.

Compound Spd-4a.

Compound 5 (186 mg) is treated with TFA 5 mL during 30 min at room temperature. TFA was eliminated through evaporation under vacuum thus affording Spd-4a (base: C20H41N5O5S; 463.6 g/mol) as the TFA salt in quantitative yield.

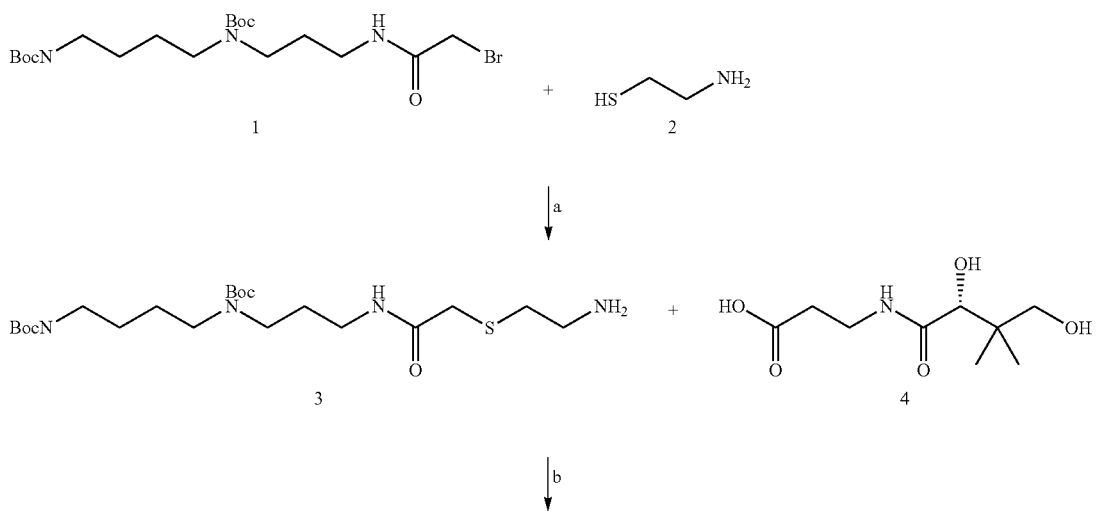

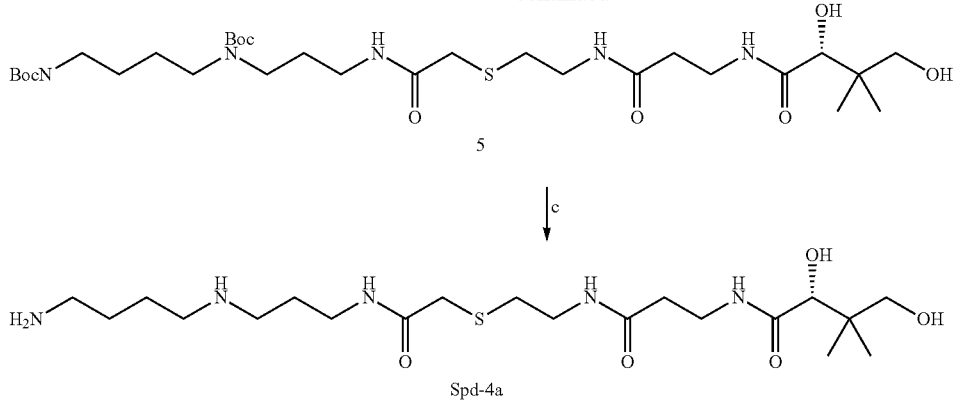

Spd-4a

Synthesis of Spd-4a (See Accompanying Protocol). Experimental conditions: a=methanol containing 1.4 mL of NaOH 5N is left at room temperature overnight; b=DMF including 2.52 g BOP (1 equivalent) and 1.27 g of N-methylmorpholine; c=TFA during 30 min at room temperature.

Example 12

This Example demonstrates expanded use of spd-1a and spd-2a to suppress triple negative breast cancer as single agents.

The present inventors previously reported on the effects of the synthetic polyamine-CoA-based HAT inhibitors, spd-1a and spd-2a as therapy sensitizers, and they linked this effect to inhibition of DNA repair. They reported that the spd-CoA (spd-1a) HAT inhibitor causes a rapid inhibition of histone acetylation in treated cancer cells that correlates with a transient arrest of DNA synthesis, a transient delay in S-phase progression, and an inhibition of two types of DNA repair, namely nucleotide excision repair and double strand break repair. See Bandyopadhyay, K. et al. Spermidinyl-CoA-based HAT inhibitors block DNA repair and provide cancer-specific chemo- and radiosensitization. *Cell Cycle* 8, 2779-2788 (2009).

The present inventors showed that spd-1a had little effect on two cancer cell lines, MCF7 ER+ breast cancer cells and H358 lung cancer cells when used as a single agent. However, the 3-day viabilities of both cell lines could be suppressed by over 90% when spd-1a was combined with a dose of a DNA-damaging chemotherapeutic agent that was sublethal by itself, and this correlated with a failure to repair the DNA damage. A similar, though slightly better sensitization effect was observed with the spd-2a compound. They also found that neither spd-1a nor spd-2a had any sensitization effect on normal human fibroblasts or epithelial cells unless they were permeabilized by brief detergent treatment, indicating that the unpermeabilized normal cells do not internalize these compounds. They subsequently provided evidence that internalization of these compounds likely occurs via the polyamine transporter, which is more active in cancer cells (see Example 5).

Tumors often display elevated polyamine transport through the transporter so this could account for the cancer-cell selective effects. The present inventors suspected that polyamine-CoA-based compounds would be non-toxic in vivo, and they have confirmed this in pilot toxicity studies in mice (see item 2 below).

The present inventors have also discovered an expanded use of these compounds for triple negative breast cancer (TNBC) and other cancers with defects in DNA repair. TNBC is a very aggressive form of breast cancer that carries a poor prognosis and poses a challenge for treatment. Hispanic and African American ethnicity and inherited mutation of the BrCa1 breast cancer gene are risk factors for TNBC.

TNBC lacks expression of the estrogen, progesterone, and Her-2 receptors, and is not a candidate for the widely used anti-estrogens, aromatase inhibitors, and anti-HER-2 therapies that target these receptors. Because there is no established therapeutic target in TNBC, treatment relies on conventional chemotherapy. However, chemotherapy is associated with considerable toxicity, and chemoresistance remains a major obstacle to successful treatment. A major unmet challenge in breast cancer research is to identify therapeutic targets for TNBC, and to use them to design more effective, less toxic therapies tailored specifically for this disease.

Defective DNA repair is common in triple negative breast cancers. This feature underlies the disease process by destabilizing the cellular genome and promoting the accumulation of cancer-causing genetic abnormalities. At the same time the DNA repair defect creates a therapeutic opportunity because it increases the frequency of potentially toxic DNA strand breaks and renders the cell highly vulnerable to further inhibition of DNA repair.

Other embodiments of the present invention show that spd-1a and spd-2a were ineffective as single agents in the cancer cell lines tested. Unexpectedly, the present inventors found that TNBC-derived breast cancer cells are suppressed by spd-2a even as a single agent. Histone acetyltransferase is therefore a novel target for TNBC, and one that holds promise because of its central role in DNA repair functions needed for TNBC cell survival. The concept is diagrammed in the scheme at the left for BrCa1-mutated cancers This example shows that Spermidine-2a as a single agent suppresses breast cancer cells with BrCa1 defects. In the experiment in FIG. 22, the present inventors examined the 3-day viability the ER+ MCF7 cell line, before and after treatment to down-regulate BrCA1 expression. BrCa1 siRNA treatment suppressed BrCa1 protein by 70% compared to untreated control cells by 48 hrs post-treatment. Si-RNA-treated cells or control cells were then grown 3 days in 96-well plates in the presence of increasing doses of spd-2a (in triplicate), followed by an MTS cell viability assay. As shown in FIG. 22A, treatment with spd-2a alone had little effect on MCF7 cells that received no siRNA or control (scrambled) siRNA. In contrast, treatment with BrCa1 siRNA greatly increased sensitivity to spd-2a, resulting in complete suppression of cell viability at the highest dose of spd-2a.

To show how BrCa1 mutation would effect the cellular response to spd-2a, the present inventors compared the responses of the H358 lung cancer cell line, which expresses wild-type BrCa1, to the TNBC cell line HCC1937, derived from a breast cancer carrying a common BrCa1 mutation (codon 185, insertion C at BrCa1 nucleotide 5382). See Tomlinson, G. E., et al., Characterization of a breast cancer cell line derived from a germ-line BRCA1 mutation carrier. *Cancer Res* 58, 3237-3242 (1998). Cell viability assays were carried out as in FIG. 22A. As shown in FIG. 22B, BrCa1 mutant HCC 1937 cells display a marked sensitivity to single agent treatment with spd-2a, while the H358 cell line remains resistant.

The effect of spd-2a on the BT20 breast cancer cell line derived form a spontaneous TNBC with wild-type BrCa1 was examined. Three-day viability assays show that BT20 cells are also suppressed by single agent treatment with spd-2a, while the same treatment has minimal effects on H358 lung cancer cells (FIG. 22C). Having previously established that spd-2a is a therapy sensitizer, the present inventors then examined the combined effects of spd-2a and camptothecin (the basis for the chemotherapeutic drug, Irinotecan). They found that in the presence of a sub-lethal dose of camptothecin (5 nM has no effect on BT20 cells by itself), addition of increasing doses of spd-2a resulted in complete suppression of BT20 cell viability (FIG. 22C).

Example 13

This example further shows that polyamine-CoA conjugates are non toxic in mice. The present inventors tested the in vivo toxicity in nude mice of spd-2a by carrying out tail vein injections (100 µl per 25 gm mouse) of spd-2a at concentrations varying from 0.25 mM to 20 mM, corresponding to a maximum dose of 40 mg/kg, and equivalent to a maximum initial blood concentration of about 1 mM. Mice were observed for several days and showed no signs of distress or illness. They injected a second set of 4 mice with 100 µl of spd-3a (5 mM, approximately 10 mg/kg, or about 0.25 mM initial blood concentration), twice per week for 3 weeks. The mice displayed no signs of distress or illness, and they did not lose weight over this time period. The spd-2a and spd-3a compounds therefore appear to be non-toxic in mice. This is consistent with other reports where alkylated spermidine analogues have displayed only mild host toxicity in mice, with maximum tolerated doses as a single intraperitoneal injection of greater than 400 mg/kg, equivalent to about 16 mM maximal blood concentration. It is also consistent with the observation by the present inventors that normal human fibroblasts and epithelial cells do not take up spermidine-CoA based compounds and the data in Example 5, linking this to low level expression of the polyamine transporter on these normal cells.

The experiments in FIGS. 23A and 23B demonstrate uptake and stability of various polyamine conjugates in H358 non small cell lung cancer cells, including new compounds, spm 2 and spm3 received from Dr. Casimir Blonksi (Laboratoire de Chimie Bioorganique et Bioinorganique; ICMMO, UMR CNRS 8182; Université Paris-Sud 11; Orsay, France) on Jan. 20, 2011. The results show that all of the conjugates studied are efficiently internalized and display improved uptake and stability compared to spermidine-1a (spd-1a).

Example 14

This example shows that spm-2 and spm-3 are all HAT inhibitors. See FIG. 24.

Example 15

This example shows that spd-3a, spm-2 and spm-3 all inhibit DNA synthesis in H358 cells. See FIG. 25.

Example 16

This example shows the inhibition of cell viability by spd-3a as a single agent. These assays shows that spd-3a is effective when used singly on multiple cancer cell lines. The assays also shows that normal GT41 fibroblasts are less sensitive to spd-3a than are the three cancer cell lines tested (DLD1 colon cancer cells, DU145 prostate cancer cells, and H358 lung cancer cells). GT41F cells retain some 60% viability at a dose of spd-3a (1 µM) that inhibits >95% of H358 cell viability and essentially 100% of DU145 cell viability. There is therefore selectivity for cancer cells in this case. See FIG. 26.

The following assay, shown in FIG. 27, shows that spm-2 and spm-3 are both effective as single agents in DLD-1 cells and H358 cells in suppressing cancer cell growth and viability. Normal GT41 fibroblasts display a sensitivity similar to that of H358 lung cancer cells but they are less sensitive that DLD-1colon cancer cells. The results indicate that for some cancers, typified by DLD-1 cells, a therapeutic window could be found in which the compounds displayed cancer cell selectivity.

The assay shown in FIG. 28 shows that spm2, spm-3, and spd-3a all suppress histone acetylation in treated cells.

Throughout this application, various publications are referenced. All such references, specifically those listed below, are incorporated herein by reference.

Allfrey, V. G. and Mirsky, A. E. Structural Modifications of Histones and their Possible Role in the Regulation of RNA Synthesis. Science, 144: 559, 1964.

Allis, C. D., Berger, S. L., Cote, J., Dent, S., Jenuwien, T., Kouzarides, T., Pillus, L., Reinberg, D., Shi, Y., Shiekhattar, R., Shilatifard, A., Workman, J., and Zhang, Y. New nomenclature for chromatin-modifying enzymes. Cell, 131: 633-636, 2007.

Allis, C. D., Chicoine, L. G., Richman, R., and Schulman, I. G. Deposition-related histone acetylation in micronuclei of conjugating Tetrahymena. Proc Natl Acad Sci USA, 82: 8048-8052, 1985.

Avemann, K., Knippers, R., Koller, T., and Sogo, J. M. Camptothecin, a specific inhibitor of type I DNA topoisomerase, induces DNA breakage at replication forks. Mol Cell Biol, 8: 3026-3034, 1988.

Balasubramanyam, K., Altaf, M., Varier, R. A., Swaminathan, V., Ravindran, A., Sadhale, P. P., and Kundu, T. K. Polyisoprenylated benzophenone, garcinol, a natural histone acetyltransferase inhibitor, represses chromatin transcription and alters global gene expression. J Biol Chem, 279: 33716-33726, 2004.

Balasubramanyam, K., Swaminathan, V., Ranganathan, A., and Kundu, T. K. Small molecule modulators of histone acetyltransferase p300. J Biol Chem, 278: 19134-19140, 2003.

Balasubramanyam, K., Varier, R. A., Altaf, M., Swaminathan, V., Siddappa, N. B., Ranga, U., and Kundu, T. K. Curcumin, a novel p300/CREB-binding protein-specific inhibitor of acetyltransferase, represses the acetylation of histone/nonhistone proteins and histone acetyltransferase-dependent chromatin transcription. J Biol Chem, 279: 51163-51171, 2004.

Bandyopadhyay, K., Lee, C., Haghighi, A., Baneres, J. L., Parello, J., and Gjerset, R. A. Serine phosphorylation-dependent coregulation of topoisomerase I by the p14ARF tumor suppressor. Biochemistry, 46: 14325-14334, 2007.

Baneres, J. L., Martin, A., and Parello, J. The N tails of histones H3 and H4 adopt a highly structured conformation in the nucleosome. J Mol Biol, 273: 503-508, 1997.

Bogdanov, K. V., Chukhlovin, A. B., Zaritskey, A. Y., Frolova, O. I., and Afanasiev, B. V. Ultraviolet irradiation induces multiple DNA double-strand breaks and apoptosis in normal granulocytes and chronic myeloid leukaemia blasts. Br J Haematol, 98: 869-872, 1997.

Cazzalini, O., Perucca, P., Savio, M., Necchi, D., Bianchi, L., Stivala, L. A., Ducommun, B., Scovassi, A. I., and Prosperi, E. Interaction of p21(CDKN1A) with PCNA regulates the histone acetyltransferase activity of p300 in nucleotide excision repair. Nucleic Acids Res, 36: 1713-1722, 2008.

Cullis, P. M., Wolfenden, R., Cousens, L. S., and Alberts, B. M. Inhibition of histone acetylation by N-[2-(S-coenzyme A)acetyl] spermidine amide, a multisubstrate analog. J Biol Chem, 257: 12165-12169, 1982.

Dumuis-Kervabon, A., Encontre, I., Etienne, G., Jauregui-Adell, J., Mery, J., Mesnier, D., and Parello, J. A chromatin core particle obtained by selective cleavage of histones by clostripain. Embo J, 5: 1735-1742, 1986.

Eliseeva, E. D., Valkov, V., Jung, M., and Jung, M. O. Characterization of novel inhibitors of histone acetyltransferases. Mol Cancer Ther, 6: 2391-2398, 2007.

Garcia-Carbonero, R. and Supko, J. G. Current perspectives on the clinical experience, pharmacology, and continued development of the camptothecins. Clin Cancer Res, 8: 641-661, 2002.

Hasan, S., Hassa, P. O., Imhof, R., and Hottiger, M. O. Transcription coactivator p300 binds PCNA and may have a role in DNA repair synthesis. Nature, 410: 387-391, 2001.

Herceg, Z. and Wang, Z. Q. Rendez-vous at mitosis: TRRAPed in the chromatin. Cell Cycle, 4: 383-387, 2005.

Jacobson, S. and Pillus, L. Modifying chromatin and concepts of cancer. Curr Opin Genet Dev, 9: 175-184, 1999.

Kornberg, R. D. and Lorch, Y. Twenty-five years of the nucleosome, fundamental particle of the eukaryote chromosome. Cell, 98: 285-294, 1999.

Kusch, T., Florens, L., Macdonald, W. H., Swanson, S. K., Glaser, R. L., Yates, J. R., 3rd, Abmayr, S. M., Washburn, M. P., and Workman, J. L. Acetylation by Tip60 is required for selective histone variant exchange at DNA lesions. Science, 306: 2084-2087, 2004.

Lau, O. D., Kundu, T. K., Soccio, R. E., Ait-Si-Ali, S., Khalil, E. M., Vassilev, A., Wolffe, A. P., Nakatani, Y., Roeder, R. G., and Cole, P. A. HATs off: selective synthetic inhibitors of the histone acetyltransferases p300 and PCAF. Mol Cell, 5: 589-595, 2000.

Lee, D. Y., Hayes, J. J., Pruss, D., and Wolffe, A. P. A positive role for histone acetylation in transcription factor access to nucleosomal DNA. Cell, 72: 73-84, 1993.

Pavon, M. A., Parreno, M., Leon, X., Sancho, F. J., Cespedes, M. V., Casanova, I., Lopez-Pousa, A., Mangues, M. A., Quer, M., Barnadas, A., and Mangues, R. Ku70 predicts response and primary tumor recurrence after therapy in locally advanced head and neck cancer. Int J Cancer, 123: 1068-1079, 2008.

Pegg, A. E. Spermidine/spermine-N(1)-acetyltransferase: a key metabolic regulator. Am J Physiol Endocrinol Metab, 294: E995-1010, 2008.

Rogakou, E. P., Boon, C., Redon, C., and Bonner, W. M. Megabase chromatin domains involved in DNA double-strand breaks in vivo. J Cell Biol, 146: 905-916, 1999.

Saadatmandi, N., Tyler, T., Huang, Y., Haghighi, A., Frost, G., Borgstrom, P., and Gjerset, R. A. Growth suppression by a p14(ARF) exon 1beta adenovirus in human tumor cell lines of varying p53 and Rb status. Cancer Gene Ther, 9: 830-839, 2002.

Suter, B., Pogoutse, O., Guo, X., Krogan, N., Lewis, P., Greenblatt, J. F., Rine, J., and Emili, A. Association with the origin recognition complex suggests a novel role for histone acetyltransferase Hat1p/Hat2p. BMC Biol, 5: 38, 2007.

Tang, Y., Luo, J., Zhang, W., and Gu, W. Tip60-dependent acetylation of p53 modulates the decision between cell-cycle arrest and apoptosis. Mol Cell, 24: 827-839, 2006.

Wurtele, H. and Verreault, A. Histone post-translational modifications and the response to DNA double-strand breaks. Curr Opin Cell Biol, 18: 137-144, 2006.

Yang, X. J. The diverse superfamily of lysine acetyltransferases and their roles in leukemia and other diseases. Nucleic Acids Res, 32: 959-976, 2004.

Zheng, Y., Balasubramanyam, K., Cebrat, M., Buck, D., Guidez, F., Zelent, A., Alani, R. M., and Cole, P. A. Synthesis and evaluation of a potent and selective cell-permeable p300 histone acetyltransferase inhibitor. J Am Chem Soc, 127: 17182-17183, 2005.

Thomas, T. and Thomas, T. J. Polyamines in cell growth and cell death: molecular mechanisms and therapeutic applications. Cell Mol Life Sci 2001; 58:244-58.

Gerner, E. W. and Meyskens, F. L., Jr. Polyamines and cancer: old molecules, new understanding. Nat Rev Cancer 2004; 4:781-92.

Auvinen, M., Paasinen, A., Andersson, L. C., and Holtta, E. Ornithine decarboxylase activity is critical for cell transformation. Nature 1992; 360:355-8.

Canizares, F., Salinas, J., de las Heras, M., et al. Prognostic value of ornithine decarboxylase and polyamines in human breast cancer: correlation with clinicopathologic parameters. Clin Cancer Res 1999; 5:2035-41.

Manni, A., Mauger, D., Gimotty, P., and Badger, B. Prognostic influence on survival of increased ornithine decarboxylase activity in human breast cancer. Clin Cancer Res 1996; 2:1901-6.

Persson, L. and Rosengren, E. Increased formation of N1-acetylspermidine in human breast cancer. Cancer Lett 1989; 45:83-6.

Hu, R. H. and Pegg, A. E. Rapid induction of apoptosis by deregulated uptake of polyamine analogues. Biochem J 1997; 328 (Pt 1):307-16.

Seiler, N., Delcros, J. G., and Moulinoux, J. P. Polyamine transport in mammalian cells. An update. Int J Biochem Cell Biol 1996; 28:843-61.

Manni, A., Washington, S., Craig, L., et al. Effects of alpha-difluoromethylornithine on local recurrence and pulmonary metastasis from MDA-MB-435 breast cancer xenografts in nude mice. Clin Exp Metastasis 2003; 20:321-5.

Manni, A., Washington, S., Griffith, J. W., et al. Influence of polyamines on in vitro and in vivo features of aggressive and metastatic behavior by human breast cancer cells. Clin Exp Metastasis 2002; 19:95-105.

Manni, A., Washington, S., Hu, X., et al. Effects of polyamine synthesis inhibitors on primary tumor features and metastatic capacity of human breast cancer cells. Clin Exp Metastasis 2005; 22:255-63.

Jun, J. Y., Griffith, J. W., Bruggeman, R., et al. Effects of polyamine depletion by alpha-difluoromethylornithine on in vitro and in vivo biological properties of 4T1 murine mammary cancer cells. Breast Cancer Res Treat 2008; 107:33-40.

Casero, R. A., Jr. and Woster, P. M. Recent advances in the development of polyamine analogues as antitumor agents. J Med Chem 2009; 52:4551-73.

Wolff, A. C., Armstrong, D. K., Fetting, J. H., et al. A Phase II study of the polyamine analog N1,N11-diethylnorspermine (DENSpm) daily for five days every 21 days in patients with previously treated metastatic breast cancer. Clin Cancer Res 2003; 9:5922-8.

Pegg, A. E. Polyamine metabolism and its importance in neoplastic growth and a target for chemotherapy. Cancer Res 1988; 48:759-74.

Bandyopadhyay, K., Baneres, J. L., Martin, A., et al. Spermidinyl-CoA-based HAT inhibitors block DNA repair and provide cancer-specific chemo- and radiosensitization. Cell Cycle 2009; 8:2779-88.

Bandyopadhyay, K., Baneres, J. L., Martin, A., Blonski, C., Parello, J., and Gjerset, R. A. (2009) Spermidinyl-CoA-based HAT inhibitors block DNA repair and provide cancer-specific chemo- and radiosensitization. *Cell Cycle* 8, 2779-2788.

Wolf, M., Bauder-Wust, U., Pipkorn, R., Eskerski, H., and Eisenhut, M. (2006) Fluorophor-labeled spermidine derivatives as fluorescent markers in optical tumor imaging. *Bioorg Med Chem Lett* 16, 3193-3196.

Sorlie, T., Tibshirani, R., Parker, J., Hastie, T., Marron, J. S., Nobel, A., Deng, S., Johnsen, H., Pesich, R., Geisler, S., Demeter, J., Perou, C. M., Lonning, P. E., Brown, P. O., Borresen-Dale, A. L., and Botstein, D. (2003) Repeated observation of breast tumor subtypes in independent gene expression data sets. *Proc Natl Acad Sci USA* 100, 8418-8423.

Morris, G. J., Naidu, S., Topham, A. K., Guiles, F., Xu, Y., McCue, P., Schwartz, G. F., Park, P. K., Rosenberg, A. L., Brill, K., and Mitchell, E. P. (2007) Differences in breast carcinoma characteristics in newly diagnosed African-American and Caucasian patients: a single-institution compilation compared with the National Cancer Institute's Surveillance, Epidemiology, and End Results database. *Cancer* 110, 876-884.

Turner, N., Tutt, A., and Ashworth, A. (2004) Hallmarks of 'BRCAness' in sporadic cancers. *Nat Rev Cancer* 4, 814-819.

Hart, I. R., and Easty, D. (1991) Tumor cell progression and differentiation in metastasis. *Semin Cancer Biol* 2, 87-95.

Tomlinson, G. E., Chen, T. T., Stastny, V. A., Virmani, A. K., Spillman, M. A., Tonk, V., Blum, J. L., Schneider, N. R., Wistuba, II, Shay, J. W., Minna, J. D., and Gazdar, A. F. (1998) Characterization of a breast cancer cell line derived from a germ-line BRCA1 mutation carrier. *Cancer Res* 58, 3237-3242.

Bernacki, R. J., Oberman, E. J., Seweryniak, K. E., Atwood, A., Bergeron, R. J., and Porter, C. W. (1995) Preclinical antitumor efficacy of the polyamine analogue N1,N11-diethylnorspermine administered by multiple injection or continuous infusion. *Clin Cancer Res* 1, 847-857.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

We claim:

1. A method of treating cancer in a subject in need thereof, comprising:
   (i) administering to the subject a therapy sensitizing effective amount of compound of the following formula:

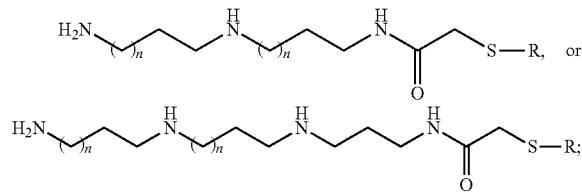

wherein
n is independently 1, or 2;
R is $(CH_2)_2NHCOR^3$, or $(CH_2)_2NHCO(CH_2)_2NHCOR^3$; and
$R^3$ is alkyl;
or a pharmaceutically acceptable salt or hydrate thereof; and
   (ii) administering to said subject in need thereof an anti-cancer agent or a therapeutic anti-cancer combination; thereby treating the cancer.

2. The method of claim 1, wherein $R^3$ is methyl.

3. The method of claim 1, wherein the anticancer agent is chosen from carboplatin, gemcitabine, cisplatin, 5-fluorouracil, cyclophosphamide, etoposide, vincristine, doxorubicin, DFMO and/or irinotecan.

4. A method of treating cancer in a subject in need thereof, comprising administering to the subject a cancer treating or ameliorating effective amount of a compound of the following formula:

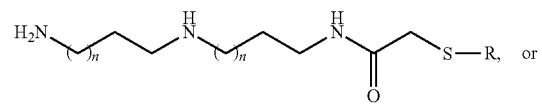

-continued
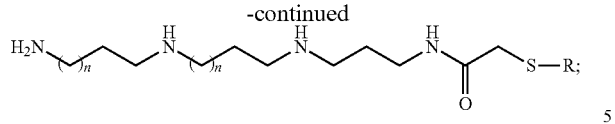
wherein
n is independently 1, or 2;
R is $(CH_2)_2NHCOR^3$, or $(CH_2)_2NHCO(CH_2)_2NHCOR^3$; and
$R^3$ is alkyl;
or a pharmaceutically acceptable salt or hydrate thereof.
5. The method of claim 4, wherein $R^3$ is methyl.
* * * * *